(12) United States Patent
Gerecht et al.

(10) Patent No.: US 11,779,682 B2
(45) Date of Patent: Oct. 10, 2023

(54) ELECTRO-MECHANICALLY STRETCHED MICRO FIBERS AND METHODS OF USE THEREOF

(71) Applicant: THE JOHNS HOPKINS UNIVERSITY, Baltimore, MD (US)

(72) Inventors: Sharon Gerecht, Severna Park, MD (US); Shuming Zhang, Lehigh Acres, FL (US); Sebastian F. Barreto Ortiz, Baltimore, TX (US); Hai-Quan Mao, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 521 days.

(21) Appl. No.: 16/152,556

(22) Filed: Oct. 5, 2018

(65) Prior Publication Data

US 2019/0070339 A1    Mar. 7, 2019

Related U.S. Application Data

(63) Continuation-in-part of application No. 14/398,072, filed as application No. PCT/US2013/038805 on Apr. 30, 2013, now Pat. No. 10,119,202.
(Continued)

(51) Int. Cl.
*A61L 27/52* (2006.01)
*A61L 27/58* (2006.01)
(Continued)

(52) U.S. Cl.
CPC .............. *A61L 27/52* (2013.01); *A61L 27/225* (2013.01); *A61L 27/3633* (2013.01);
(Continued)

(58) Field of Classification Search
CPC .... A61L 27/52; A61L 27/225; A61L 27/3808; A61L 27/3826; A61L 27/3886;
(Continued)

(56) References Cited

U.S. PATENT DOCUMENTS

| | | |
|---|---|---|
| 7,086,846 B2 | 8/2006 | Kleinmeyer |
| 8,012,399 B2 | 9/2011 | Gee |

(Continued)

FOREIGN PATENT DOCUMENTS

| | | |
|---|---|---|
| EP | 1994949 A1 | 11/2008 |
| WO | 2004/080681 A1 | 9/2004 |

OTHER PUBLICATIONS

Kusuma et al. "The Extracellular Matrix is a Novel Attribute of Endothelial Progenitors and of Hypoxic Mature Endothelial Cells," The FASEB Journal, Aug. 23, 2012. (Year: 2012).*
(Continued)

*Primary Examiner* — Matthew D Matzek
(74) *Attorney, Agent, or Firm* — Venable LLP; Keith G. Haddaway; Brenden G. McDearmon

(57) ABSTRACT

The presently disclosed subject matter provides a scalable and electrostretching approach for generating hydrogel microfibers exhibiting uniaxial alignment from aqueous polymer solutions. Such hydrogel microfibers can be generated from a variety of water-soluble natural polymers or synthetic polymers. The hydrogel microfibers can be used for controlled release of bioactive agents. The internal uniaxial alignment exhibited by the presently disclosed hydrogel fibers provides improved mechanical properties to hydrogel microfibers, and contact guidance cues and induces alignment for cells seeded on or within the hydrogel microfibers.

34 Claims, 50 Drawing Sheets

Related U.S. Application Data

(60) Provisional application No. 61/665,498, filed on Jun. 28, 2012, provisional application No. 61/640,057, filed on Apr. 30, 2012.

(51) Int. Cl.
*A61L 27/38* (2006.01)
*A61L 27/22* (2006.01)
*A61L 27/36* (2006.01)
*B82Y 5/00* (2011.01)

(52) U.S. Cl.
CPC ....... *A61L 27/3808* (2013.01); *A61L 27/3826* (2013.01); *A61L 27/3886* (2013.01); *A61L 27/58* (2013.01); *B82Y 5/00* (2013.01); *A61L 2400/12* (2013.01); *Y10T 428/29* (2015.01); *Y10T 428/2913* (2015.01); *Y10T 428/2922* (2015.01); *Y10T 428/2938* (2015.01)

(58) Field of Classification Search
CPC ........... A61L 27/58; B82Y 5/00; B82Y 30/00; Y10T 428/29; Y10T 428/2913; Y10T 428/298; D01F 9/04
USPC .................................. 977/762; 428/364, 903
See application file for complete search history.

(56) References Cited

U.S. PATENT DOCUMENTS

| | | | |
|---|---|---|---|
| 8,062,567 B2 | 11/2011 | Watanabe | |
| 2003/0006534 A1 | 1/2003 | Taboas et al. | |
| 2004/0037813 A1 | 2/2004 | Simpson et al. | |
| 2006/0085063 A1* | 4/2006 | Shastri ................. | A61L 27/34 623/1.41 |
| 2007/0018361 A1* | 1/2007 | Xu ........................ | D01F 9/08 264/465 |
| 2008/0025956 A1* | 1/2008 | Yoder ................ | G01N 33/5005 424/93.7 |
| 2008/0145934 A1* | 6/2008 | Harris ................... | A61L 27/227 435/404 |
| 2008/0220042 A1* | 9/2008 | Hashi .................... | A61K 38/58 514/1.1 |
| 2008/0241538 A1 | 10/2008 | Lee et al. | |
| 2008/0296808 A1* | 12/2008 | Joo ........................ | D01F 2/02 977/901 |
| 2009/0043380 A1* | 2/2009 | Blaha ................... | A61L 31/16 623/1.46 |
| 2009/0076530 A1 | 3/2009 | Fukutomi et al. | |
| 2010/0001438 A1 | 1/2010 | Kishimoto | |
| 2010/0291058 A1 | 11/2010 | Bowlin et al. | |
| 2011/0180972 A1 | 7/2011 | Lee et al. | |
| 2013/0018454 A1 | 1/2013 | Lelkes et al. | |
| 2015/0246072 A1* | 9/2015 | Bhatia ................... | A61L 27/38 424/93.7 |

OTHER PUBLICATIONS

International Search Report dated Aug. 12, 2013 for PCT/US2013/038805.
Wall et al., "Aligned macroscopic domains of optoelectronic nanostructures prepared via shear-flow assembly of peptide hydrogels", Adv. Mater., 23, 5009-5014 (2011).
Bellan et al., "Molecular orientation in individual electrospun nanofibers measured via polarized Raman spectroscopyl", Polymer 49, 3125-3129 (2008).
Yang et al., "Monitoring the effect of magnetically aligned collagen scaffolds on tendon tissue engineering by PSOCT", Proc. SPIE 7179, Optics in Tissue Engineering and Regenerative Medicine III, 717903 (Feb. 12, 2009).
Tonsomboon et al., "Composite electrospun gelatin fiber-alginate gel scaffolds for mechanically robust tissue engineered cornea", J. Mechanical Behavior of Biomedical Materials, 21:185-94 (2013).
Guo et al., "Flow and magnetic field induced collagen alignment", Biomaterials 28: 1105-1 114 (2007).
Kaneko et al., "Mechanically drawn hydrogels uniaxially orient hydroxyapatite crystals and cell extension", Chem. Mater. 5596-5601 (2004).
Zong et al., "Structure and process relationship of electrospun bioabsorbable nanofiber membranes", Polymer 43, 4403-4412 (2002).
Yang et al., "Electrospinning of nano/micro scale poly(L-lactic acid) aligned fibers and their potential in neural tissue engineering", Biomaterials 26, 2603—2610 (2005).
Williams et al., "In vitro chondrogenesis of bone marrow-derived mesenchymal stem cells in a photopolymerizing hydrogel", Tissue Engineering 9, 679-688 (2003).
Shu et al., "In situ crosslinkable hyaluronan hydrogels for tissue engineering", Biomaterials 25, 1339-1348 (2004).
Seliktar et al., "Cell-Compatible Hydrogels for Biomedical Applications", Science 336, 1124-1128 (2012).
Reneker et ai., "Bending instability of electrically charged liquid jets of polymer solutions in electrospinning", J. Appl. Phys. 87, 453•1-4547 (2000).
Potter et al., "The gelation of sodium alginate with calcium-ions studied by magnetic-resonance-imaging (MRI)", Carbohyd Res 257, 1 17-126 (1994).
Lim et al., "Electrospun scaffolds for stem cell engineering", Advanced Drug Delivery Reviews 61, 1084-1096 (2009).
Larson et al., "The Ericksen Number and Deborah Number cascades in sheared polymeric nematics", Liq. Cryst. 15, 151-169 (1993).
Kang et al., "Digitally tunable physicochemical coding of material composition and topography in continuous microfibres", Nature Materials 10, 877-883 (2011).
Kakade et al., "Electric field induced orientation of polymer chains in macroscopically aligned electrospun polymer nanofibers", Journal of the American Chemical Society 129, 2777-2782 (2007).
Ji et al., "Electrospun three-dimensional hyaluronic acid nanofibrous scaffolds", Biomaterials 27, 3782-3792 (2006).
Ji et al., "Dual-syringe reactive electrospinning of cross-linked hyaluronic acid hydrogel nanofibers for tissue engineering applications", Macromol Biosci 6, 81 1-817 (2006).
Inai et al., "Structure and properties of electrospun PLLA single nanofibers", Nanotechnology 16, 208-213 (2005).
Grasman et al., "Crosslinking strategies facilitate tunable structural properties of fibrin microthreads", Acta Biomaterialia 8, 4020-4030 (2012).
Fennessey et al., "Fabrication of aligned and molecularly oriented electrospun polyacrylon1trile nanofibers and the mechanical behavior of their twisted yams", Polymer 45, 4217-4225 (2004).
Discher et al., "Tissue cells feel and respond to the stiffness of their substrate", Science 310, 1139-1143 (2005).
Cornwell et al., "Discrete crosslinked fibrin microthread scaffolds for tissue regeneration", Journal of Biomedical Materials Research Part A 82A, 104-112 (2007).
Catalani et al., "Evidence for molecular orientation and residual charge in the electrospinning of poly(butylene terephthalate) nanofibers", Macromolecules 40, 1693-1697 (2007).
Burdick et al., "Photoencapsulation of osteoblasts in injectable RGD-modified PEG hydrogels for bone, tissue engineering", Biomaterials 23, 4315-4323 (2002).
Pant et al., "Fabrication of polymeric microfibers containing rice-like oligomeric hydrogel nanoparticles on their surface: A novel strategy in the electrospinning process", Materials Letters, 65('10), 1441-1444 (2011).
Lai et al., "Investigation of postsp1nning stretching process on morphological, structural, and mechanical properties of electrospun polyacrylonitrile copolymer nanofibers", Polymer, 52(2), 519-528 (2011).

\* cited by examiner

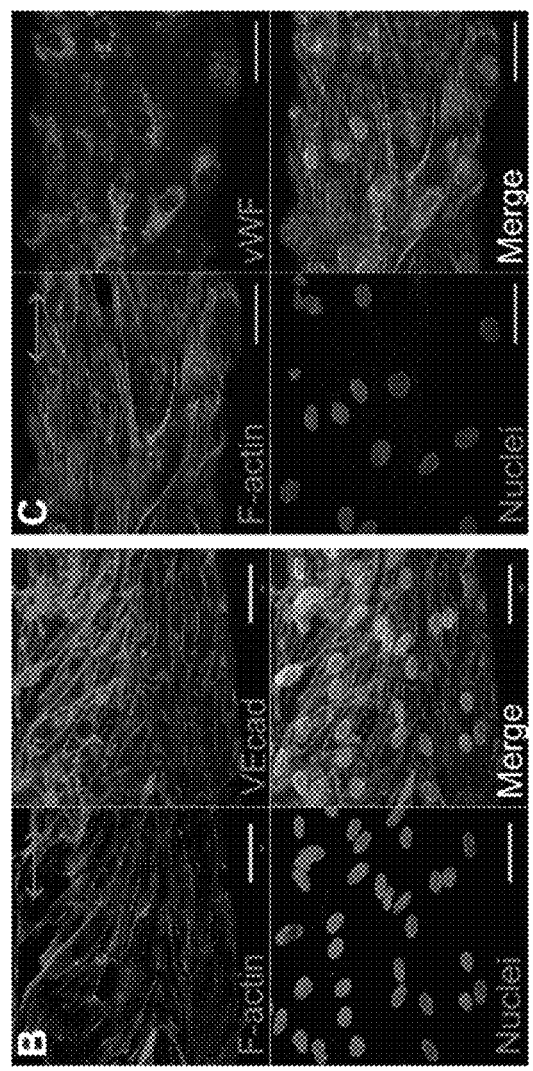

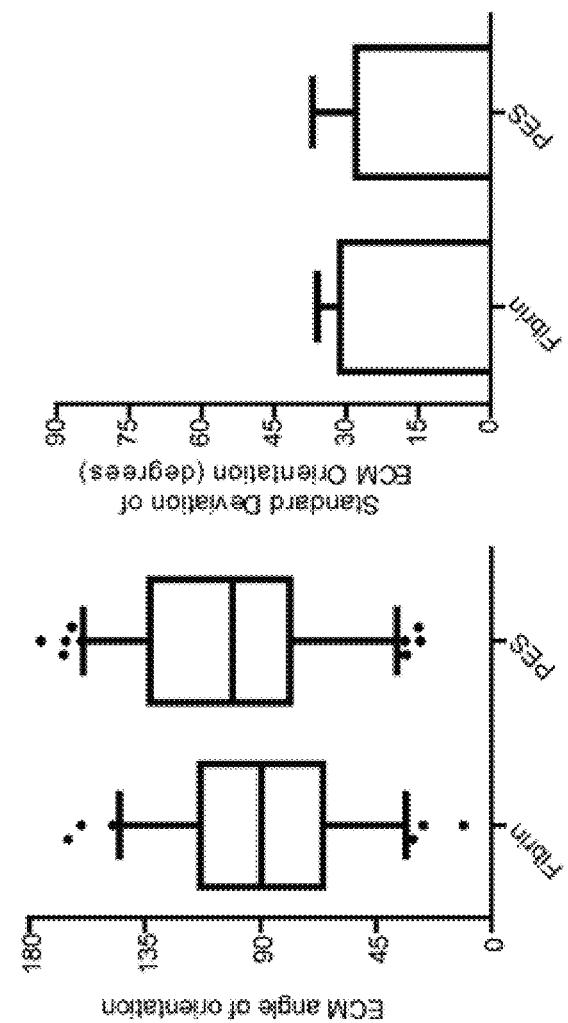
Fig. 9E
Fig. 9D
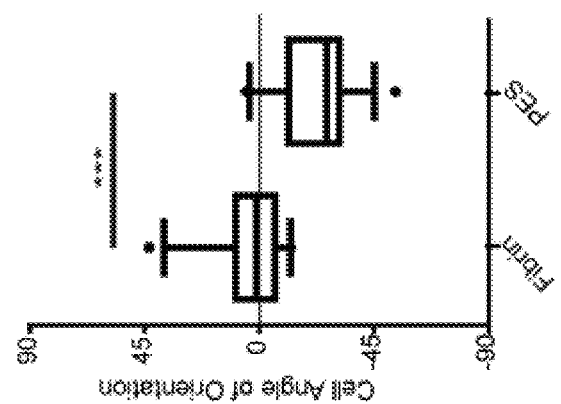
Fig. 9C

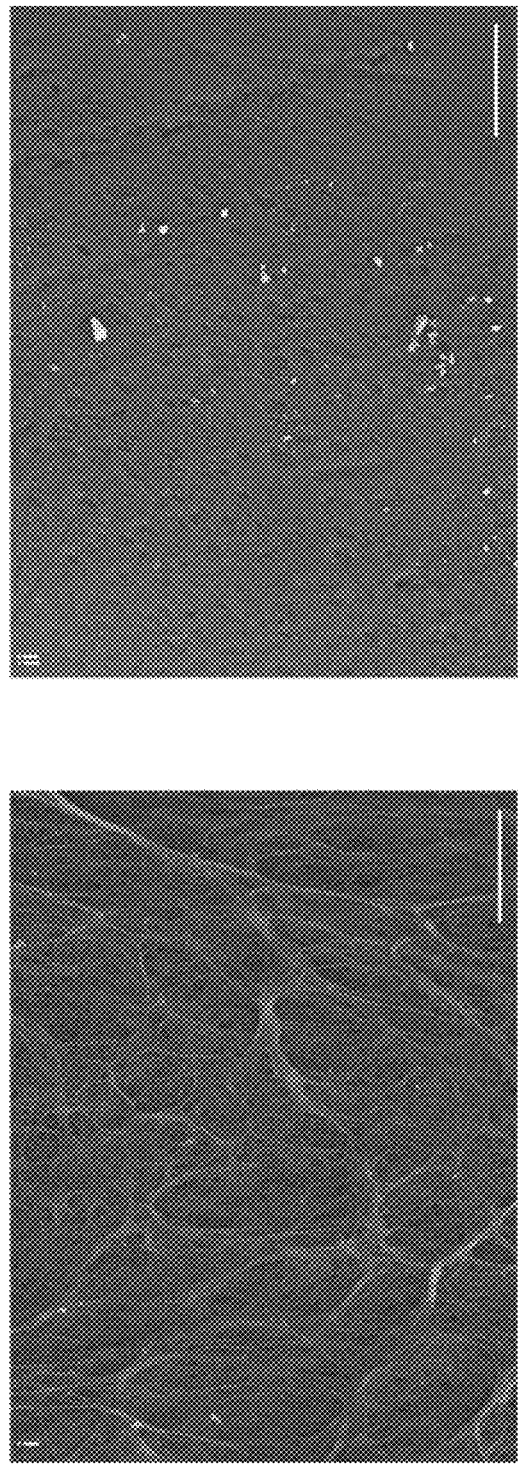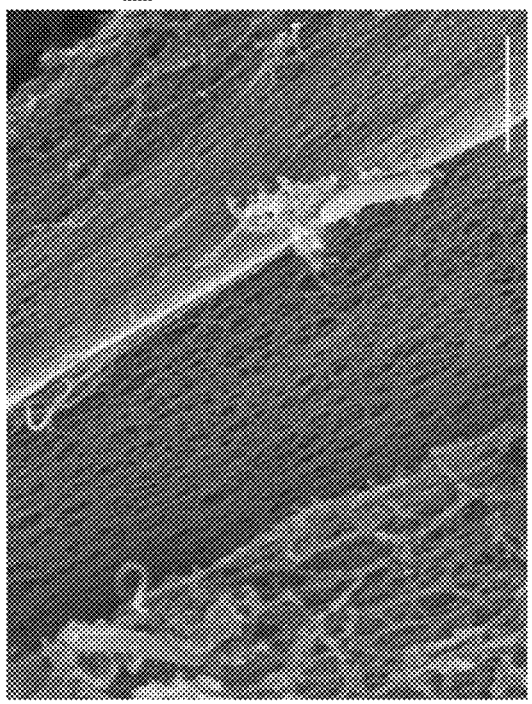

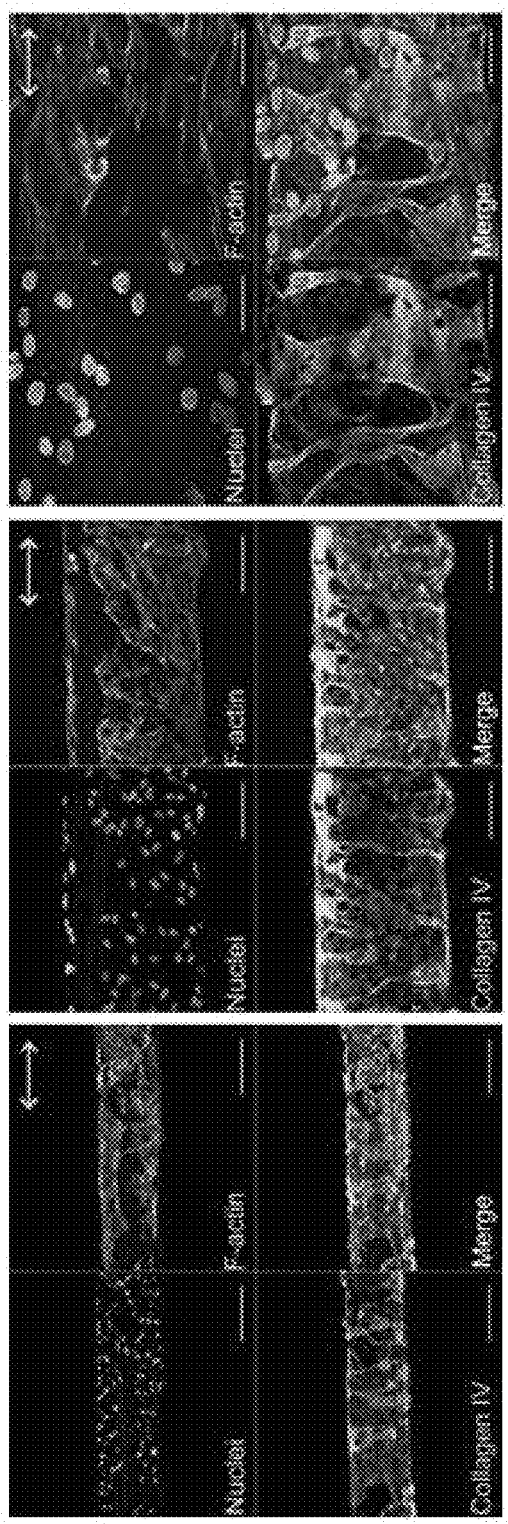

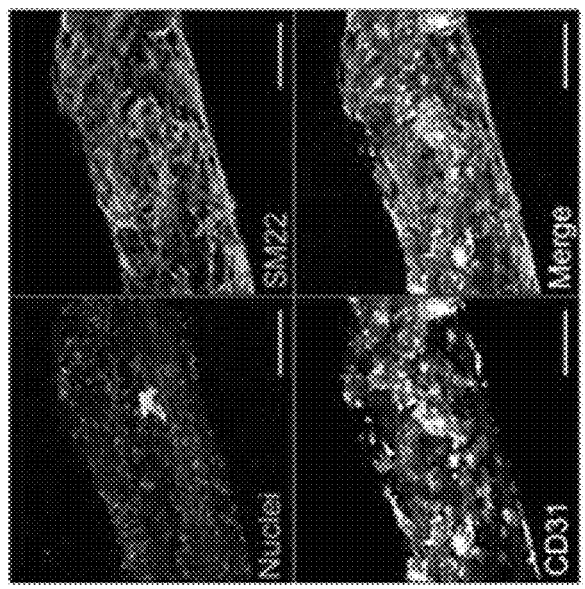
Fig 12A
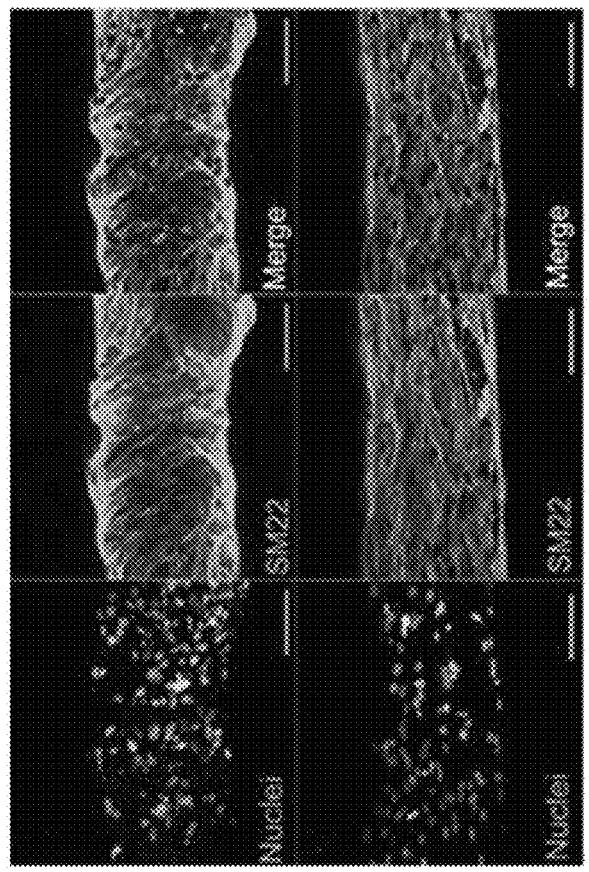
Fig. 12B
Fig 12C

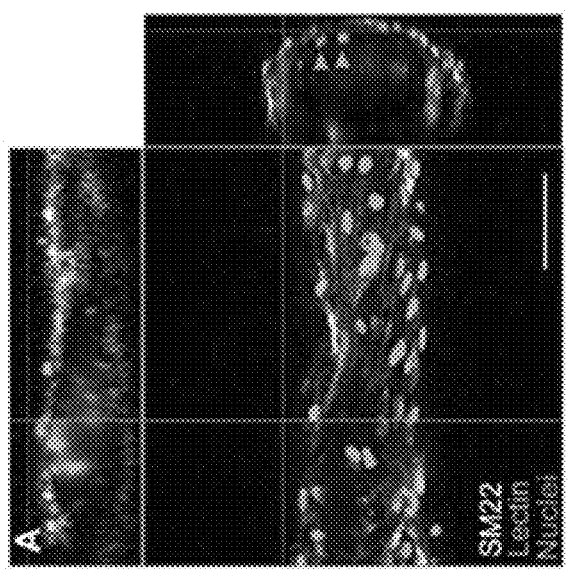
Fig. 13A
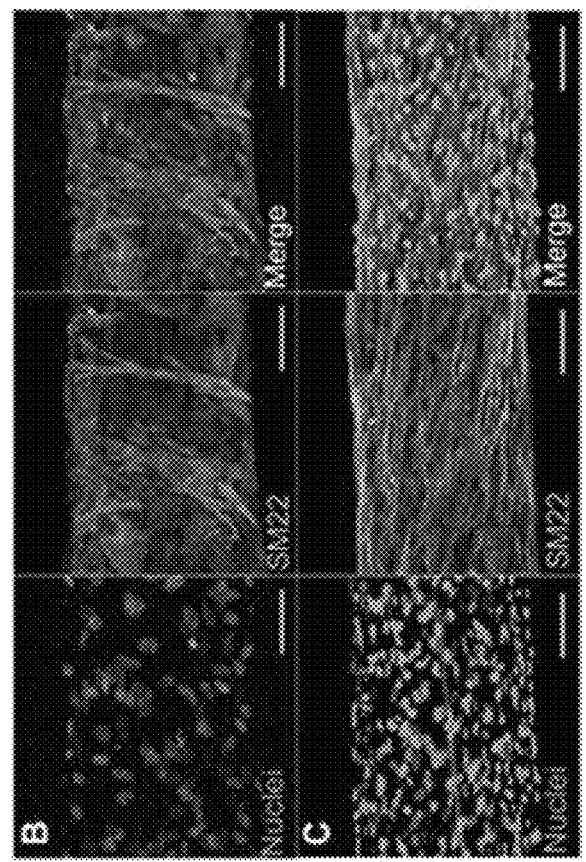
Fig. 13B
Fig. 13C

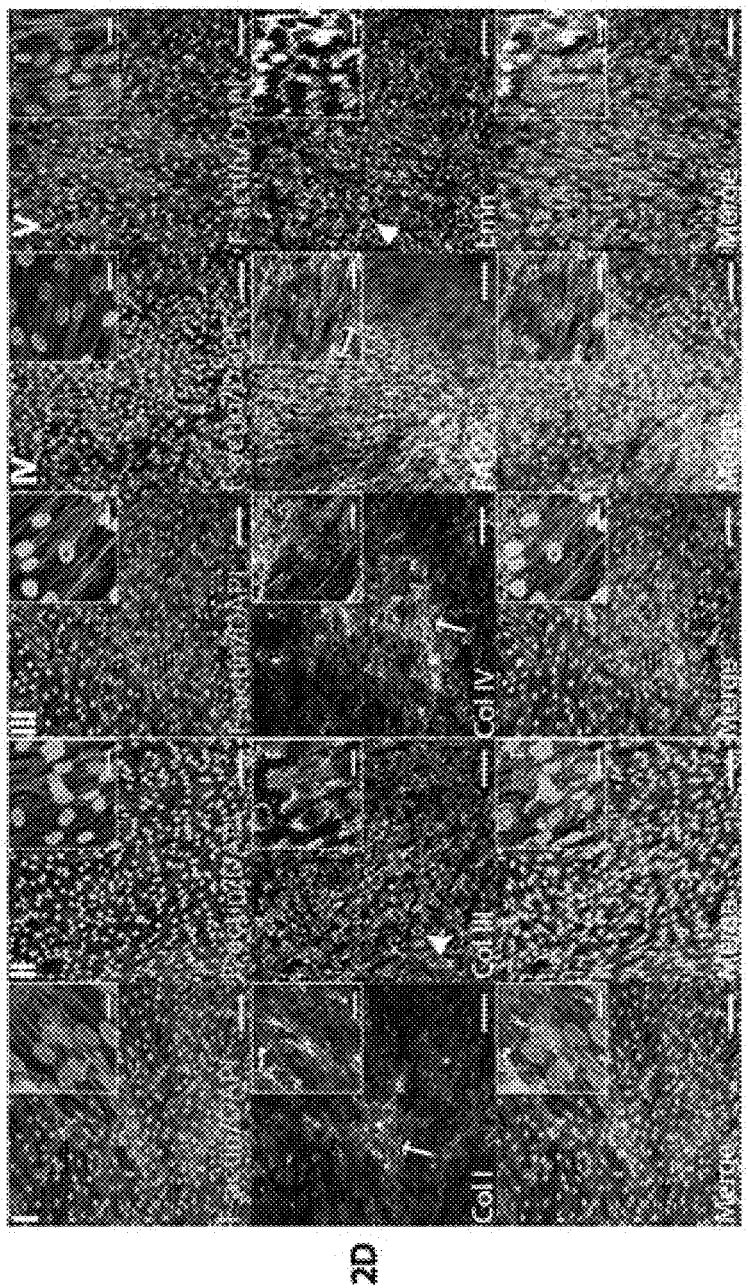

ELECTRO-MECHANICALLY STRETCHED MICRO FIBERS AND METHODS OF USE THEREOF

CROSS-REFERENCE TO RELATED APPLICATIONS

This application is a Continuation in Part (CIP) of U.S. application Ser. No. 14/398,072 that claims the benefit of International Patent Application No. PCT/US2013/038805, filed Apr. 30, 2013, and U.S. Provisional Application Nos. 61/640,057, filed Apr. 30, 2012, and 61/665,498, filed Jun. 28, 2012; and each of which is incorporated herein by reference in its entirety.

FEDERALLY SPONSORED RESEARCH OR DEVELOPMENT

This invention was made with government support under DMR-0748340 awarded by the National Science Foundation. The government has certain rights in the invention.

BACKGROUND

Hydrogels have been widely investigated for a variety of biomedical applications, particularly as scaffolds offering a 3-dimensional (3D) microenvironment for tissue regeneration. Hydrogels have been used for 3D cell culture and tissue regeneration because of their high water content resembling the aqueous microenvironment of the natural extracellular matrix (Seliktar, 2012) and tunable biochemical and physicochemical properties (Burdick and Anseth, 2002; Williams et al., 2003; Silva et al., 2004). While many properties of natural hydrogel matrices are modifiable, their inherent isotropic structure limits the control over cellular organization that is critical to restore tissue function.

Previous studies have primarily focused on exploring the mechanical and biochemical versatility of hydrogels and elucidating their impact on cellular activities (Engler et al., 2006; Discher et al., 2005; Lutolf et al., 2003; Dalsin et al., 2003; Martino et al., 2009). A lack of methodologies exists, however, for engineering anisotropic topographical cues in hydrogels to control the 3D spatial patterns of encapsulated cells. As a result, controlling topographically induced cell alignment and migration has not been readily achieved for hydrogel matrices, even though such cellular manipulation on 2D substrates has been shown to be important in controlling cell organization, tissue microarchitecture, and biological function (Yang et al., 2005; Bettinger et al., 2009; Chew et al., 2008; Aubin et al., 2010).

Recently, Kang et al. reported a microfluidic-based alginate hydrogel microfiber with a surface alignment feature produced by solution extrusion through a grooved round channel, and demonstrated guided neurite outgrowth for neurons cultured on the surface of the microfibers (Kang et al., 2011). This alignment cue, however, is only confined to the surface of the microfibers. Zhang et al. have generated peptide nanofiber hydrogels with long-range nanofiber alignment through heat-assisted self-assembly of amphiphilic peptide molecules and mechanical shear (Zhang et al., 2010). Although the resulting aligned nanofiber "noodles" effectively induced cellular alignment in 3D, this method is only applicable to specific peptide materials.

On the other hand, cellular alignment mediated by 2D electrospun nanofiber matrices has been shown to effectively promote stem cell differentiation and cellular functions (Lim and Mao, 2009; Ji et al., 2006). Although dispersing solid polymer nanofibers into the hydrogel matrix has been used to generate a composite scaffold (Coburn et al., 2011), controlling alignment of the nanofibers inside a hydrogel matrix is challenging.

The development of artificial microvascular vessels is of critical importance in the fields of cardiovascular diseases, cancer growth, and tissue engineering of vascularized organs. In tissue engineering, there is currently a limit on the size of tissues that can be constructed in vitro due to the diffusion limit of nutrients into developing organs. As such, only thin tissues like skin grafts or avascular tissues like cartilage can be successfully engineered in vitro, with larger constructs requiring the existence of a vascular network within itself to supply the necessary nutrients for cell survival and to avoid necrotic areas post-implantation (Huang, G. Y., et al., *Biofabrication*, 2011. 3(1):012001, and Auger, F. A., et al., *Annual Rev Biomed Engineering*, 2013. 15(1):177-200. Development of functional microvascular vessels requires complex interactions between endothelial cells (ECs), perivascular cells, and the extracellular matrix (ECM) (Jain R K, *Nat Med*, 2003; 9: 685-693; Carmeliet P and Jain R K, *Nature*, 2000; 407: 249-257). The ECM is comprised of an abundance of nanometer sized macromolecular ECM proteins. As such, many of the physical interactions between vascular cells and macromolecular components of the ECM occur at the sub-micron scale. EC adhesion to the ECM initiates the angiogenic cascade (Hynes R O, *J. Thromb Haemost*, 2007; 5: 32-40). Cells detect and respond to the nanoarchitecture of their microenvironment by cytoskeletal reorganization and activated signaling cascades to regulate fundamental cell behaviors. Indeed, it has been shown that surfaces with nano-scale line-grating features affect EC adhesion, alignment, and elongation (Ranjan A, and Webster T, *Nanotechnology*, 2009; 20: 305102; Liliensiek S, et al., *Biomaterials*, 2010; 31: 5418-5426; Bettinger C J, et al., *Adv Mater*, 2008; 20: 99-103; Lu J, et al., *Acta Biomater*, 2008; 4: 192-201).

Arterioles are the blood vessels found immediately before capillaries, ranging from tens to hundreds of microns in diameter. ECs, sitting on their basal lamina, comprise the innermost lining of the vessels, this layer containing mainly collagen type IV (Col IV), fibronectin (Fn), laminin (Lmn), and heparin sulfate proteoglycan (Roy, S., et al., *Current Eye Research*, 2010; 35(12):1045-1056). This is followed by a layer of subendothelial connective tissue and an internal elastic lamina (Hibbs, R. G., et al., Am Heart J, 1958; 56(5):662-670; Yen, A. and I. M. Braverman, *J Investig Dermatol*, 1976; 66(3):131-142; Weber, K. and O. Braun-Falco, *Archiv für dermatologische Forschung*, 1973; 248 (1):29-44), which are composed of different ECM proteins, mainly of collagens such as type I and III (Col I, Col III), and elastin (Eln) (Yen, A. *J Investig Dermatol*, 1976; Tsamis, A., et al., *J Royal Society Interface*, 2013; 10(83):20121004. These layers together make the tunica intima of blood vessels. Mural cells, along with their ECM, make up the tunica media (or middle layer), a layer of perivascular cells increasing in thickness with vessel size (Yen, A. *J Investig Dermatol*, 1976; Marieb, E. N. and K. Hoehn, *Human anatomy & physiology*. 2007: Pearson Education; Standring, S., *Gray's anatomy*. The anatomical basis of clinical practice, 2008. 39), and provide the contractility necessary for vasoreactivity. In the smallest of arterioles, the perivascular cells are pericytes, which increase in confluency with vessels size and eventually are replaced by vascular smooth muscle cells (vSMCs) (Yen, A. *J Investig Dermatol*, 1976; Weber, K., 1973; Marieb, E. N. and K. Hoehn, 2007: Pearson Education; Standring, S., *Gray's anatomy*, 2008:39). The tunica media in arterioles has a primarily circumferential orientation of the vSMCs, which is necessary for vasoconstriction. Opposite to arterioles, venules collect blood from the capillary beds and are also supported by perivascular cells, though here the tunica media does not follow a circumferential organization and the ECM layers are less robust than in arterioles ((Hibbs, R. G., et al., Am Heart J, 1958; Yen, A. and I. M. Braverman, *J Investig Dermatol*, 1976; Marieb, E. N. and K. Hoehn, 2007: Pearson Education; Standring, S., *Gray's anatomy*, 2008:39; Jain, R. K., *Nature medicine*, 2003; 9(6): p. 685-693). On top of the tunica media layer lays the tunica adventitia, though it is only present in larger blood vessels (Carmeliet P and Jain R K, *Nature*, 2000; 407: 249-257; Bruce Alberts A J, et al., *Molecular Biology of the Cell*, 2002, New York: Garland Science; Jain R K, *Nature Medicine*, 2003; 9: 685-693; Schwartz S M, and Benditt E P, American J Pathology, 1972; 66: 241; Schriefl A J, et al., *Journal of The Royal Society Interface*, 2012; 9: 1275-1286; Tsamis A, et al., *Journal of The Royal Society Interface*; 2013; 10; Canham, P B, et al., Cardiovascular 1989; 23: 973-982; Finlay H, et al., *Journal of vascular research;* 1995; 32: 301-312; Movat H Z, et al., *Experimental and Molecular Pathology*, 1963; 2: 549-563). The specific composition as well as the organization and arrangement of both cellular and ECM components in each layer are necessary for proper microvasculature development, maturation, stability, and function (Jain R K, *Nat Med*, 2003; 9: 685-693; Carmeliet P and Jain R K, *Nature*, 2000; 407: 249-257).

It has been shown that in microvasculature EC nuclei and cytoskeleton are aligned in the direction of blood flow. However, studies on microvasculature have not analyzed the organization of different ECM components in detail (Movat H Z, and Fernando N V P, *Experimental and Molecular Pathology*, 1963; 2: 549-563; Hibbs R G, et al., *American Heart Journal*, 1958; 56: 662-670; Fernando N V, and Movat H Z, *Experimental and Molecular Pathology*, 1964; 3: 1-9). The literature that has studied the particular organization of the ECM in native blood vessels is focused on analyzing the elastin and collagen structures in the aorta and other large arteries (Schwartz S M, and Benditt E P, *American J Patholo*, 1972; 66: 241; Schriefl A J, et al., *Journal of The Royal Society Interface*, 2012; 9: 1275-1286; Tsamis A, et al., *Journal of The Royal Society Interface;* 2013; 10; Canham, P B, et al., Cardiovascular, 1989; 23: 973-982; Finlay H, et al., *Journal of vascular research*, 1995; 32: 301-312; Halloran B G, et al., *Journal of Surgical Research*, 1995; 59: 17-22). These studies have shown that the structural organization of collagen varies not only between the three layers of the vasculature, but also varies with vessel size and specific location in the body (Tsamis A, et al., *Journal of The Royal Society Interface*, 2013; 10).

Overall, the studies agree that each tunica possesses at least two different families of collagen fibrils, with distinctly different organizations. The general arrangement has been found to be close to axial in the adventitia, outer layers having a more pronounced axial orientation transitioning to a circumferential alignment in inner layers (Finlay H, et al., *Journal of vascular research*, 1995; 32: 301-312). In contrast, the medial layer has been shown to have a nearly perfect circumferential order (Schriefl A J, et al., *Journal of The Royal Society Interface*, 2012; 9: 1275-1286; Tsamis A, et al., *Journal of The Royal Society Interface;* 2013; 10; Canham, P B, et al., Cardiovascular, 1989; 23: 973-982; Finlay H, et al., *Journal of vascular research*, 1995; 32: 301-312). Studies also agree both the internal and external elastic lamina are fenestrated, though both axial and circumferential organization of these layers has been reported (Movat H Z, and Fernando N V P, *Experimental and Molecular Pathology*, 1963; 2: 549-563; Moore D H, and Ruska H, *J Biophysical and Biochemical Cytology*, 1957; 3: 457-462). On the other hand, the subendothelium has been found to have a more varied composition. It has been described as a multilayered fabric of collagen, containing distinct layers of both longitudinally and circumferentially aligned fibers (Schwartz S M, and Benditt E P, *American J Pathology*, 1972; 66: 241; Canham, P B, et al., *Cardiovascular,* 1989; 23: 973-982; Finlay H, et al., *Journal of vascular research*, 1995; 32: 301-312; Gasser T C, et al., *J Royal Society Interface*, 2006; 3: 15-35); some studies suggesting a layer of longitudinally aligned ECM directly under the media layer, followed by a helically arranged region of connective tissue beneath, and a thin circumferentially aligned layer next to the lumen (Finlay H, et al., *Journal of vascular research*, 1995; 32: 301-312). However, these findings were all made on large arteries with diameters in the millimeter range.

The creation of clinically relevant functional microvascular conduits (i.e. arterioles and venules) remains a challenge. To date, only a few studies have attempted to model or recreate microvasculature in a full 3D setting in vitro (Miller J S, et al., *Nat Mater,* 2012; 11: 768-774; Zheng Y, et al., *PNAS USA,* 2012; 109: 9342-9347; Neumann T, et al., *Microvascular Research*, 2003; 66: 59-67; Norotte, C., et al., *Biomaterials,* 2009; 30 (30): p. 5910-5917), though none has achieved a fully functional microvascular structure recapitulating both the cellular and ECM protein organization in the multilayer formation present in native vasculature. The majority of models have either focused on the development of capillary beds in natural or synthetic hydrogels (Yee D, et al., *Tissue Engineering Part A*, 2011; 1351-1361; Hanjaya-Putra D, et al., *J Cellular Molecular Medicine*, 2010; 14: 2436-2447; Meyer G T, et al., *Anat. Rec.,* 1997; 249: 327-340; Bayless K J, Davis G E, *J Cell Science*, 2002; 115: 1123-1136; Bayless K J, *American J Pathology*, 2000; 156: 1673-1683; Grant D S, et al., *Cell Press,* 1989; 933-943; Sacharidou A, et al., *Cells Tissues Organs,* 2011; 195: 122-143; Davis G E, and Camarillo C W, *Experimental Cell Research* 1996; 224: 39-51; Kim D J, et al., *Blood,* 2013; 121(17):3521-30; Hanjaya-Putra D, et al., *Blood,* 2011; 118: 804-815; Lutolf M, and Hubbell J, *Nature biotechnology,* 2005; 23: 47-55; Moon J J, et al., *Biomaterials*, 2010; 31: 3840-3847), decellularized matrices (Hielscher A C, et al., *American Journal of Physiology—Cell Physiology,* 2012; 302: C1243-C1256; Soucy P A, and Romer L H, *Matrix Biology,* 2009; 28: 273-283), and electrospun polymer scaffolds (Pham Q P, et al., *Tissue Eng,* 2006; 12: 1197-1211; Kumbar S G, et al., *Biomed Mater,* 2008; 3: 034002), or have instead aimed to create vascular grafts typically >3 mm in diameter (Aper T, Schmidt et al., *European Journal of Vascular and Endovascular Surgery,* 2007; 33: 33-39; Gui L, *Tissue engineering Part A,* 2009; 15: 2665-2676; Swartz D D, et al., *American Journal of Physiology-Heart and Circulatory Physiology,* 2005; 288: H1451-H1460; Kaushal S, et al., *Nature medicine*, 2001; 7: 1035-1040; Cho S-W, et al., *Annals of surgery*, 2005; 241: 506; L'heureux N, et al., *The FASEB Journal,* 1998; 12: 47-56). While these models enabled study of the ECM-driven molecular mechanisms that regulate EC tubulogenesis, they mostly support spontaneous and random tubulogenesis (size, shape, organization, etc.). Recent work employs micro-patterning and demonstrates an organized vascular network structure within hydrogels, some of which are able to recruit vascular smooth muscle cells (vSMCs) (Baranski J D, et al., *Proc Natl Acad*

Sci USA, 2013; Miller J S, et al., *Nat Mater*, 2012; 11: 768-774; Zheng Y, et al., *Proc Natl Acad Sci USA*, 2012; 109: 9342-9347). Nonetheless, these systems have limited control over topographical cues presented by the ECM and impart a barrier for the high-resolution, dynamic, and detailed study of vascular organization as well as specific cell-ECM and multi-cellular interactions.

Tubular polymeric scaffolds have the potential to provide a better and more sophisticated platform to study the microvasculature, but currently are obtainable with diameters in the millimeter range (Melchiorri A J, et al., *Tissue Eng Part B Rev*, 2012; Fioretta E S, et al., *Macromol Biosci*, 2012; 12: 577-590; Gui L, et al., *Tissue Eng Part A*, 2009; 15: 2665-2676) and are mostly used to study graft's mechanical strength (Wu W, et al., *Nat Med*, 2012; 18: 1148-1153; Huynh T, and Tranquillo R, *Annals of Biomedical Engineering*, 2010; 38: 2226-2236; Lee K-W, et al., *PNAS*, 2011; 108: 2705-2710). To recapitulate the microvasculature in vitro, which has not previously been obtainable, the tubular scaffolds must exhibit a physiologically-relevant diameter and sub-micron topography with sufficient mechanical properties, be biocompatible, mediate specific cell adhesion, allow tubular vessel formation, and, support multi-cellular interactions, thus generating microvessels that mimic natural structure and properties.

Endothelial colony forming cells (ECFCs), a subpopulation of endothelial progenitor cells, are known for their proliferative capacity and contribution to functional vessels (Critser P J, and Yoder M C, *Curr Opin Organ Transplant*, 2010; 15: 68-72; Yoder M C, *J of Thrombosis and Haemostasis*, 2009; 7: 49-52; Yoder M C, et al., *Blood*, 2007; 109: 1801-1809). Recently, we revealed that ECFCs deposit ECM proteins, namely collagen IV, fibronectin and laminin, and also assemble ECM into web-like structures when cultured on Petri dishes (Kusuma S, et al., *FASEB J*, 2012; 26: 4925-4936). This finding suggests an important role for ECM production by ECFCs in the process of vascular assembly that has not yet been identified.

The cellular and ECM composition, as well as their specific structural organization, varies greatly in blood vessels of different type, size, and function. While postcapillary venules (10-30 µm) are formed by ECs and their basal lamina, along with scattered pericytes, and are semipermeable like capillaries (Standring S, 2008, Gray's anatomy), larger venules (larger than 50 µm in diameter) have a muscle layer and a thin adventitia (Standring S, 2008). Both arterioles of 100 µm to 300 µm in diameter and muscular arteries (300 µm to 1 cm) have an aligned endothelium sitting on its basal lamina, surrounded by a layer of connective tissue. This layer is followed by a well-defined fenestrated internal elastic membrane (with ECM occupying void spaces in the fenestrae) and a developed tunica media composed of several layers of circumferentially oriented vSMCs and ECM (mainly collagenous and elastic fibrils). These arteries are the main vessels in charge of restricting blood flow to capillary beds via vSMC constriction in response to neural or chemical stimuli (Standring S, 2008; Marieb E, Hoehn K, *Human Anatomy & Physiology* (8 ed., 2010), Boston, Mass.: Pearson Benjamin Cummings). Even though the ECM is known to be circumferentially oriented in the tunica media, the specific alignment of each layer in the tunica intima remains unclear; several studies report a mix of circumferential orientation close to the lumen and axial orientation close to the media (Schwartz S M, and Benditt E P, *American J Pathology*, 1972; 66: 241-264; Schriefl A J, et al., *Journal of The Royal Society Interface*, 2012; 9: 1275-1286; Tsamis A, et al., *Journal of The Royal Society Interface;* 2013; Movat H Z, et al., *Experimental and Molecular Pathology*, 1963; 2: 549-563; Fernando N V, and Movat H Z, *Experimental and Molecular Pathology*, 1964; 3: 1-9). However, it is known that circumferentially aligned ECM is necessary for vessels to be able to withstand the circumferential stress resulting from the distending pressure of blood flow. These facts highlight the importance of having both circumferential alignment of ECM and several layers of vSMCs, an aspect not found in current microvasculature models. Furthermore, the organization of other ECM components, such as fibronectin and laminin, remains widely uninvestigated. There is a need for a model to study the microvasculature that recapitulates endothelial cell and perivascular cell alignment and ECM deposition for generating microvessels.

SUMMARY

In some aspects, the presently disclosed subject matter provides a method for preparing a microfiber having a uniaxial alignment, the method comprising: (a) providing at least one starting solution comprising one or more polymers; (b) applying an electrical potential to the at least one starting solution sufficient to initiate a jet stream of polymer solution; and mechanically stretching the jet stream of polymer solution during or after collecting the jet stream of polymer solution in a collection bath comprising a stabilizing solution, wherein the collection bath is positioned at a separation distance such that the jet stream of polymer solution is collected before it is accelerated by an electrical field created by the applied electrical potential.

In other aspects, the presently disclosed subject matter provides a microfiber prepared by the presently disclosed methods.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

Another embodiment of the present invention is a three-dimensional (3D) fibrin microfiber scaffold for a novel in vitro model of the microvasculature that recapitulates endothelial cell alignment and ECM deposition. The microfiber scaffold allows the sequential co-culture of endothelial cells and other cells, such as perivascular cells. This model establishes that the fiber curvature affects the circumferential deposition of ECM from endothelial cells independently of cellular organization. The invention further presents a multicellular microvascular structure with an organized endothelium and multicellular perivascular tunica media. The present invention provides unique opportunities to assess microvasculature development and regeneration.

Another embodiment of the present invention relates to a tubular polymeric scaffold, for example a polymer hydrogel microfiber, comprised of electrostretched polymer nanofibers. The polymer preferably is alginate, fibrin (fibrinogen), gelatin, hyaluronic acid, or combinations thereof. More preferably, the polymer is fibrin. An electrostretched polymer microfiber serves as a template for the step-wise creation of microvasculature in vitro.

An embodiment of the invention relates to an electrostretched polymer microfiber that has uniform and tunable diameter, while preserving an aligned internal and external nanotopography. The polymer preferably is alginate, fibrin (fibrinogen), gelatin, hyaluronic acid, or combinations thereof. In a particular embodiment, the polymer is fibrin. Preferably, the polymer microfiber has a diameter of about 500 μm or less, more preferably from about 100 μm to about 450 μm.

In an embodiment of the invention, the electrostretched polymer microfiber generates a micro-cylindrical fiber with a line grating nanotopography. The microfiber enables both endothelial layer organization and co-culture with a second cell type, for example supporting mural cells (perivascular cells).

In some embodiments, the invention relates to a polymer microfiber seeded with endothelial progenitor cells, such as an endothelial colony forming cells. The endothelial cells adhere to the surface of the fibrin microfiber, and align longitudinally with the polymer microfiber. The attached endothelial cells deposit extracellular matrix (ECM) circumferentially organized depending on the size of the microfiber. The extracellular matrix is composed of proteins that encircle (wrap around) the microfiber along the fiber circumference, perpendicular to the cell orientation. In embodiments, the extracellular matrix proteins may be laminin, collagen IV, and/or fibronectin.

Other embodiments relate to endothelial colony forming cells on polymer microfibers that deposit extracellular matrix proteins. The extracellular matrix proteins include, for example, laminin, collagen IV, and fibronectin. The extracellular matrix proteins wrap around the polymer microfiber, perpendicular to the cell orientation, along the fiber's circumference. Further, the extracellular matrix proteins can be above, among, or below the endothelial cells (between the cells and the microfiber).

Embodiments of the invention relate to the polymer microfibers cultured with endothelial progenitor cells being further seeded with a second cell type, such as mural cells (perivascular cells). Preferably, the mural cells are vascular smooth muscle cells or pericytes. In one embodiment, the vascular smooth muscle cells deposit ECM proteins, for example collagen type I, collagen type III and/or elastin. Embodiments include the ECM proteins, for example collagen types I and III, and. elastin, located beneath the vascular smooth muscle cell layer and above the endothelial progenitor cell layer. In another embodiment, pericytes deposit ECM proteins, for example collagen types III and IV. The collagen type IV is located above the endothelial progenitor cell layer.

Other embodiments of the invention are microvascular structures including an electrostretched polymer microfiber seeded with endothelial progenitor cells. Endothelial progenitor cells, such as endothelial colony forming cells, adhere to the surface of the polymer microfiber, align longitudinally with the microfiber, and deposit extracellular matrix circumferentially organized. Extracellular matrix proteins, including for example, laminin, collagen IV, and fibronectin, can encircle the polymer microfiber. The extracellular matrix proteins are oriented perpendicular to the cell orientation, along the fiber's circumference. Further, the extracellular matrix proteins are above, below, or among the endothelial cells. The term "below the endothelial cells" means that the ECM protein is between the cells and the microfiber. In some embodiments the microvascular structure comprising an electrostretched polymer microfiber seeded with endothelial progenitor cells is further seeded with a second cell type, for example mural cells. Preferably, the mural cells are vascular smooth muscle cells or pericytes. In some embodiments, the vascular smooth muscle cells deposits ECM proteins, for example collagens type I and type III, fibronectin, laminin, and elastin. Embodiments include the ECM proteins, for example collagen type I, type III and elastin located beneath the vascular smooth muscle cell layer and above the endothelial progenitor cell layer. In other embodiments, pericytes deposit ECM proteins, for example collagen types I, III and IV, fibronectin and laminin. The collagen type IV is located above the endothelial progenitor cell layer.

In further embodiments of the invention, the polymer microfiber induces increased deposition of ECM proteins by endothelial progenitor cells compared to two-dimensional cultures. These ECM proteins include for example, fibronectin, laminin, and/or collagen IV. The polymer microfibers also induce increased deposition of ECM proteins by perivascular cells seeded on the microfiber. The perivascular cells preferably are vascular smooth muscle cells and/or pericytes. The perivascular cells deposit increased ECM proteins including for example, collagens type I, III and IV, fibronectin, laminin or elastin. In embodiments, the increased ECM proteins deposited include fibronectin, laminin, elastin, and collagens type I, III, and IV.

Another embodiment includes a luminal multicellular microvascular structure. The luminal multicellular microvascular structure is formed from an electrostretched polymer microfiber seeded with endothelial progenitor cells and a second cell type, for example perivascular (mural) cells, wherein the polymer microfiber is degraded after attachment of the cells and deposition of the extracellular matrix. The polymer microfiber may be degraded with an enzyme, such as plasmin. Preferably, the endothelial progenitor cell is an endothelial colony forming cell, and the perivascular cell is a vascular smooth muscle cell or pericyte. In another embodiment, the luminal multicellular microvascular structure is hollow.

In the embodiments of the invention, the polymer is selected from alginate, fibrin (fibrinogen), gelatin, hyaluronic acid, or combinations thereof. In particular embodiments, the polymer is fibrin. In the embodiments, endothelial progenitor cells are endothelial colony forming cells, and the perivascular cells are vascular smooth muscle cells or pericytes. Endothelial colony forming cells deposit ECM proteins such as fibronectin, laminin, or collagen type IV. Vascular smooth muscle cells deposit ECM proteins such as collagen types I, III, IV, laminin, elastin and fibronectin. Pericytes deposit ECM proteins such as collagen types I, III, IV, laminin, and fibronectin.

Embodiments of the invention include a method of sequentially controlling microvascular vessel formation comprising the steps of preparing a tubular polymeric scaffold, for example a polymeric hydrogel microfiber comprising electrostretched polymer microfibers; seeding the microfiber with endothelial progenitor cells; co-culturing the endothelial cell-seeded microfiber with a second cell type such as perivascular (mural) cells, and varying the growth factors used for each step. The endothelial cells deposit extracellular matrix that produces extracellular proteins that encircle the microfiber, and are oriented perpendicular to the cell orientation, along the fiber's circumference, wherein formation of microvasculature vessel is sequentially controlled. In a preferred embodiment, the polymer is alginate, fibrin (fibrinogen), gelatin, hyaluronic acid, or combinations thereof. In a particular embodiment, the polymer is fibrin. In a preferred embodiment, the endothelial progenitor cells are endothelial colony forming cells and the perivascular cells are vascular smooth muscle cells or pericytes. In another embodiment, the method further comprises degrading the microfiber after seeding and culture of cells and deposition of extracellular matrix. Degrading the microfiber may be with an enzyme, such as plasmin.

Another embodiment includes a system for sequentially controlling microvascular vessel formation comprising a tubular polymeric microfiber comprising electrostretched polymer microfibers for forming a matrix for the culture of cells that form the vasculature; endothelial progenitor cells seeded on the polymer microfiber for forming a vascular lining; and perivascular (mural) cells co-cultured with the endothelial cell-seeded microfiber for forming a mural cell layer, and with endothelial progenitor cells depositing extracellular matrix proteins that encircle the microfiber and are oriented perpendicular to the cell orientation along the fiber circumference, wherein a microvascular structure is formed. In an embodiment, the polymer is alginate, fibrin (fibrinogen), gelatin, hyaluronic acid, or combinations thereof. In a particular embodiment, the polymer is fibrin. In a preferred embodiment, the endothelial progenitor cells are endothelial colony forming cells and the perivascular cells are vascular smooth muscle cells or pericytes.

One embodiment of the present invention is a microfiber having a longitudinally aligned nanotopography comprising biodegradable, electrostretched hydrogel polymer nanofibers with internal polymer alignment. The microfibers of the present invention are preferably biodegradable. A biodegradable microfiber of the present invention will not include chemicals or compounds that inhibit the biodegradable nature of the microfiber. Examples of chemicals or compounds that inhibit the biodegradable nature of microfibers include ceramics. Nanofibers of the present invention may be substantially free of such ceramics including zirconia, silica ($SiO_2$), quartz, sapphire, diamond, $Y_2O_3$, $Al_2O_3$, CaO, MgO, $TiO_2$, $P_2O_5$, $CaF_2$, $B_2O_3$, and $Na_2O$ as examples. Microfiber may comprise nanofibers that are parallel to each other that are typically in the form of a solid bundle or a sheet. A microfiber comprising a solid bundle of nanofibers has a diameter in the range of 0.1 to 100 nm. A sheet of nanofibers maybe shaped to form a circumference so that a microfiber of the present invention is hollow or comprises a conduit in the range of 20 micrometers to 20 mm. Microfibers of the present invention may have a diameter in the range from 100 µm to about 500 µm based on the outer circumference of the microfiber. The hydrogel polymer nanofibers of the present may have a water content of greater than 90%, greater than 95%, or greater than 98% of the nanofiber. The nanofibers of the present invention comprise one or more polymers selected from the group consisting of alginate, fibrin (fibrinogen), gelatin, hyaluronic acid, and a combination thereof.

Another embodiment of the present invention are microfibers further comprising endothelial progenitor cells including endothelial colony forming cells, as an example, seeded on the polymer microfiber. The endothelial progenitor cells are aligned longitudinally to the polymer microfiber and endothelial colony forming cells deposit extracellular matrix proteins on the microfibers. The extracellular matrix proteins that are deposited are circumferentially organized, wrapping around the microfiber. Examples of extracellular matrix proteins that are deposited include laminin, collagen IV, and fibronectin, as examples. The collagen IV, laminin, and fibronectin are deposited in higher quantities on the microfiber than on 2D cultures. Other cells may adhere to the microfibers of the present invention. For example, perivascular cells may be seeded, or adhere, on the microfiber. An example of suitable perivascular cells are pericytes. Pericytes deposit extracellular matrix proteins, and the extracellular matrix proteins are longitudinally organized along the microfiber. Another example of perivascular cells are vascular smooth muscle cells. The vascular smooth muscle cells deposit extracellular matrix proteins, and these extracellular matrix proteins are longitudinally, randomly, or circumferentially organized along the microfiber. A second cell type may be seeded or adhere on the microfiber. An example of a second cell type is a mural cell and the mural cell is vascular smooth muscle cell or a pericyte. Microfibers of the present invention may comprise vascular smooth muscle cells or pericytes that is randomly oriented, or is longitudinally oriented with respect to the microfiber. The vascular smooth muscle cell deposits collagen type I and elastin, and the pericyte deposits collagen type IV. These extracellular matrix proteins are induced to circumferentially organize and wrap around the microfiber by the longitudinally aligned nanotopography of the microfiber. Microfiber of the present invention may be substantially free of a chemical that promotes cell alignment include hydrophilic agents such as dextran, polyvinyl alcohol, polyethylene glycol, polyoxyethylene, gelatin, pullan, heparin, hirudin, ticlopidine, and chlopidogrel; and hydrophobic agents such as polyactide, polyactic acid, polyglycolide, polyglycolic acid, polyactide-polyglycolide, polyglycolide, polyglycolic acid, polyactide-polyglycolide, polycaprolactone, and polyamino acid, as examples. The longitudinally aligned nanotopography of a microfiber of the present invention induces cell alignment on the microfiber. A chemical agent that promotes cell alignment in not needed on a microfiber of the present invention in order to produce cell alignment.

Another embodiment of the present invention is a biodegradable, electrostretched hydrogel polymer nanofiber with internal polymer alignment. Nanofibers of the present invention also have a longitudinally aligned nanotopography and similar cell alignment characteristics as the microfibers described above. Cells and proteins align on the nanofibers because of their longitudinally aligned nanotopography Nanofibers of the present invention may be substantially free of a chemical that promotes cell alignment include hydrophilic agents such as dextran, polyvinyl alcohol, polyethylene glycol, polyoxyethylene, gelatin, pullan, heparin, hirudin, ticlopidine, and chlopidogrel; and hydrophobic agents such as polyactide, polyactic acid, polyglycolide, polyglycolic acid, polyactide-polyglycolide, polyglycolide, polyglycolic acid, polyactide-polyglycolide, polycaprolactone, and polyamino acid, as examples. The nanofibers of the present invention are biodegradable and are substantially free of a ceramics as describe above. The hydrogel polymer nanofibers has a water content of greater than about 90%, greater than 95%, or greater than 98%.

BRIEF DESCRIPTION OF THE FIGURES

Figures 1A, 1B, 1C, 1D, 1E, 1F, 1G, 1H, 1I, 1J, 1K, 1L, 1M:
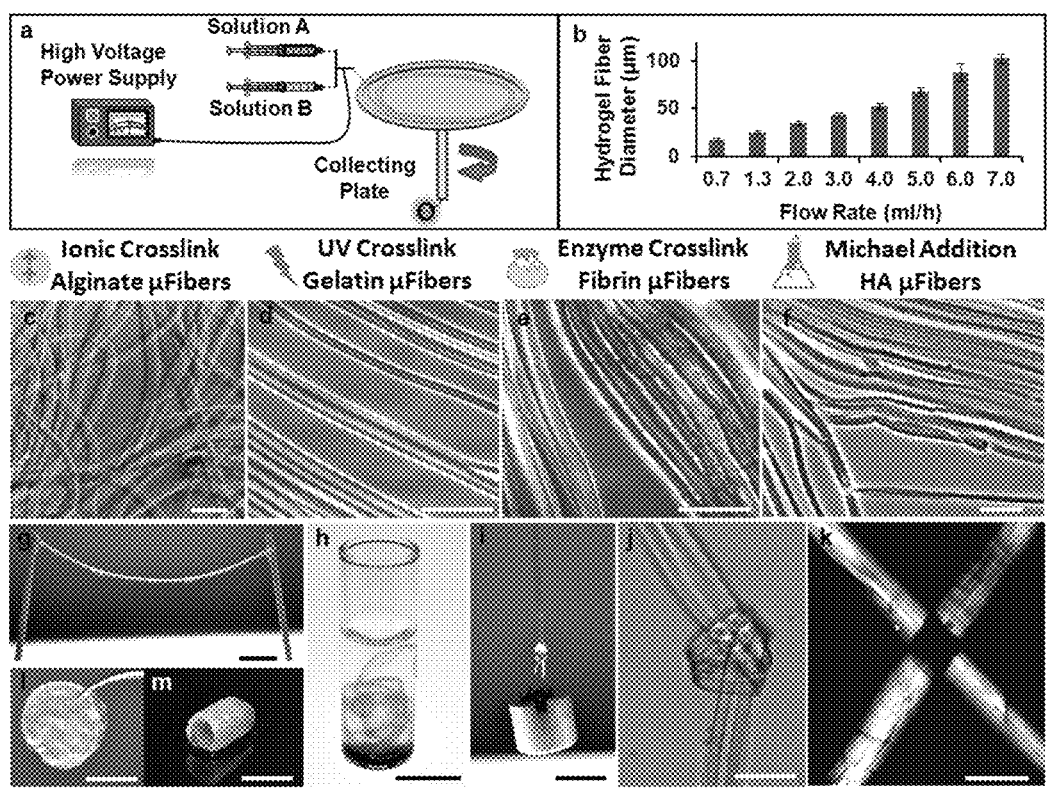
Figure 5:
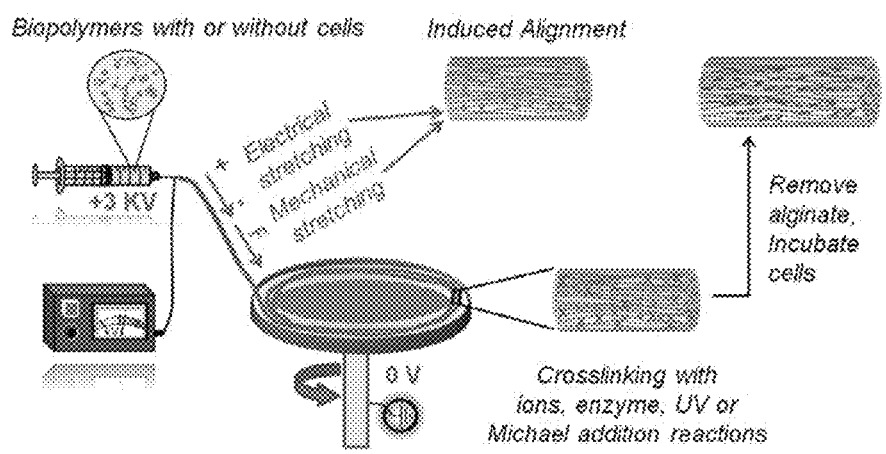
Figure 6:
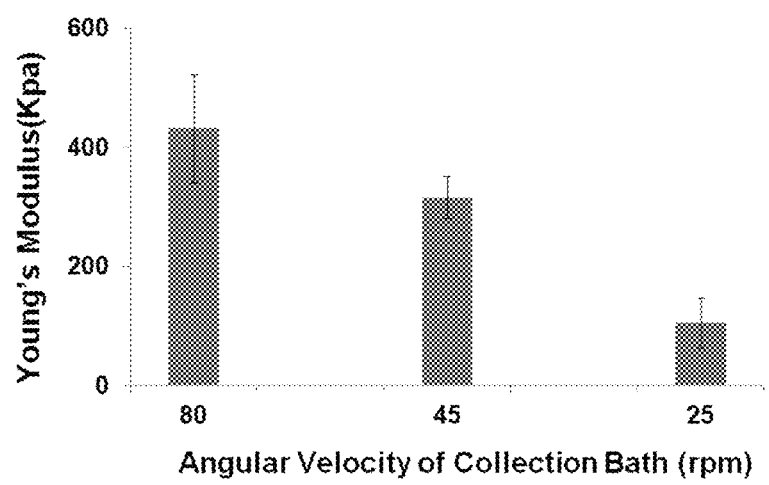

Having thus described the presently disclosed subject matter in general terms, reference will now be made to the accompanying Figures, which are not necessarily drawn to scale, and wherein:

FIGS. 1A-1M show the electrostretching setup and features of the presently disclosed hydrogel microfibers: (a) illustration of a representative spinning setup for electrostretching; (b) effect of alginate solution feeding rate on the diameter of the hydrogel microfibers. Alginate hydrogel microfibers with an average of 17-116 µm were prepared with a solution containing 2% sodium alginate and 0.2% PEG fed at a flow rate ranging from 0.7-7.0 ml/h. Bars represent mean±s.d. (n=3); (c-f) demonstrate that various crosslinking mechanisms have been employed to crosslink alginate, gelatin, fibrin, and hyaluronic acid hydrogel microfibers. The crosslinking of the fibers was initiated with a fast calcium gelation of alginate, followed by additional cross-linking of the second component polymer with UV-initiated, enzymatic, or the Michael addition reaction for methylated gelatin, fibrin and hyaluronic acid, respectively; (g) using this method, hydrogel microfibers of any desired length can be prepared; (h) when dispersed in water, alginate hydrogel fibers formed a loose network of hydrogel fibers. Trypan blue was used to stain the fibers and enhance observation; (i) a 10-g metal weight was lifted with an alginate hydrogel microfiber bundle; (j) a micro-knot was made with two alginate hydrogel microfibers; (f) under a cross polarized light microscope, light extinction was observed at the cross-over point of two hydrogel microfiber bundles, indicating uniform alignment in both fibers; (l-m) beyond microfiber bundles, these hydrogel microfibers also can be fabricated into other forms like fibrous films (l) and self-supporting hydrogel tubes (m). Scale bars represent 100 µm in (c-f), 1 cm in (g-i) and (l-m), 50 µm in (j), and 1 mm in (k);

FIGS. 2A-2I show SEM micrographs of hydrogel fibers prepared with simple extrusion and electrostretching. (a-c) Fibrin (a), gelatin (b) and HA (c) hydrogels prepared by simple extrusion or mixing consist of randomly oriented nanofiber network. (d-f) Electrostretched fibrin (d), gelatin (e) and HA (f) hydrogel fibers showing preferential alignment. Arrows indicate the orientation of the microfiber longitudinal axis. (g-i) Fibrin (g), gelatin (h) and HA (i) hydrogel fibers following stretching and dehydration in air forming fiber bundles. Both fibrin and gelatin fibers preserved surface texture and grooves. Samples in (a-f) were prepared by the critical point drying technique; and samples in (g-i) were stretched and dried in air. Scale bars represent 1 µm in (a-b) and (d-e), 2 µm in (c) and (f), 20 µm in (g-h), and 40 µm in (i);

FIGS. 3A-3G show X-ray scattering diffraction patterns and tensile moduli of hydrogel fibers in dry and wet states. (a-b) Small angle X-ray scattering (SAXS) patterns of the dry (a) and wet (b) calcium alginate hydrogel fibers confirming an alignment axis along the microfiber orientation indicated by the arrows. (c) SAXS pattern of alginate hydrogel prepared by hand extrusion suggesting an isotropic structure. (d) Wide angle x-ray scattering pattern of the dry alginate microfibers confirming the polymer chain alignment along the fiber axis as indicated by the arrow. (e-g) Tensile moduli of alginate (AG), fibrin (FN), gelatin (GT) and hyaluronic acid (HA) hydrogel fibers in dry (e), wet (f) and re-hydrated form (g). Bars represent mean±s.d. (n=3);

FIGS. 4A-4F show small angle x-ray scattering (SAXS) patterns for fibrin and gelatin hydrogel microfibers: (a-b) SAXS patterns of dry (a) and wet (b) fibrin hydrogel fibers prepared by electrostretching; (c) SAXS pattern for fibrin hydrogel samples prepared by simple extrusion; (d-e) SAXS patterns of dry (d) and wet (e) gelatin hydrogel fibers prepared by electrostretching; and (f) SAXS pattern for gelatin hydrogel samples prepared by simple extrusion;

FIG. 5 shows an illustration of polymer alignment as a result of electrical and mechanical stretching. An aqueous solution of biopolymer(s) with or without cells is spun under electrical and mechanical stretching forces. Polymer chain alignment induced during this process is then quickly fixed with stabilizing solution in the collection bath. Bicomponent or multicomponent hydrogel fibers can be spun similarly by mixing different polymers in the spinning solution, also referred to herein as the starting solution. Additional cross-linking can be performed via enzyme, UV-initiated cross-linking, or cell compatible chemical reactions (e.g. the Michael addition reaction). Cell encapsulation can be achieved by incorporating cells in the spinning solution, forming "cellular strings"; and FIG. 6 shows tensile moduli of wet alginate hydrogel fibers prepared at different collection plate rotation speeds. All fiber samples were crosslinked in 25 mM $CaCl_2$) solution for 4 minutes prior to measurement. Bars represent mean±s.d. (n=3).

FIG. 7A-7E ECFCs attached and aligned on fibrin hydrogel microfibers. (A) Schematic of experimental procedure including electrostretching, ECFC seeding, and tumbling. Drawing not to scale. Scanning electron microscopy (SEM) of critical point-dried fibrin microfiber showing aligned topography on the microfiber surface. Scale bar is 10 µm. (B-D) Confocal Z-stack image reconstructions of ECFCs seeded on fibrin hydrogel microfibers horizontally aligned after 5 days in culture; F-actin (phalloidin staining) is shown in green, EC-specific markers (VECad, CD31, or vWF) in red, and nuclei in blue. Yellow arrows indicate the direction of stretching and nanotopography on microfiber surface. Scale bars are 50 µm. n≥2 per stain with quadruplicates. (E) Confocal Z-stack image reconstructions of ECFCs seeded on fibrin microfibers after one day in culture; F-actin (phalloidin staining) are shown in green, CD31 in red, and nuclei are counterstained in blue. Scale bars are 100 µm.

FIG. 8A-8G ECFCs deposit ECM circumferentially on fibrin hydrogel microfibers. Confocal stack image reconstructions of ECFCs on fibrin microfibers after (A) 1 and (B) 5 days in culture. Scale bars are 200 µm. (C) High magnification confocal images of laminin, fibronectin and collagen IV wrapping around the fibrin microfibers. (D) TEM images of cross-sectional slices of a cell-fibrin microfiber construct after 5 days in culture (i-ii) with cells and (iii) without cells. (ii) is a higher magnification image for the boxed area in (i). F=Fibrin; E=ECM; C=Cells. (E) Cross-sectional projections of confocal Z-stack images of ECFCs on fibrin microfibers after 5 days. F-actin (phalloidin) is shown in green, ECM proteins (collagen IV, laminin, fibronectin) in red or magenta, and nuclei in blue. Yellow arrows indicate the direction of nanotopography on microfiber surface. a-n≥2, b-e n≥5 per stain with quadruplicates. (F) and (G) High magnification confocal Z-stack image reconstructions of ECFCs-seeded fibrin microfibers after 5 days in culture showing (F) wrapping ribbon-like organization of Collagen IV, laminin and fibronectin (in red; Scale bars are 50 µm) and (G) horizontal orientation of ECFCs with circumferential organization of the deposited Collagen IV (red). Yellow arrow indicates the direction of nanotopography. Scale bars are 100 µm.

FIG. 9A-G Nanotopography and geometry differently effect ECM organization. Confocal Z-stack image reconstructions of (A) ECFCs on 2D fibrin sheets after 5 days in culture. Yellow arrows indicate the direction of nanotopography. Scale bars are 50 µm. n=2 with duplicates. (B) ECFCs on PES 3D fibrin-coated fibers with random non-aligned topography after 5 days in culture. Scale bars are 100 n≥4 with quadruplicates. Actin filaments (phalloidin) are shown in green, ECM proteins (collagen IV, laminin, fibronectin) in red, and nuclei in blue. Box-and-whisker plots showing ECFCs (C) and ECM (D) angle of orientation on PES and fibrin hydrogel microfibers after 5 days in culture. (E) Standard deviation of ECM angle of orientation. Error bars represent 5-95% confidence intervals. Significance levels in the mean represented by ***p<0.001. n≥2 with quadruplicates. (F) SEM of critical-point dried fibrin fiber sheets showing aligned topography on the surface. Scale bar is 2 µm. (G) SEM of critical-point dried PES microfibers (i)

coated with fibrin showing random topography and (ii) uncoated showing smooth topography. Scale bars are 10 µm.

Figure 10A:
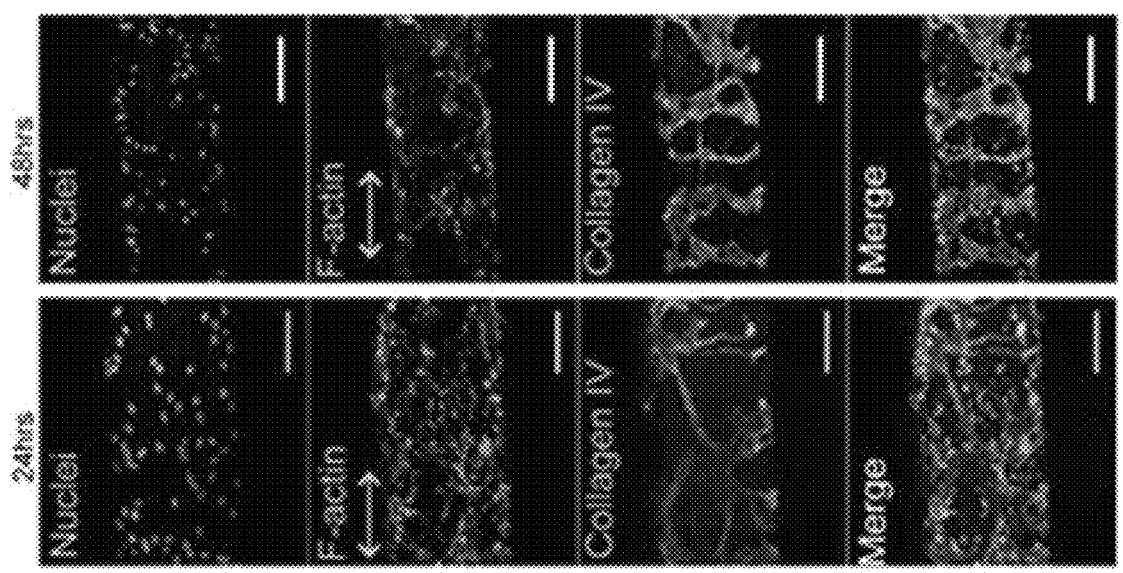

FIG. 10A-N Disrupting actin and microtubule organization does not affect ECM organization. Confocal Z-stack image reconstructions of ECFCs seeded on fibrin microfibers for 24 hrs followed by treatment with (A) cytochalasin D or (B) nocodazole for 24 hrs and 48 hrs in culture. (C) Low (left) and high (right) magnification of ECFCs seeded on fibrin microfibers for 72 hrs without drug treatment, serving as control. F-actin (phalloidin staining) is shown in green, microtubules (α-tubulin) in red, ECM proteins (collagen IV or fibronectin) in red or magenta, and nuclei in blue. Yellow arrows indicate the direction of nanotopography. Scale bars are 100 µm except of high magnification in (C) that is 50 µm. (D) Box-and-whisker plots and (E) standard deviation of ECM angle of orientation. Error bars represent 5-95% confidence intervals. n=2 with quadruplicates. (F)-(H) Confocal Z-stack image reconstructions of ECFCs seeded on (F) fibrin microfibers or (G) on Petri dish for 24 h followed by treatment with cytochalasin D for 48 h in culture. (H) ECFCs seeded on fibrin microfibers and treated immediately with cytochalasin D for 72 hrs of culture. F-Actin filaments (phalloidin) are shown in green, collagen IV in red, fibronectin or laminin in magenta, and nuclei in blue. Yellow arrows indicate the direction of nanotopography on fibrin microfibers. Scale bars are 50 µm in (F)-(G) and 100 µm in (H). (I)-(K) Confocal Z-stack high-magnification image reconstructions of ECFCs seeded on (I) fibrin microfibers or (J) Petri-dishes for 24 h followed by treatment with nocodazole for 48 h of culture. (K) ECFCs seeded on fibrin microfibers and treated immediately with nocodazole for 72 hrs of culture. F-Actin filaments (phalloidin) in green, microtubules (α-tubulin) in red, Collagen IV in magenta, and nuclei in blue. Yellow arrows indicate the direction of nanotopography on fibrin microfibers. Scale bars are 50 µm in (I) (left), (J) (right) and (K) (right); 20 µm in (I) (right); and 100 µm in (K) (left). (L)-(N) Confocal Z-stack image reconstructions at different magnifications of ECFCs-seeded fibrin microfibers after 3 days in culture showing non-confluent ECFCs with circumferential organization of the deposited Collagen IV (red). Yellow arrow indicates the direction of nanotopography. Scale bars are (L) 200 µm, (M) 100 µm, (N) 50 µm.

FIG. 11A-F Microfiber curvature influences ECM organization. (A) Confocal Z-stack image reconstructions of Collagen IV deposition on fibrin microfibers with different diameters. Scale bars are 200 µm (B) Scatter plot and (C) standard deviation of ECM angle of orientation on microfibers with different diameters. Error bars represent 5-95% confidence intervals. Significance levels in the distribution represented by ***p<0.001. n=2 with quadruplicates. (D)-(F) High magnification confocal Z-stack image reconstructions of ECFCs-seeded fibrin microfibers with different diameter after 5 days in culture showing Collagen IV in red. Scale bars are 50 µm. Yellow arrow indicates the direction of nanotopography.

FIG. 12A-G Co-cultured vSMCs deposit new ECM. Confocal Z-stack image reconstructions of fibrin microfibers seeded with ECFCs followed by (A) co-culture of vSMCs for 2 days. n=2 with quadruplicates. Scale bars are 200 µm. Co-cultured vSMCs for 3 days showing (B) wrapping and (C) aligned arrangement. Scale bars are 100 µm. (D) Collagen Type I deposited by co-cultured vSMCs after 3 days in co-culture. Scale bars are 100 µm. (E) Cross-sectional projection of confocal Z-stack images of vSMCs after 5 days in co-culture. Arrowheads indicate SM22⁻ cells. Scale bars are 50 µm. (B)-(E) n≥3 with quadruplicates. (F) Confocal Z-stack image reconstruction and (G) cross-sectional projection of co-cultured vSMCs after 5 days in co-culture. n=2 with quadruplicates. Scale bars are 50 SM22 is shown in green, CD31 in red, collagen I and elastin in red, and nuclei in blue.

FIG. 13A-E Co-cultured Pericytes proliferate and deposit new ECM. Confocal Z-stack image reconstructions of fibrin microfibers seeded with ECFCs and cultured for 5 days followed by co-culture of pericytes for 10 days in ECFC media supplemented with 30 mM aminocaproic acid. (A) Pericytes express SM22 (red) and are located above ECFCs expressing lectin (green). Co-cultured pericytes showing (B) wrapping and (C) aligned arrangement. SM22 shown in green. (D) Projection and (E) cross-sectional projection of confocal Z-stack images of Collagen IV (green) deposited by co-cultured pericytes marked with smooth muscle actin (SMA) (red). Nuclei shown in blue. Arrowheads indicate ECFCs which are SM22⁻ and SMA⁻ (SMA negative) cells. Scale bars are 100 µm in (A) and (C), 50 µm in (B), (D), and (E).

Figure 14A:
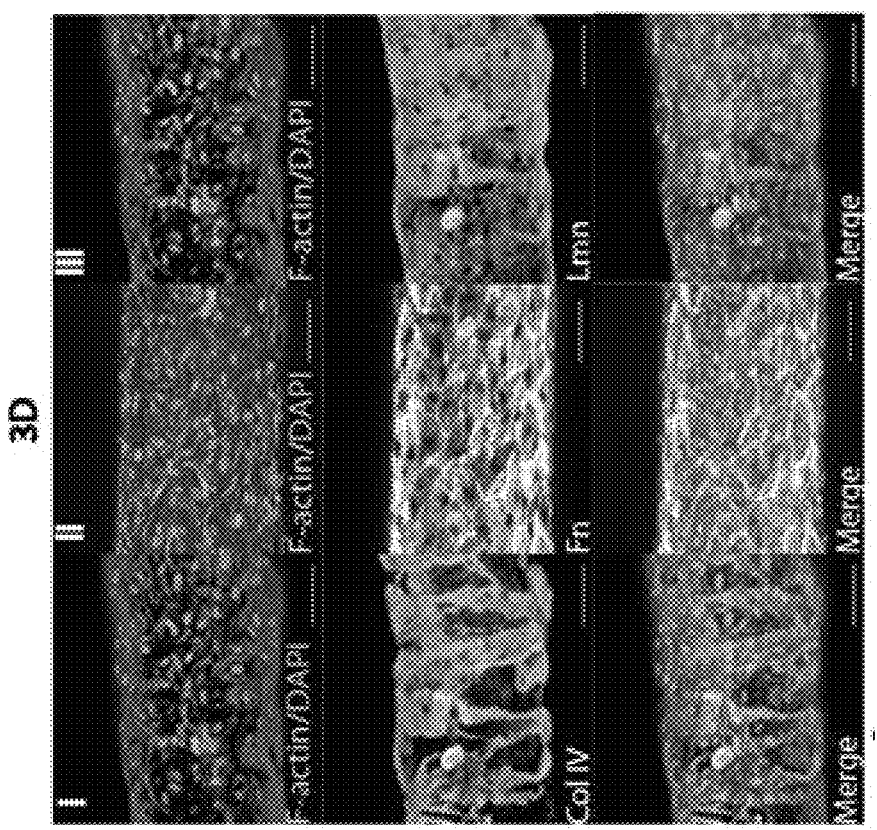
Figure 14B:
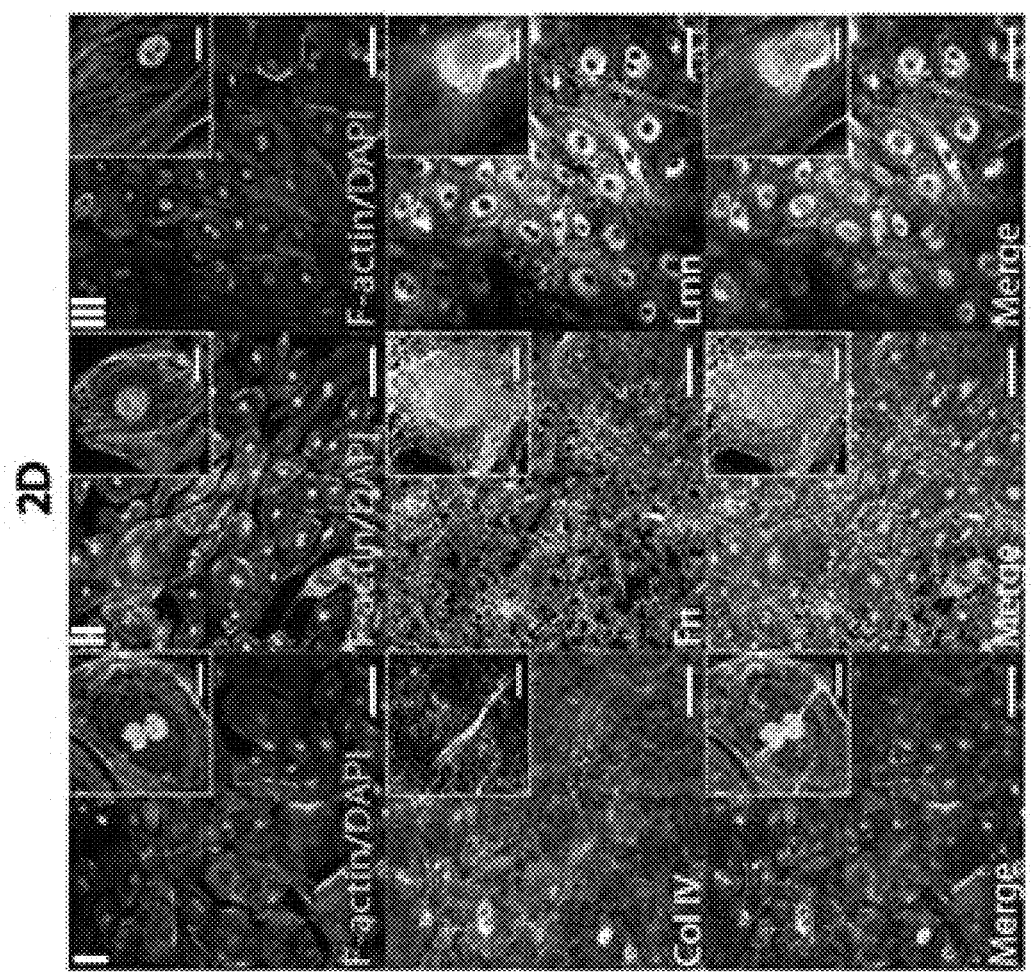
Figure 14C:
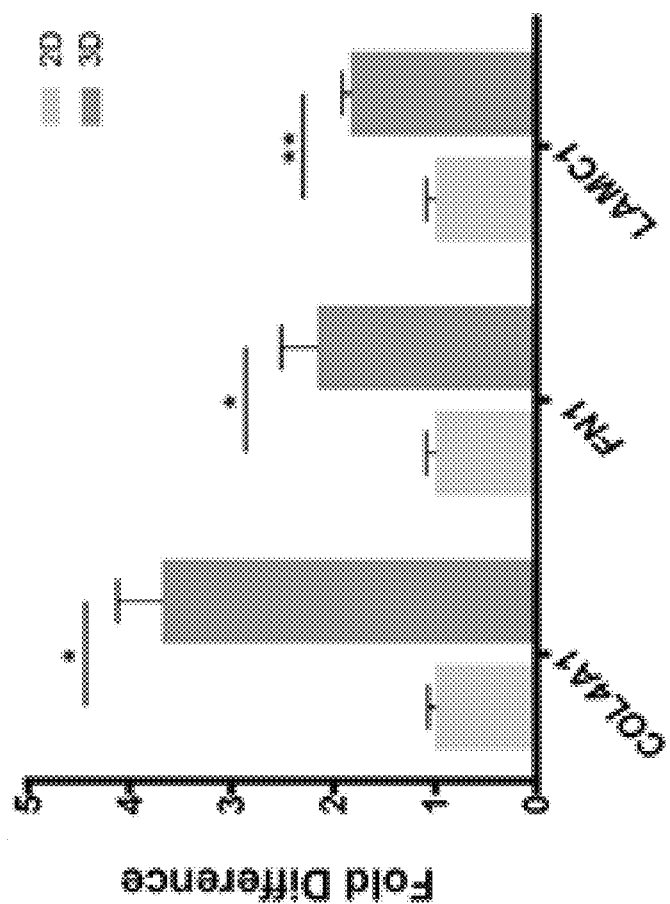

FIG. 14A-C Deposition of Collagen IV (Col IV), fibronectin (Fn), and laminin (Lmn) by ECFCs in 3D vs. 2D. Confocal Z-stack image projections of ECM in (A) 3D fibrin microfibers and (B) 2D fibrin coated surfaces. Red: corresponding ECM; blue: nuclei, green: F-actin. Scale bars=100 µm. Insert scale bars=25 µm. (C) RT-PCR analysis of expression of ECM genes by ECFCs cultured on 2D vs. 3D. Error bars represent SEM. Significance levels in the distribution represented by *p<0.05 and **p<0.01. n≥3.

FIG. 15 A-D Deposition of Col I, III, IV, Fn, and Lmn by pericytes in 3D vs 2D. Confocal Z-stack image projections of ECM in (A) 3D fibrin microfibers and (B) 2D fibrin coated surfaces. Red: corresponding ECM; blue: nuclei, green: F-actin. Scale bars=100 µm. Insert scale bars=25 µm. Arrows, arrowheads, and double-headed arrows point to randomly deposited, non-polymerized, and aligned ECM proteins, respectively. (C) RT-PCR analysis of expression of ECM genes by vSMCs cultured on 2D vs 3D. (D) Orthogonal view of pericytes grown on microfibers. Arrowheads point to cells underneath outer cell layer, arrow points to extracellular deposited Lmn. Scale bar=20 µm. Error bars represent SEM. Significance levels in the distribution represented by *p<0.05 and **p<0.01. n≥3.

FIG. 16A-D Deposition of Col I, III, IV, Eln, Fn, and Lmn by vSMCs in 3D vs 2D. Confocal Z-stack image reconstructions of ECM in (A) 3D fibrin fibers and (B) 2D fibrin coated surfaces. Red: corresponding ECM; blue: nuclei, green: F-actin. Scale bars=100 µm. Insert scale bars=25 µm. Arrows, arrowheads, and double-headed arrows point to randomly deposited, intracellular, and aligned ECM proteins, respectively. (C) RT-PCR analysis of expression of ECM genes by pericytes cultured on 2D vs 3D. ND=not determined. (D) Orthogonal view of pericytes grown on microfibers. Arrowheads point to cells underneath outer cell layer, arrow points to extracellular deposited Lmn. Scale bar=20 µm. Error bars represent SEM. n≥2.

Figure 17A:
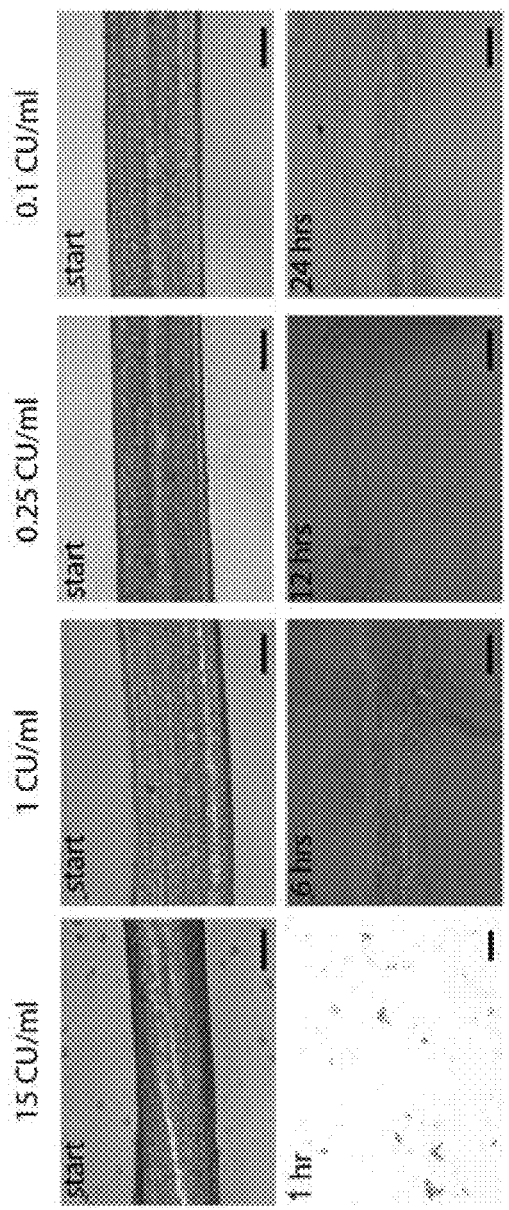
Figure 17B:
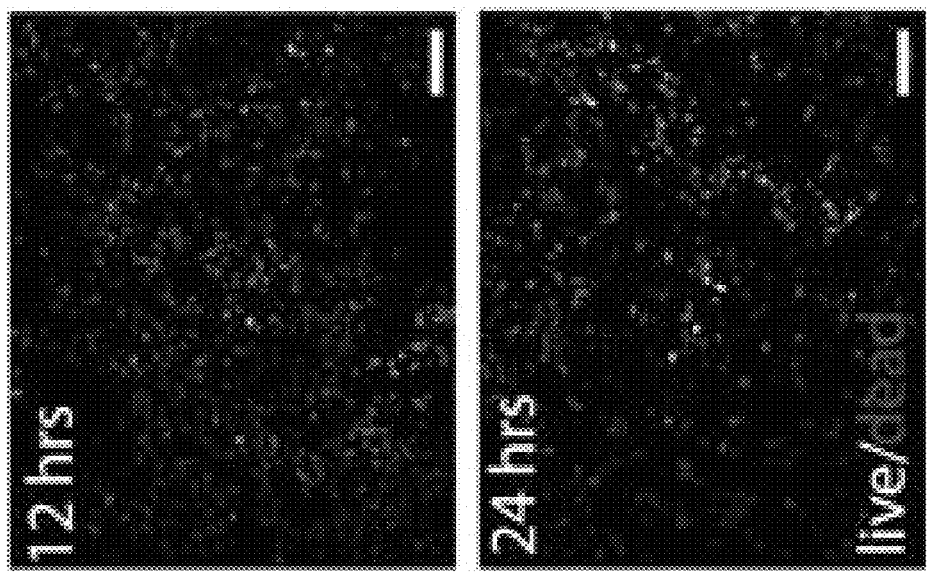

FIG. 17A-C Fiber degradation and viability of cells and ECM after plasmin treatment. (A) Light microscopy images of plasmin degrading fibrin microfibers in a concentration dependent manner. Scale bars=100 µm. (B) Immunofluorescence images of viability assays of ECFCs after 12 and 24 hr treatments with plasmin. Red: dead cells; green: live cells Scale bars=500 µm. (C) Confocal Z-stack image projections of fibrin fibers with ECFCs for 5 days and treated with plasmin for (I) 12 and (II) 24 hrs. (I) Col IV (red) Fn (green) Scale bars=200 µm, insert scale bars=100 µm. (II) Lmn (green) Left panel scale bar=200 μm, right panel scale bar=50 μm. Insert: Cross-sectional image, scale bar=50 μm. n≥2.

FIG. 18A-D ECFC and perivascular cell co-cultures on fibrin microfibers. Confocal Z-stack image projections of ECFCs grown for 5 days on fibrin microfibers followed by 5 days more of (A) pericyte co-culture. Red: (I) VEcad (II) SM22 (III) Col III; blue: nuclei, green: F-actin. (B) vSMC co-culture. Red: (I) VEcad (II) SM22 (III) Eln; blue: nuclei, green: F-actin. Confocal Z-stack image 3D reconstructions of structures cultures for 5 days with ECFC followed by 5 more days with perivascular cells and then treated for 12 hrs with 0.25 CU/mL plasmin. (C) Pericyte co-culture. Red: (I) and (III) VEcad, (II) and (IV) Col III; magenta: (I) and (III) SM22; blue: nuclei; green: (I) and (III) F-actin, (II) and (IV) Col IV. (D) vSMC co-culture. Red: (I) and (III) VEcad, (II) and (IV) Eln; magenta: (I) and (III) SM22, (II) and (IV) Fn; blue: nuclei; green: F-actin. Scale bars=50 μm. n≥2.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides an approach that combines an electrical and mechanical stretching force to generate biopolymer hydrogel microfibers having a high degree of chain alignment within the hydrogel fiber. The presently disclosed methods can be applied to a wide range of polymer hydrogel systems, such as alginate, fibrin, gelatin, collagen, hyaluronic acid, chitosan, and their blends and are applicable to a wide range of biomedical applications.

The presently disclosed subject matter demonstrates that this internal polymer chain alignment affords excellent mechanical properties to these hydrogel fibers. The presently disclosed methods are highly versatile with a high degree of control over fiber diameter and fiber constructs. Further, the presently disclosed fiber spinning process is conducted in aqueous solutions at room temperature and is thus amenable to cell encapsulation within the hydrogel fibers during spinning and gelation.

Further, the presently disclosed subject matter demonstrates that the alignment topography is a strong matrix cue to induce alignment of cells that are seeded either inside the hydrogels or on the hydrogel surface. Due to the excellent cellular responses and the versatility of materials choice, these systems can be useful substrates to create "cellular wires" (e.g., nerve cables) or guide cell migration in wound healing or regeneration.

I. Methods of Preparing Electro-Mechanically Stretched Microfibers

Current electrospinning methods known in the art for producing microfibers rely on electrical force to stretch the fiber into a smaller diameter. In such methods, dried fiber is collected after an accelerated stretching process, during which the speed and amount of jet elongation induced by an applied electrical field is not well controlled. The high stretching rate (e.g., $10^5$ to $10^6$ s$^{-1}$) at the end of such processes also makes known electrospinning techniques unsuitable for treating delicate substances, such as hydrogel, cells, or self-assembled molecules. Further, large fibers, e.g., fibers having a diameter ranging from tens to hundreds of microns, are not easy to make by electrospinning methods known in the art.

A certain level of molecular orientation, however, can be developed via conventional electrospinning processes. Molecular level alignment in these cases is a result of high strain rate commonly used in electrospinning of polymers (e.g., $10^5$ to $10^6$ s$^{-1}$). According to theoretical models, a high degree of uniaxial orientation is expected if the product of strain rate and the conformational relaxation time λ is greater than unity during uniaxial stretching of polymeric melts or solutions. Generally, a high level crystalline structure along the fiber axis is not observed in fibers formed by conventional electrospinning processes because of the rapid solidification of the fluid jet.

In contrast, the presently disclosed methods use a combination of electrical and mechanical force to induce stretching to replace the uncontrollable stretching in electrospinning. More particularly, the presently disclosed methods use an electrical field to initiate and stretch a jet stream of polymer solution and a mechanical force exerted by a rotating collection bath comprising a stabilizing collection solution and a rotating collection plate to control the amount of stretching. In this way, the overall stretching rate can be adjusted by changing the speed of the rotating collection plate and by modifying electric field strength. Fibers produced this way also have a molecular level preferential alignment, which significantly improves their mechanical properties.

Generally, in the presently disclosed methods, a high voltage electrode is contacted with a starting solution to initiate a jet stream of polymer solution through, for example, a syringe needle. The jet stream of polymer solution is collected with a rotating collection plate positioned at a close distance to the tip of the syringe needle before the jet stream of polymer solution is accelerated by an electrical field induced by the high voltage electrode. More particularly, as provided herein above, the electric field initializes the stretching of the polymer stretch, which is due to an acceleration of the jet stream of polymer caused by the applied electrical field. The collection of the jet stream of the polymer solution occurs while the stream is still in a linear trajectory before the chaotic bending instability (whipping) regime that is standard to traditional electrospinning.

During collection, the rotating collection plate further stretches the jet stream of polymer solution so it travels the same distance as the rotating collection plate. Because the mechanical stretching rate is determined by the speed of the rotating collection plate and solution feed rate, the presently disclosed methods can be regulated to process delicate substances or to produce fibers of desired size range (10 to 300 μm), both of which cannot be done with conventional electrospinning methods known in the art.

In the presently disclosed methods, the jet stream of polymer solution is collected in regions where the jet stream is initiated and before it is accelerated into a whipping jet. The overall electromechanical strain rate is estimated to be around 10 to 70 s$^{-1}$, which is several orders of magnitude lower than conventional electrospinning. The relative high molecular weight of natural polymers used in this process, corresponding to a longer relaxation time λ, will be sufficient to facilitate polymer chain alignment under low strain rate, in absence of rapid solidification.

Accordingly, the elongational flow induced by electrical and mechanical stretching force also creates a unique alignment among the individual fibers in the string or film produced. Without wishing to be bound to any one particular theory, it is thought that the synergy of electrical field and mechanical stretching helps to align the fibers. In addition to stretching induced alignment, the electrical field also contributes to the overall alignment of the fibers. The alignment can be fixed, for example by crosslinking the fibers after they are collected. Such alignment not only enhances the mechanical properties of the final matrix, but also brings new capacities for their utility. Polarized optical microscopy and scanning electron microscopy (SEM) have been used to confirm these characteristic structures.

Fibers formed by the presently disclosed can be further elongated with mechanical force along the fiber axis. Application of such mechanical force or stress helps to enhance the alignment of the polymer chains and fix them in a longitudinal direction. Due to their large surface areas, such strings will bundle together if taken out the collection or fixing solution. Applying a constant stretching force until the fibers are dry can lead to a fiber cross sectional area that decreases to approximately 2% of its original cross sectional area. Again, without wishing to be bound to any one particular theory, it is thought that such a dehydration process further improves the alignment inside the string.

Accordingly, in some embodiments, the presently disclosed subject matter provides methods to incorporate anisotropic topography inside a hydrogel matrix using a combination of electrical and mechanical stretching. Such microfibers can be made of natural polymers including, but not limited to, alginate, fibrinogen, gelatin, collagen, hyaluronic acid (HA), chitosan chondroitin sulfate, dextran sulfate, heparin, heparan sulfate, and the like, and functionalized derivatives thereof; synthetic polymers including, but not limited to, polyacrylic acid derivatives, polyvinyl alcohol, and the like.

The presently disclosed methods are versatile and scalable and represent the first approach to enable control over hydrogel alignment topography in polymer hydrogel fibers derived from a variety of biopolymers. Accordingly, the molecules inside microfibers made by the presently disclosed methods are preferentially aligned along the microfiber axis. The unique internal uniaxial alignment characteristic enhances the mechanical properties of the hydrogel microfibers. Microfibers having a size ranging from a few microns to hundreds of microns have been made using the presently disclosed electro-mechanical stretching method. The presently disclosed methods can be used to produce various forms of hydrogel matrices, such as a film, mesh, tube, a single string, or a bundled yarn.

Further, mechanical strain usually generates dense materials through the exclusion of water during the stretching process. In contrast, the presently disclosed methods retain the hydration ratio or water content throughout the spinning process. As a result, hydrogel fibers with a water content of more than 90%, and, in some embodiments, at high as 99%, including 90%, 91%, 92%, 93%, 94%, 95%, 96%, 97%, 98%, and 99% water content.

In other embodiments, twisted yarn can be produced from the hydrogel strings described hereinabove. To make a yarn, a multiround of the loop is taken out of the fixing solution and hung in the air with a weight applied at the bottom of the string. The string will elongate under such weight. The string can be elongated much more when the stretching is done at low dehydration degree. This process helps to further align the fibers. If this is done after significant crosslinking, then the deformation is limited. For example, a dried yarn of alginate is very strong and has a Young's modulus of up to 10 GPa. Such dried strings can be rehydrated after being placed back into water.

Accordingly, in some embodiments, the presently disclosed subject matter provides a method for preparing a microfiber having a uniaxial alignment, the method comprising: (a) providing at least one starting solution comprising one or more polymers; (b) applying an electrical potential to the at least one starting solution sufficient to initiate a jet stream of polymer solution; and (c) mechanically stretching the jet stream of polymer solution during or after collecting the jet stream of polymer solution in a collection bath comprising a stabilizing solution, wherein the collection bath is positioned at a separation distance such that the jet stream of polymer solution is collected before it is accelerated by an electrical field created by the applied electrical potential. In other embodiments, the collection bath comprises a rotating collection plate, wherein a rotation of the collection plate mechanically stretches the jet stream of polymer solution as it is collected thereon. In still other embodiments, the collection bath comprises a stationary collection plate, wherein the jet stream of polymer solution is deposited on the stationary collection plate using a back and forth motion to mechanically stretch the jet stream of polymer solution as it is deposited on the stationary collection plate. In some embodiments, one or more polymers comprise a natural polymer. In other embodiments, the natural polymer is selected from the group consisting of water soluble polysaccharides, proteins, and combinations or blends thereof. In particular embodiments, the natural polymer is selected from the group consisting of one or more of alginate, fibrinogen, gelatin, collagen, hyaluronic acid (HA), chitosan, chondroitin sulfate, dextran sulfate, heparin, heparan sulfate, functionalized derivatives thereof, and combinations or blends thereof.

In yet other embodiments, one or more polymers comprise a synthetic polymer. In some embodiments, the synthetic polymer is selected from the group consisting of a polyester and a polyamide. In other embodiments, the polyester is selected from the group consisting of polylactic acid and poly(lactic-co-glycolic) acid. In particular embodiments, the synthetic polymer is selected from the group consisting of a polyacrylate, a poly(vinyl alcohol), a poly(ethylene glycol), functionalized derivatives thereof, and combinations or blends thereof.

In some embodiments, the starting solution further comprises a thickening agent capable of increasing a viscosity of the jet stream of polymer solution. In particular embodiments, the thickening agent comprises polyethylene glycol (PEG).

In other embodiments, the method further comprises crosslinking the microfiber. In particular embodiments, the crosslinking is selected from the group consisting of ionic crosslinking, ultraviolet crosslinking, enzymatic crosslinking, and a chemical crosslinking reaction. In some other embodiments, the method further comprises adding a crosslinking agent to the starting solution comprising one or more polymers. In still other embodiments, the method further comprises adding a crosslinking agent to the jet stream of polymer solution after the jet stream of polymer solution is initiated by the applied electrical potential. In further embodiments, the method comprises adding a crosslinking agent to the collection bath.

In particular embodiments, the electrical potential has a range from about 2 kV to about 6 kV.

In some embodiments, the stabilizing solution comprises a solvent in which the jet stream of polymer solution is insoluble and precipitates in the stabilizing solution. In other embodiments, the jet stream of polymer solution comprises an aqueous solution and one or more water-soluble polymers and the stabilizing solution comprises an organic solvent.

In yet other embodiments, the method further comprises elongating the microfiber by applying mechanical stress along the uniaxial alignment thereof and drying the microfiber.

In some embodiments, the method further comprises combining multiple microfibers to form a fiber bundle.

In other embodiments, the at least one starting solution comprises a blend of two different polymers; or two starting solutions are provided, wherein each starting solution comprises a different polymer; and the microfiber comprises a bicomponent fiber having a core and a sheath.

In some embodiments, the method further comprises adding one or more bioactive agents to at least one starting solution. In other embodiments, the method further comprises depositing one or more bioactive agents on the microfiber after it is formed.

In still other embodiments, the method further comprises adding one or more cells to at least one starting solution. In further embodiments, the method further comprises seeding the microfiber with one or more cells on a surface of the microfiber after it is formed. In yet other embodiments, the presently disclosed subject matter provides a microfiber formed by the presently disclosed methods. In some embodiments, the microfiber has a diameter ranging from about 5 microns to about 300 microns.

In some embodiments, the microfiber comprises more than one polymer. In other embodiments, the microfiber comprises a bicomponent fiber comprising a core and a sheath.

In further embodiments, the microfiber comprises a hydrogel. In still further embodiments, the hydrogel has a water content of greater than about 90%. In other embodiments, the hydrogel has a water content of greater than about 95%. In still other embodiments, the hydrogel has a water content of greater than about 98%.

In some embodiments, the microfiber has internal molecular chain alignment.

In other embodiments, the microfiber further comprises one or more bioactive agents. In still other embodiments, the microfiber further comprises one or more cells.

In other embodiments, bioactive agents may be either post-loaded in the microfibers or loaded in situ within the microfiber as a component of the starting polymer solution, wherein the bioactive agents may include, but are not limited to, therapeutic agents, nanoparticles, water soluble proteins, cells, and their like. In still other embodiments, the bioactive agents are used for localized, sustained release in vitro or in vivo.

II. Use of Electro-Mechanically Stretched Microfibers as Scaffold Materials for Cell or Tissue Growth A highly endeavored topic in regenerative medicine is to create extracellular matrix (ECM) analogs for providing mechanical supports and biochemical cues to cells. For cases, such as tendons, nerves and corneal stroma and intervertebral-disc regeneration, a matrix that can guide cellular alignment and growth direction is essential for optimal results.

Many new scaffold materials have been developed for such purposes. For example, Zhang et al. have developed self-assembly peptide hydrogel strings that can align encapsulated cells and others also have used electrospun nanofibers to guide cellular growth direction. Aligned ECM made from natural polymer fibers, which in many cases possess unprecedented biological performance, are limited however to microfluidic alignment, cyclic mechanical stretching, and the like.

The facile, organic solvent-free processing conditions of the presently disclosed methods are amenable to the incorporation of live cells and/or growth factor proteins within the hydrogel fiber or on the fiber surface and effectively induce cellular alignment and provide cellular growth guidance.

Accordingly, in some embodiments, the presently disclosed microfiber having a uniaxial alignment can be used as a template for growing and guiding cells. The presently disclosed microfibers also can incorporate encapsulated cells and/or growth factor proteins. Such microfibers can be used for making a cellular guide, a nerve guide for neuronal regeneration, a template for growing micro-blood vessels, surgical sutures, wound dressing, or tissue scaffolds for tissue engineering.

In further embodiments, a co-axial spin of a hydrogel core/sheath structure with cellular content in the core also can be produced.

In a representative example, the electro-mechanically stretched hydrogel string can be used to direct the orientation of cells trapped inside. After dispersing mammalian cells in alginate/fibrinogen mixture solution, the hydrogel strings can be stretched and collected in 50 mM $CaCl_2$) and 5-20 units/mL thrombin solution to form hydrogel fibers with encapsulated cells. The facile spinning condition will ensure that the encapsulated cells remain viable during the process of fiber formation and culture.

In other embodiments, the same cells can be cultured on the surface, as well. It is obvious to those skilled in the art that these cells can align with the axis of the fiber.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

III. In Vitro Cellular and Extracellular Matrix (ECM)

A novel in vitro model and system that recapitulates key aspects in the cellular and extracellular matrix (ECM) organization of the microvasculature is established in accordance with the invention. This model and system guide the formation of organized microvascular structures, induction of endothelial cell alignment and elongation, and demonstrates circumferential deposition of ECM proteins by endothelial progenitor cells, for example endothelial colony forming cells. The model reveals the role of vessel diameter on ECM organization during human microvascular growth. The model supports a step-wise vascular formation process via introduction of perivascular cells and different growth factors at varying time points, a current challenge in microvascular tissue engineering. A multicellular microvascular structure with an organized endothelium and multicellular perivascular tunica media is also disclosed.

Most current approaches for the in vitro study of the microvasculature in a 3D setting use hydrogels and scaffolds embedded with vascular cells, which are subject to spontaneous capillary bed formation (Hielscher A C, et al., *Am J Physiology—Cell Physiology*, 2012; 302: C1243-C1256; Soucy P A and Romer L H, *Matrix Biology*, 2009; 28: 273-283; Hanjaya-Putra D, et al., *Blood*, 2011; 118: 804-815, Moon J J, et al., *Biomaterials*, 2010; 31: 3840-3847; Pham Q P, et al., *Tissue Eng*, 2006; 12: 1197-1211; Benjamin L E, et al., *Development*, 1998; 125: 1591-1598; Gerhardt H, Betsholtz C, *Cell and Tissue Research*, 2003; 314: 15-23; Stratman A N, et al, *Blood*, 2009; 114: 5091-5101; Wang Z Z, et al., *Nat Biotech*, 2007; 25: 317-318; Koike N, et al., *Nature*, 2004; 428: 138-139; Melero-Martin J M, et al., *Circulation Research*, 2008; 103: 194-202; Levenberg S, et al., *Nature Biotechnology*, 2005; 23: 879-884; Hielscher A C, Gerecht S, *Cancer Research*, 2012; 72: 6089-6096; Soucy P A, et al., *Acta Biomaterialia*, 2011; 7: 96-105; Hanjaya-Putra D, et al., *Biomaterials*, 2012; 33: 6123-6131; Leslie-Barbick J E, et al., *Biomaterials*, 2011; 32: 5782-5789), or use micropatterned hydrogels to generate organized microvasculature structures (Baranski J D, et al., *Proc Natl Acad Sci USA*, 2013; Miller J S, et al., *Nat Mater*, 2012; 11: 768-774; Zheng Y, et al., *Proc Natl Acad Sci USA*, 2012; 109: 9342-9347). While these approaches are instrumental for studying angiogenic processes, they provide only partial control over the topographical cues presented to the cells by the ECM and possess limited opportunities to create and investigate multi-cellular vascular structures with proper ECM organization.

Previous studies in the field of angiogenesis, vasculogenesis, and vascular tissue engineering have either focused on studying the formation of capillaries and vessels with diameters below 100 µm (Hanjaya-Putra, D., et al., *J Cellular and Molecular Medicine*, 2010; 14(10):2436-2447; Hanjaya-Putra, D., et al., *Blood*, 2011; 118:804-815; Davis, G. E., et al., *Birth Defects Research Part C: Embryo Today: Reviews*, 2007; 81(4):270-285; Montaño, I., et al., *Tissue Engineering Part A*, 2009. 16(1): p. 269-282; Chen, X., et al., *Tissue Engineering Part A*, 2008. 15(6): p. 1363-1371; Kobayashi, A., et al., *Biochemical and Biophysical Research Communications*, 2007. 358(3): p. 692-697; Dickinson, L. E., et al., *Soft Matter*, 2010. 6(20): p. 5109-5119; Tsuda, Y., et al., *Biomaterials*, 2007. 28(33): p. 4939-4946; Baranski, J. D., et al., *PNAS*, 2013. 110(19): p. 7586-7591), or have instead aimed to develop large-diameter tissue engineered vessels, most over 3 mm in diameter (Vaz, C. M., et al., *Acta Biomaterialia*, 2005. 1(5): p. 575-582; Kelm, J. M., et al., *J Biotechnology*, 2010. 148(1): p. 46-55; L'heureux, N., et al., *FASEB Journal*, 1998. 12(1): p. 47-56; Dahl, S. L., et al., *Cell transplantation*, 2003. 12(6): p. 659-666; Quint, C., et al., *PNAS*, 2011. 108(22): p. 9214-9219).

The invention overcomes challenges to developing physiologically relevant microvascular structures with diameters between 100 µm and 1 mm. It previously has been established that ECs can create vascular networks in vitro when cultured in 3D matrices such as hydrogels, yet these networks result in capillary beds with relatively small lumen diameters (Hanjaya-Putra, D., et al., *J Cellular and Molecular Medicine*, 2010; 14(10):2436-2447; Hanjaya-Putra, D., et al., *Blood*, 2011; 118:804-815; Davis, G. E., et al., *Birth Defects Research Part C: Embryo Today: Reviews*, 2007; 81(4):270-285; Montaño, I., et al., *Tissue Engineering Part A*, 2009. 16(1): p. 269-282; Chen, X., et al., *Tissue Engineering Part A*, 2008. 15(6): p. 1363-1371). Therefore, to create vessels with a larger diameter the present invention guides the formation of cylindrical vascular structures in the order of hundreds of microns. Microfluidic channels have been used extensively to study microvascular development processes, yet most of these studies are done in channels with a square cross-section or in non-implantable devices (Verbridge, S. S., et al., *J Biomedical Materials Research Part A*, 2013. 101(10):2948-2956; Abaci, H. E., et al., *Sci. Rep.*, 2014:4).

Recent studies have developed 3D microfluidic channel arrays with rectangular (Zheng, Y., et al., *PNAS*, 2012; 109(24):9342-9347) or circular cross-sections embedded in hydrogels (Miller, J. S., et al., *Nature Materials*, 2012; 11(9):768-774; Wu, W., et al., *Advanced Materials*, 2011; 23(24):H178-H183; Kolesky, D. B., et al., *Advanced Materials*, 2014; 26(19):3124-3130; He, J., et al., *Adv. Healthcare Materials*, 2013; 2(8): p. 1108-1113). However, these present limited success for constructing a multilayered structure with a continuous endothelium and a robust supporting multicellular mural cell layer. To address the need for mural cell involvement, some of these studies incorporated perivascular cells in the hydrogels encompassing the microfluidic channels, and afterwards seeded ECs in the lumen (Zheng, Y., et al., *PNAS,* 2012; Miller, J. S., et al., *Nature Materials,* 2012). While this approach allows the study of cell recruitment, it imposes a barrier for full investment of perivascular cells, which have to migrate through the hydrogels to find the developing microvessels. As such, perivascular cells in these systems were not demonstrated to form a uniform multicellular layer on top of the endothelium. Furthermore, these systems impart a barrier for the detailed study of ECM organization and EC-mural cell interactions due to chemical and physical limitations presented the hydrogels.

The microfiber according to the invention provides control over the topographical cues presented to cells by the ECM. The microfiber of the invention also presents opportunities to create and investigate multi-cellular vascular structures with proper ECM organization. The microfiber according to the invention has a nanotopography that induces longitudinal adhesion and alignment of endothelial progenitor cells, for example, endothelial colony-forming cells (ECFCs). The endothelial progenitor cells, such as ECFCs, deposit circumferentially organized ECM. The ECM wraps around the microfibers of the invention, which is independent of ECFCs' actin and microtubule organization. As established by the present invention, ECM encircling or wrapping around the microfibers is dependent on the curvature of the microfiber. According to the invention, microfibers with small diameters, for example less than about 500 μm, preferably about 100 μm to about 450, more preferably about 100 μm to about 370 μm, guide circumferential ECM deposition. Microfibers with larger diameters, 445 μm and higher, do not support wrapping ECM as effectively. The invention provides a novel in vitro structure and method for the sequential control of microvasculature development and reveals the unprecedented role of the endothelium in organized ECM deposition regulated by the microfiber curvature.

Unless defined otherwise, technical and scientific terms used herein have the same meaning as commonly understood by one of ordinary skill in the art to which this invention belongs. As used herein, the terms "perivascular cells" and "mural cells" have the same meaning. The term "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The present invention can be used as a model of the microvasculature that recapitulates both cellular and ECM organization, towards the understanding of microvasculature development and utilization of the model for regenerative medicine applications. Towards this, electrostretched microfibers designed to generate a micro-cylindrical mold with a line-grating nanotopography are used to enable both endothelial layer organization and co-culture of supporting perivascular (mural) cells, such as vascular smooth muscle cells (vSMCs) or pericytes. Microfibers used have diameters of about 500 μm or less, preferably ranging from about 100 μm to about 450 μm, corresponding to a poorly studied range of vasculature in the body, namely venules and arterioles. Furthermore, in the existing models of microvasculature, the deposition and organization of ECM proteins by endothelial cells has not been studied. Moreover, the full investment of mural cells on the endothelium of microvascular models has been challenging, due in part to the use of endothelial-lined void spaces in most models (Miller J S, et al., *Nat Mater,* 2012; 11: 768-774; Zheng Y, et al., *PNAS USA,* 2012; 109: 9342-9347), which introduces a cell migration barrier for mural cell investment. In contrast, the model of the invention allows not only high resolution studies of both cell and ECM organization; it allows introduction of mural cells after endothelial layer formation and enables full investment of these mural cells, recreating the media layer of microvasculature.

This new approach to create aligned hydrogel microfibers as described herein uses an electrostretching process from various polymer materials. Unique characteristics of the electrostretched polymer fibers are the internal and topographical alignment of the fibrous structure, generated as a result of both electrical field and mechanical shear-induced polymer chain alignment. Furthermore, the microfiber diameter is controllable and uniform as a result of the bundling and processing of the individual fibers composing the microfibers.

The typical electrospinning process, such as disclosed in International Publication WO2013/165975, incorporated by reference herein, consists of a syringe pump with a syringe containing a polymer solution of one or more polymers, a high voltage source, and a grounded collecting plate. The technique is based on inducing an electric charge on the polymer solution while applying an electric field between the syringe needle and the grounded collecting plate. As the solution is dispensed from the syringe, the electrostatic force opposes the surface tension of the polymer solution producing a Taylor cone. Eventually the electrostatic force overcomes the surface tension to produce a liquid jet stream. As the jet travels, the electric forces cause the stream to spin. At the same time, the solvent evaporates from the solution and the polymer fibers fall on the collecting plate forming an ultrathin nanofiber. (See WO2013/165975).

The novel electrospinning/electrostretching technique of the invention modifies the typical electrospinning processes, and produces hydrogel microfibers with a uniaxial aligned topography using a combination of electrical and mechanical stretching. The typical electrospinning process was modified so the collecting plate was a grounded rotating disc containing an aqueous solution (See FIG. 7). The polymer jet emitted from the syringe is deposited as nanofibers that fall on top of each other in the rotating disc bath. At this point, the bundle of aligned nanofibers is not cohesive. To make a cohesive microfiber, the electrospun nanofibers are collected together parallel to each other and stretched mechanically by the rotating disc, then air-dried so the nanofiber bundle becomes the microfiber. This bundle is further stretched to obtain a cohesive uniaxial internal and topographical alignment, which enhances the mechanical properties of the microfibers. Alternatively, the nanofibers can be collected together and partially stretched on a modified plastic frame to make a flat 2D nanofiber sheet.

Various polymers may be used in the electrostretching technique of the invention, such as natural polymers including alginate, fibrin (fibrinogen), gelatin, hyaluronic acid (HA), chitosan chondroitin sulfate, dextran sulfate, heparin, heparan sulfate, and functionalized derivatives thereof, and synthetic polymers selected from a polyester and a polyamide, such as polyacrylic acid derivatives and polyvinyl alcohol, including polylactic acid, poly(lactic-co-glycolic) acid, polyacrylate, poly(vinyl alcohol), poly(ethylene glycol), as well as combinations thereof, that produce hydrogel polymer fibers useful in the invention. Nanofibers formed from the polymer may be crosslinked. Crosslinking may be achieved by any cross-linking method, including ionic crosslinking, ultraviolet crosslinking, enzymatic crosslinking, and chemical crosslinking reaction. For the electrostretching technique presented in the invention, the preferred polymers that can be used are alginate, gelatin, fibrin (fibrinogen), hyaluronic acid, and combinations thereof, with fibrin being the most preferred polymer.

Fibrin gels have been used to study microvasculature assembly (Dickinson L E, et al., *Soft Matter*, 2010; 6: 5109-5119; Bayless, K J, and Davis, G E, *Biochemical and Biophysical Research Communications*, 2003; 312: 903-913; Davis G E, and Bayless K J, *Microcirculation*, 2003; 10: 27-44; Bayless K J, et al., RGD-Dependent American Journal of Pathology, 2000; 156: 1673-1683; Dickinson L E, et al., *Lab Chip*, 2012; 12: 4244-4248), vSMC responses (Ahmann K A, et al., *Tissue Eng Part A*, 2010; 16: 3261-3270; Long J L, and Tranquillo R T, *Matrix Biol*, 2003; 22: 339-350) and multicellular organization (Lesman A, et al., *Biomaterials*, 2011; 32: 7856-7869). Fibrin is used as a matrix material for the microfiber according to the invention, including use in preparing hydrogel microfibers as a template for the step-wise creation of microvasculature of the invention.

The polymer microfiber of the invention has an aligned nanotopography that guides alignment and elongation of endothelial progenitor cells, such as ECFCs. The invention provides a microfiber having cylindrical shape and tunable diameter of the fibers, which are novel features in hydrogels that allow detailed 3D view and analysis of microvasculature development. The novel features also allow analysis of the effect of curvature of the fiber on cell processes. In an embodiment of the invention, fibrin is used for the hydrogel microfiber, which makes the scaffold not only biocompatible, bio-adhesive, and pro-angiogenic, but also easily degradable, such as through plasmin fibrinolysis. The development of delimited microvascular structures in small size range, for example less than about 500 μm, preferably about 100 μm to 450 μm, with demonstrated detailed cell and ECM organization has not been previously achieved.

According to the invention, aligned polymer microfiber (nanofiber bundles) used as a cylindrical platform control the organized adhesion of endothelial progenitor cells, such as ECFCs. In an embodiment of the invention, endothelial progenitor cells like ECFCs are cultured on electrospun fibrin microfibers that have a diameter of less than about 500 μm, preferably 100 μm to about 450 μm. The cells attach throughout the microfibers. ECFCs form a continuous monolayer over the entire microfiber, with a distinctive elongated and mature morphology. The polymer microfibers offer an innovative approach in which ECFCs are seeded on the surface of an electrostretched microfiber, as opposed to seeded in the body of a nanofiber mesh, as conventional electrospun scaffolds have been used (Pham Q P, et al., *Tissue Eng*, 2006; 12: 1197-1211; Kumbar S G, et al., *Biomed Mater*, 2008; 3: 034002; Christopherson G T, et al., *Biomaterials*, 2009; 30: 556-564; Chua K N, et al., *Biomaterials*, 2006; 27: 6043-6051).

Figure 7A:
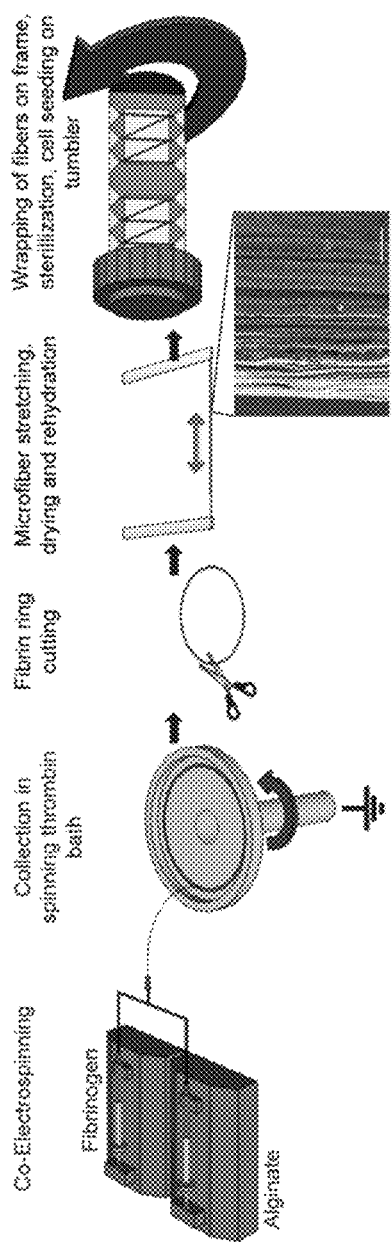
Figure 7E:
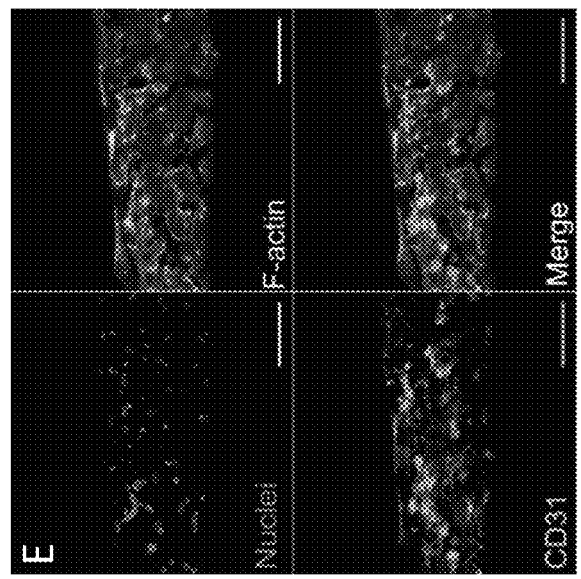
Figure 7D:
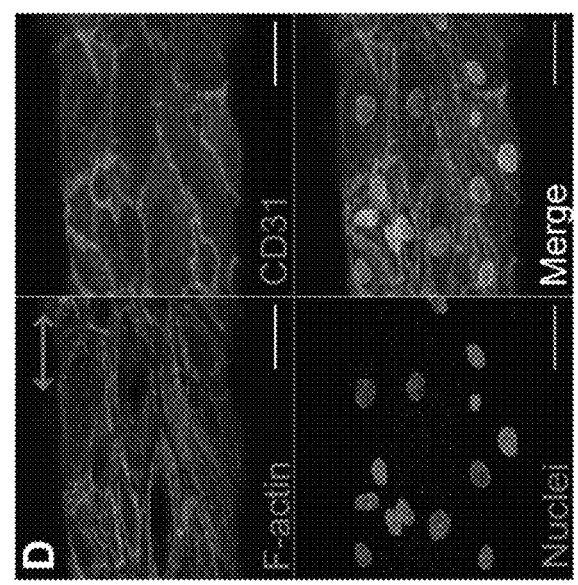

In an embodiment of the invention, ECFCs cultured on polymer microfibers of the invention exhibit typical membrane expression of endothelial markers VEcad and CD31, and cytoplasmic expression of von Willebrand factor (vWF) (FIG. 7b-d). Expression of the endothelial markers demonstrates that fibrin microfibers support the adhesion and culture of ECFCs. This unique approach allows detailed control of the cellular assembly of microvasculature, as the fibrin microfibers present a blueprint with a unique aligned nanotopography for adhesion of ECFCs.

In embodiments of the invention, ECFCs deposit ECM that wraps circumferentially around the polymeric microfiber of the invention. Examining the ECFC-deposited ECM organization on the microfiber after 5 days in culture, ECFCs deposit ECM proteins, for example, collagen IV, fibronectin and laminin. ECM proteins wrap in discrete circumferentially aligned segments on the microfibers, perpendicular to the cells macroscopic cellular alignment and intracellular cytoskeletal organization. This feature of the ECFCs in which they deposit abundant ECM (Kusuma S, et al., *FASEB J*, 2012; 26: 4925-4936), that is assembled circumferentially on a micro-cylindrical platform, recognizes an active role of the endothelium in the construction of the extracellular components of the microvasculature. In longer period cultures of ECFCs on fibrin microfibers (i.e. >10 days) full coverage of the structures by ECM was observed (data not shown). However, at this time point the initial circumferential organization of the ECM could not be analyzed due to several layers of ECM being deposited on top of each other. For quantification purposes, cultures of ECFC were analyzed when ECM organization was evident, before full coverage was achieved.

Circumferential wrapping of ECM by ECFCs has not been observed previously. To elucidate whether the ECFC alignment or the cylindrical structure and 3D aspect of the scaffold had a direct effect on ECM organization, two different systems have been used. A flat polymer sheet with the same nanotopography as the polymer microfibers can be used as a first scaffold; the flat polymer sheet varies the shape and geometry of the scaffold. ECFCs align with the nanotopography of the polymer sheets, but the ECM is deposited with no distinguishable organization. A second scaffold for use is a polymer microfiber, such as polyethersulfone (PES), coated with a polymer such as fibrin, which maintains the microfiber's spatial geometry, but has a random surface topography. ECFCs seeded on the polymer microfiber, for example PES fibers, are not induced to align with the fiber's longitudinal axis, but they deposit ECM wrapping circumferentially around the polymeric microfiber, similar to ECFCs seeded on fibrin microfibers. Without being bound by theory, it is believed that the cylindrical shape of the fibers, and not the cellular organization induced by the scaffold's nanotopography, is necessary for ECM circumferential deposition.

The cytoskeleton is known to regulate endothelial alignment (Ranj an A, and Webster T, *Nanotechnology*, 2009; 20: 305102; Liliensiek S, et al., *Biomaterials*, 2010; 31: 5418-5426; Bettinger C J, et al., *Adv Mater*, 2008; 20: 99-103; Lu J, et al., *Acta Biomater*, 2008; 4: 192-201) and drive angiogenic responses through ECM-interactions (Bayless K J, Davis G E, *Journal of Cell Science*, 2002; 115: 1123-1136; Hanjaya-Putra D, et al., *J Cell Mol Med*, 2009). Cytoskeleton re-arrangement of ECFCs seeded on fibrin microfibers through actin and tubulin configuration revealed that ECFC alignment on the microfibers is not instrumental for the circumferential deposition of ECM by ECFCs. Inhibition of neither actin filament nor microtubule polymerization affected ECM circumferential organization around the fibrin microfiber. Thus, ECM expression and organized deposition from ECFCs can be independent of ECFC cellular organization. Furthermore, shorter culture time periods, for example 3 days, which did not always produce a confluent endothelium still resulted in wrapping ECM, suggesting an independence of cell density on ECM organization.

Overall, even though aligned topography of the polymer microfibers induces ECFC alignment, the findings that either ECFCs seeded on PES fibers or ECFCs seeded on fibrin microfibers with disrupted actin and microtubule organization still produce wrapping ECM suggest that ECM organization is regulated by 3D geometric sensing of curvature, rather than by the nano-topography of the scaffold.

In an embodiment of the invention, the microfiber system demonstrated that circumferential wrapping of the ECM depends on the curvature of the microfibers. While curvature of nano-scale features of ECM has been suggested to regulate cellular responses (Vogel V, and Sheetz M, *Nat Rev Mol Cell Biol,* 2006; 7: 265-275), its effect on cellular responses at the micro-scale and during microvascular formation and organization has not been previously investigated. In this invention, polymer microfibers with an aligned nanotopography are generated by electrostretching. Microfibers are produced with uniform and tunable diameters while preserving the aligned nanotopography. In one exemplary embodiment, fibrinogen is mixed with alginate in-line and then charged with electric potential of about 2 kV to about 6 kV; the mixture is extruded through a 25-gauge needle. The fibrinogen-alginate solution jet is collected at a distance of about 3 to about 5 cm from the needle tip, in a grounded, rotating bath containing calcium chloride and thrombin as a cross-linking solution, to generate aligned nanofibers that can later be bundled to form microfibers with an aligned nanotopography. Microfibers are generated with different diameters by varying the collection time, such as from about 5 min and higher, preferably from any time point from about 5 min to about 80 min, more preferably from any time point from about 7 to about 80 min. Microfiber formation may include crosslinking nanofibers by any crosslinking method, including ionic crosslinking, ultraviolet crosslinking, enzymatic crosslinking, and chemical crosslinking reaction. After formation of crosslinked fibrin-alginate nanofibers, alginate is removed, preferably by soaking fibers in a sodium nitrate solution. Excess sodium citrate is washed off and the resulting fibrin nanofibers are collected as an aligned bundle, stretched preferably to 150% of their initial length, and dried. Resulting fibrin microfibers can be wrapped around a custom-made plastic frame and then sterilized for use.

Microfibers with diameter ranging from about 100-500 μm were examined. Microfibers of up to about 450 μm in diameter guide the organized wrapping of deposited ECM. Preferably, microfibers have a diameter about 100 μm to about 450 μm, more preferably about 100 μm to about 400 μm, about 100 to about 350 μm, about 100 to about 300 μm, about 100 to about 250 μm, about 200 μm, about 150 μm, and diameters within the ranges, such as about 110 μm, about 120 μm, 130 μm, 140 μm, 150 μm, 200 μm, 250 μm, 300 μm, 350 μm, 400 μm, 450 μm. Larger microfibers resulted in a more random ECM organization. This observation is the first to suggest an effect of the microtubular curvature on ECM organization. In contrast to studies using larger diameter templates to study ECM deposition of perivascular cells (Grassl E, et al., *J Biomedical Materials Research Part A,* 2003; 66: 550-561), the smaller diameter fibers demonstrate the role of curvature at the micro-scale.

The versatility of the polymer microfiber system is evident in allowing sequential and controlled introduction of other cells, which can deposit ECM. ECFCs will initially have an inverted polarity due to the presence of the fiber where the luminal surface would be and an absence of a tunica media on top. The first step towards correcting this inverted polarity was obtaining full investment of mural cells on top of the endothelium. Embodiments of the invention relate to the polymer microfiber cultured with endothelial progenitor cells being further seeded with a second cell type, such as perivascular cells, or mural cells. Preferably, the perivascular cell or mural cell is a vascular smooth muscle cell (vSMC) or pericyte. Both pericytes and vSMCs introduced independently into the model after ECFC culture on the fibrin microfibers were found to attach to the ECFC-seeded microfibers. The vSMCs and perictyes showed organizations that varied from the random, sporadic attachment typical of muscular venules, to the circumferential wrapping observed in arterioles under physiological conditions (Standring S, 2008). The organization, however, was in a multi-layer configuration as opposed to the monolayer formed by the ECFCs, in accordance to the multilayer organization observed in the tunica media of native vessels. The different morphologies observed between vSMCs, pericytes and ECFCs are likely a result of lack of pulsatile flow, which has been shown to induce circumferential wrapping of vSMCs in different studies (Lee A A, et al., *J Biomech Eng,* 2002; 124: 37-43; Liu B, et al., *Biophysical Journal,* 2008; 94: 1497-1507). Indeed, the lack of internal pressure in this system is more conducive to the generation of muscular venules, which have much lower blood pressures compared to arterioles and contain randomly oriented vSMCs or pericytes (Standring S, 2008).

A further step to correct the polarity of the ECFCs in the model is obtaining a defined lumen to create a hollow microvascular vessel. A further advantage of the fibrin microfiber scaffold is its biodegradability; fibrin can be easily degraded in a controlled manner using plasmin in conditions that do not affect cell viability (Neidert M R, et al., *Biomaterials,* 2002; 23: 3717-3731). In an embodiment of the invention, degradation of the fibrin microfibers generates a hollow microstructure with a defined lumen, which can be used for applications in vivo. Thus, the fibrin microvascular system provides opportunities to correct the initial ECFC polarity and to study flow-induced vSMC or pericyte organization post fibrin core degradation.

vSMCs and pericytes attach on ECFC-seeded microfibers and deposit extracellular proteins. vSMCs attach and grow on the ECFC layer (FIGS. 12 *a-c*) and deposit collagen Type I and elastin (FIGS. 12 *d-g*). The collagen type I and elastin are located below and in between the vSMC layer, and above the ECFCs (FIGS. 12 *e, g*). Pericytes attach and grow on the hydrogel microfiber scaffold (FIGS. 13 *a-c*), deposit collagen Type IV (FIGS. 13 *d-e*), which is located below and in between the pericyte layer and above the ECFCs.

These results establish that co-cultured vSMCs and pericytes deposited ECM components that organize the subendothelial connective tissue and internal elastic lamina, located in between the endothelium and the tunica media, as well as components of the tunica media itself. Co-culture experiments in ECFC media was found to support ECFC, pericytes, and vSMC viability.

Self-supporting structures with the abundant vascular ECM deposition necessary to withstand pulsatile flow as well as vasoconstriction and vasodilatation are disclosed. ECM proteins such as collagens, laminin, and elastin have been shown to provide these biomechanical properties. To date, the study of ECM protein deposition by different vascular cells in 3D constructs either alone or in co-culture has been limited (Davis, G. E. and D. R. Senger, *Circulation Research,* 2005; 97(11): p. 1093-1107.). In an embodiment of the invention, increased quantities of ECM were deposited on the 3D microfibers of the invention compared to 2D cultures after seeding ECFCs, pericytes, and vSMCs in 2D and 3D culture. The 2D surfaces were coated with a thick fibrin hydrogel layer to provide a similar stiffness and bioactive substrate compared to its 3D counterpart. For ECFCs, immunofluorescence microscopy revealed increased deposition of ECM proteins Col IV, Fn, and Lmn in 3D compared to 2D (FIGS. 14 a,b). This increased expression was found to be about 2-fold for Fn and Lmn and almost 4-fold for Col IV, as measured by RT-PCR (FIG. 14 c). These results indicate the existence of a geometrical or biomechanical sensing pathway that upregulates the production of these proteins comprising the basal lamina of native endothelium (Laurie, G., et al., Cell Biology, 1982; 95(1): p. 340-344).

Similar studies performed on pericytes and vSMCs revealed these cell types produce several different ECM proteins that comprise the subendothelial connective tissue, internal elastic lamina, and ECM of the tunica media of blood vessels (Brooke, B. S., et al., Trends in Cell Biology, 2003; 13(1):51-56; Hungerford, J. E., et al., Developmental Biology, 1996; 178(2):375-392). In the fibrin hydrogel microfiber of the invention, both pericytes and vSMCs produced Col types I, III, IV, as well as Fn and Lmn. Additionally, only vSMCs produced Eln, which is in accordance to native vasculature where elastic tissue is found predominantly in arterioles and arteries with a full vSMC layer and not in smaller capillaries or venules invested only by pericytes (Hibbs, R. G., et al., Am Heart J, 1958. 56(5):662-670; Yen, A. and I. M. Braverman, J Investig Dermatol, 1976. 66(3):131-142; Brooke, B. S., et al., Trends in Cell Biology, 2003; 13(1):51-56). Notably, there is an increase in average expression of all ECM proteins deposited by perivascular cells in 3D compared to 2D microfibers, though the upregulation was only statistically significant for Col I, Col IV, and Eln deposition by vSMCs (FIGS. 15 a-c, 16 a-c). Furthermore, the morphological expression of these proteins was found to be more organized in 3D than 2D substrates, and Lmn was found to be deposited extracellularly in 3D microfiber substrates only. This is evidence of distinct metabolic pathways that regulate the expression and deposition of different ECM proteins by vSMCs and pericytes. The fibrin microfibers provide an appropriate microenvironment for abundant, organized ECM deposition.

Figure 17:
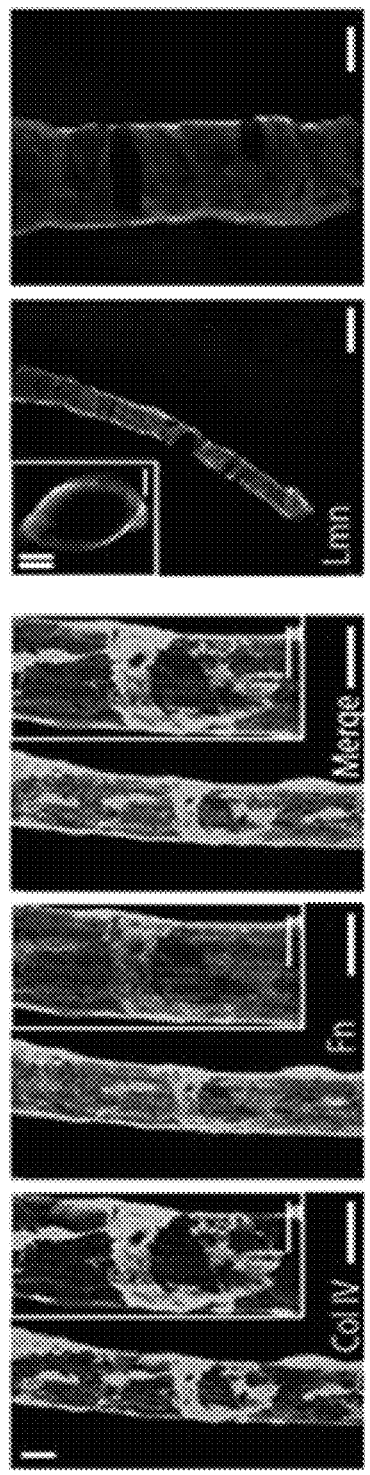

In a further embodiment, hollow microvascular vessels are prepared by removing the polymer microfiber core from the microvascular structures. An advantage of fibrin as a polymer biomaterial, besides its natural biocompatibility, bioadhesiveness, and angiogenic promoting characteristics (Clark, R. A. F., 2003; 121(5): p. xxi-xxii), is its biodegradability in response to enzymes such as plasmin, the enzyme responsible for eliminating fibrin blot clots in the human body (Rijken, D. C. and H. R. Lijnen, J Thromb Haemost, 2009; 7(1):4-13). In a further embodiment, varying plasmin concentrations in serum free media were shown to degrade fibrin microfibers at different time points (FIG. 17 a). The plasmin concentration ranged from 0.1 to 15 CU/mL. In a preferred embodiment, a 12 hr degradation treatment of 0.25 CU/mL plasmin was able to maintain cell viability similar to control culture conditions while a 24 hr treatment of 0.1 CU/mL plasmin was more detrimental to cell survival possibly due to the longer period of serum starvation (FIG. 17 b). Degradation of ECFC-seeded fibrin microfibers after 5 days of culture revealed that both the 12 and 24 hr treatment protocols were able to degrade the fibrin microfiber core while maintaining the intact ECM deposited by ECFCs, resulting in an early microvascular structure comprised of an endothelial layer and its basal lamina with a clear circular lumen (FIG. 17 c).

In further embodiment of the invention, luminal multicellular microvascular structures were created by adding perivascular (mural) cells to constructs that first had been cultured with ECFCs to allow full endothelial layer formation before introducing the perivascular (mural) cells. Co-cultures were further cultured and shown to be comprised of both ECFCs and mural cells along with their deposited ECM, such as Col III and Col IV for ECFC-pericyte co-cultures (FIG. 12 a). Unexpectedly, ECFC-vSMC co-cultures presented Eln deposition after only 5 days of vSMC growth (FIG. 18 b), an elusive achievement in vascular tissue engineering typically shown in vSMC cultures of over four weeks only (Kim, B. S., et al., Biotechnol Bioeng, 1998, 57(1):46-54; Gao, J., et al., J Biomedical Materials Research Part A, 2008; 85A(4):1120-1128; Patel, A., et al., Cardiovascular Research, 2006; 71(1):40-49; Long, J. L. and R. T. Tranquillo, Matrix Biol, 2003; 22(4):339-50). Finally, the resulting structures were shown to retain both cellular and ECM formation after degradation of the fibrin core, forming a distinct circular lumen (FIGS. 18 c, d).

The novel in vitro model system established in accordance with the invention demonstrates the role of vessel diameter on ECM organization during microvascular growth. The system supports a step-wise vascular formation process via introduction of perivascular cells at varying time points, a current challenge in microvascular tissue engineering. This approach can be used to develop further a mechanistic understanding of human microvasculature assembly and stabilization in health and disease.

Abbreviations

The following abbreviations may appear in the examples and elsewhere in the specification and claims:
Actin, beta (ACTB)
aminocaproic acid (ACA)
collagen type I (Col I)
collagen, type I, alpha 1 (COL1A1)
collagen type III (Col III)
collagen, type III, alpha 1 (COL3A1)
collagen type IV (Col IV)
collagen, type IV, alpha 1 (COL4A1)
elastin (Eln)
endothelial cells (ECs)
endothelial colony forming cells (ECFCs)
extracellular matrix (ECM)
fibronectin (Fn)
Glyceraldehyde 3-phosphate dehydrogenase (GAPDH)
laminin (Lmn)
Laminin subunit gamma-1 (LAMC1)
polyethersulfone (PES)
smooth muscle cells (SMCs)
three-dimensional (3D)
two-dimensional (2D)
vascular endothelial growth factor (VEGF)
vascular smooth muscles cells (vSMCs)

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Preparation and Characterization of Hydrogel Microfibers

To produce alginate hydrogel microfibers, 2-6 kV, 1.5-3.0 wt % alginate and 0.1-0.6 wt % PEG solution were used. The alginate hydrogel microfibers were stabilized in a collection bath comprising 20 mM to 100 mM $CaCl_2$) and a rotating collection plate. As a representative example, a starting solution comprising 2.0 wt % alginate (from brown algae, approximately 250 cps viscosity for a 2% solution at 25° C.) and 0.2 wt % poly(ethylene glycol) (PEG, average $M_v$ ca. 4,000 kDa, Sigma Aldrich, St Louis, Mo.) is used. The starting solution was pumped through a 27 gauge needle syringe at 2 mL/hour rate by a syringe pump. A 3-kV voltage was applied to the needle with a clamp from a high voltage power source (Gamma High Voltage Research, Ormond Beach, Fla.). The rotating collection plate in the collection bath has a diameter of about 20 cm and rotates at about 25 rpm. The rotating collection plate was positioned approximately 4 cm away from the exit of the syringe needle. The 50 mM $CaCl_2$) solution stabilizes the alginate hydrogel fibers during collection. After the hydrogel strings are collected on the rotating collection plate, they are allowed to crosslink in the 50 mM $CaCl_2$) solution for 3 min before use.

With similar flow rates and applied voltages, fibrin, gelatin and HA hydrogel fiber bundles also were prepared. In representative examples, fibrin hydrogel fibers were produced using an aqueous solution that contains 0.7 wt % fibrinogen, 1.0 wt % sodium alginate and 0.1 wt % PEG. Upon collection, the hydrogel fibers were crosslinked in 50 mM $CaCl_2$) with 5 Units/mL thrombin for 20 minutes. If necessary, a higher concentration of thrombin can be used to shorten the crosslinking time.

As another representative example, aqueous solutions that contain 2.0 wt % fibrinogen from bovine plasma (syringe 1) and 1.5 wt % sodium alginate/0.2 wt % PEG (syringe 2) were mixed through a Y junction mixer at 1:2 ratio. The mixed solution was pumped through a 25 gauge needle syringe at 3 mL/hour rate. A 4 kV voltage was used to initiate the electrostretching process. Upon collection, hydrogel fibers were crosslinked in $CaCl_2$)/thrombin solution (50 mM, 5 Units/mL) for 20 minutes. After crosslinking, the hydrogel microfibers were soaked in 250 mM sodium citrate solution overnight to remove alginate and PEG. The hydrogel microfibers were then rinsed with distilled water to remove the sodium citrate residue before use.

As an alternative to the protocol disclosed immediately hereinabove, fibrinogen and PEG (1 wt %/0.1 wt %) were directly mixed and processed at 4 kV voltage. The crosslinking solution in this case contained 50 mM $CaCl_2$) and 20-unit/mL thrombin. After 20 minutes of crosslinking, the hydrogel microfibers can be directly collected for use.

Gelatin hydrogel fibers were prepared with 3.2 wt % methacrylated gelatin, 0.9 wt % sodium alginate, 0.1 wt % PEG, and 0.4 wt % photo initiator Irgacure 2959, followed by crosslinking with 50 mM $CaCl_2$) solution for 5 minutes and then UV-irradiation at λ 365 nm for 10 minutes. Methacrylated gelatin was prepared according to a previously reported protocol (Nichol et al., 2010). As another representative example, gelatin hydrogel fibers were prepared with a solution containing 3.0 wt % methacrylated gelatin, 1.0 wt % sodium alginate, 0.15 wt % PEG and 0.4 wt % photo initiator Irgacure 2959 (CIBA Specialty Chemicals, Basel, CH). Flow rate was set as 2 mL/hour. Other processing parameters were similar to the generation of alginate and fibrin described hereinabove. Upon collection, alginate was crosslinked in 50 mM $CaCl_2$) bath for 5 minutes. UV-irradiation at λ 365 nm with Mineralight Lamp UVGL-25 (UVP LLC, Upland, CA) was then used to crosslink the gelatin for 10 minutes. After crosslinking, 250 mM sodium citrate solution was used to remove alginate, PEG and photo initiator overnight. Distilled water was then used to rinse off the sodium citrate residue before use.

Similarly, HA hydrogel fibers were prepared with 1 wt % thiolated HA, 0.7 wt % alginate and 0.2 wt % PEG, and crosslinked with 50 mM $CaCl_2$) and 1 wt % polyethylene glycol diacrylate (PEGDA). As another representative example, HA hydrogel fibers were prepared with 1.0 wt % thiolated HA (Glycosan BioSystems Inc.), 0.75 wt % alginate and 0.2 wt % PEG solution. A 4-kV applied voltage was used to initiate the jet. The flow rate used was 2 mL/hour. The collection bath contained 50 mM $CaCl_2$) and 1 wt % PEGDA to crosslink alginate and HA. After 20 minutes of crosslinking, alginate, PEG and excess PEGDA can be removed by sodium citrate and distilled water, using the protocols for generating alginate and fibrin described hereinabove.

Collagen hydrogel fibers were prepared with 2.0 wt % methacrylated collagen (syringe 1) and 1.5 wt % sodium alginate/0.2 wt % PEG/0.4 wt % photo initiator Irgacure 2959 (syringe 2). These solutions were mixed through a Y junction mixer at a 1:1 ratio. The combined solution was pumped through a 25 gauge needle syringe at 3 mL/hour rate. 4 kV applied voltage was used to initiate the jet. The collection bath contained 50 mM $CaCl_2$). Upon collection, the alginate was crosslinked in the 50 mM $CaCl_2$) bath for 5 minutes. UV-irradiation at λ 365 nm was then used to crosslink collagen for 10 minutes. After crosslinking, 250 mM sodium citrate solution was used to remove alginate, PEG and photo initiator overnight. Distilled water was then used to rinse off the sodium citrate residue before use.

Methacrylated collagen used in this example was prepared by adding methacrylic anhydride to acid solubilized type I collagen (3 mg/mL, Life Technologies, Carlsbad, CA). Before reaction, the collagen solution was adjusted to pH 7.5 with 0.2 M $Na_2HPO4$ buffer. Methacrylic anhydride (MA) was added in different ratios to obtain a desired degree crosslinking capacity. After an eight hour reaction, the mixture was dialyzed against 10 mM HCl for 2 days. Pierce Slide-A-Lyzer Concentrating Solution (Thermo Scientific, Waltham, Mass.) was used to condense the solution to the desired concentration.

Dehydrated String Bundles.

Dehydrated string bundles known in the art typically are produced by air drying. Applying an axial stress can exclude the liquid content, speed up the drying process, and enhance alignment. As a representative example, fibrin hydrogel strings collected by the protocol disclosed hereinabove was stretched to 160% of its original length and air dried. Alginate hydrogel string collected as described hereinabove also was stretched to 130% of its original length and air dried. In both cases, the hydrogel strings shrank in diameter and became dehydrated thin strings. Their average Young's modulus also drastically increased to 10 GPa for calcium alginate fibers and 2 GPa for fibrin fibers. Hydrogel strings of other compositions can be dehydrated in a similar way. Alternatively, hydrogel strings can be frozen and lyophilized to create a porous morphology. Dehydrated strings made by both methods can be rehydrated when soaked in water.

Sem Analysis.

Hydrogel microfiber samples were first serially dehydrated in 50%, 60%, 70%, 80%, 90%, 95% and 100% ethanol for 15 minutes in each solution, critical point dried, and then sputter-coated with 8-nm thick Au/Pd. Samples were imaged on a JEOL 6700F field-emission SEM (Tokyo, Japan).

Small and Wide Angle X-Ray Scattering.

SAXS experiment was performed at the Cornell High Energy Synchrotron Source (CHESS; Ithaca, NY, USA). Dry or wet hydrogel fibers were subjected to 10-second exposures of the synchrotron beam ($\lambda$=0.11521 nm, beam size: 0.5 mm horizontal×0.1 mm vertical) for 10 times. A 48 mm×48 mm 2-D CCD detector with pixel size of 46.9 µm×46.9 µm was used to collect the scattering data. The averaged intensity readings on each pixel of the detector were recorded and analyzed with fit2D. WAXS experiments were performed using a Rigaku R-Axis Spider Diffractometer (Rigaku Americas Corp., The Woodlands, TX, USA) with an image plate detector and a graphite monochromator using Cu K$\alpha$ radiation ($\lambda$=0.15418 nm). The instrument was controlled by Rapid/XRD diffractometer control software (version 2.3.8, Rigaku Americas Corp., The Woodlands, TX, USA). Fibers were grouped into a bundle and secured on the sample stage. Two-dimensional diffraction data were collected for 20 minutes while rotating the sample stage at 5° per minute. The 2D diffraction data were radially integrated with 2DP Spider software (version 1.0, Rigaku Americas Corp., The Woodlands, TX, USA).

Mechanical Testing.

Single axial stretching tests were performed over the hydrogel microfibers in dry, wet and rehydrated forms with a DMA Q800 unit from TA Instruments (New Castle, DE, USA). Experiments results revealed that, while dry fibers have limited capacity to elongate (approximately 3-5% strain at break), wet hydrogel fibers were stretched to more than 100% strain before breaking. The average Young's moduli of dry calcium alginate, fibrin, gelatin and HA fibers were 10.0 GPa, 2.2 GPa, 0.8 GPa, and 3.0 MPa, respectively. For wet fibers prior to the drying step, the Young's moduli were several orders of magnitude lower (717 kPa, 37.3 kPa, 2.6 kPa, and 1.3 kPa, respectively). The moduli of rehydrated fibers fell in between the two sets, with 108 MPa, 289 kPa, 4.4 kPa, and 58.5 kPa, respectively. In these analyses, sample diameters were determined using a light microscope. For wet strings, samples were stretched to break within 30 seconds to minimize the effect of water evaporation on measurement. The Young's moduli were calculated within the initial linear region of the stress-strain curves from the tests.

Example 2

Electromechanical Stretching Setup and Features

This strategy employs electrical and mechanical stretching to induce polymer chain alignment during spinning of an aqueous polymer solution, followed by rapid chain alignment fixation of the polymer jet via crosslinking (FIG. 1a). The electrostretching setup includes a collection bath comprising a crosslinking solution and a grounded, motor-driven rotating collection plate. The polymer jet is charged with a relatively lower electrical potential of 2-6 kV, including 2, 3, 4, 5, and 6 kV and any fractional value within the range of 2-6 kV, than typically applied for electrospinning methods known in the art (5-30 kV).

In some embodiments, the presently disclosed electromechanical stretching platform includes a high voltage power supply, a needle syringe pump, a syringe, and a motor-run rotating metal disc, i.e., the collection plate. The collection plate can have a diameter of about 20 cm. A high voltage DC power is applied to the solution by clamping an electrode on the syringe needle. The applied voltage is about 2-6 kV, and the flow rate of the solution is about 0.4-4 mL/hour. After the jet is initiated by applying the electrical potential, the stretched string is collected on the collection plate, which can be positioned about 3 cm to 5 cm away from the exit of the syringe needle in a calcium chloride solution reservoir, i.e., the collection bath. The angular velocity of the collection plate is controlled by a DC motor controller (Dart 15DVE) unit, which was usually operated in a range from about 20 to 80 rotations/minute. If more than one solution is involved, such as co-spinning of multiple components or co-axial spinning, an additional syringe pump can be used.

In some embodiments, the hydrogel fiber is made from alginate. The good biological compatibility and high viscosity of alginate makes it not only a good candidate to make hydrogel string by itself, but also makes it an ideal template to induce stretching over other materials.

The entire process is conducted in aqueous solutions. For example, a solution of sodium alginate (1.5-3.0 wt %) and polyethylene glycol (PEG, 0.1-0.6 wt %) is charged with 2-6 kV positive potential and extruded through a syringe needle at a flow rate of 1-3 mL/h. The PEG in the alginate solution serves as a thickening agent to increase the viscosity of the alginate solution jet (Ji et al., 2006). The electrical field causes the polymer solution to form a jet. The jet is further stretched upon being collected on the rotating collection plate containing 20-100 mM $CaCl_2$) solution at a collecting distance approximately 3-6 cm from the needle tip. The diameter of the collected hydrogel fiber can be tuned by adjusting the solution extrusion rate and the angular velocity (20-80 rpm) of the rotating collection plate, which in embodiments where the diameter of the rotating collection plate is 20 cm, corresponds to a linear velocity of about 20-84 cm/second. The fiber diameter increases with solution extrusion rate and decreases with rotation velocity of the rotating collection plate. For example, the average diameter of individual calcium alginate fibers can be controlled in the range of 17 µm to 116 µm by varying the flow rate of alginate (2 wt %)-PEG (0.2 wt %) solution from 0.7-7 mL/hour at room temperature (FIG. 1b). Hydrogel fibers produced with this process have highly uniform diameters (FIG. 1c), and continuous hydrogel microfibers of any length can be produced. Further, the hydrogel microfibers can be grouped together to form bundles of tunable diameters depending on the number of individual fibers used.

The versatility of the presently disclosed approach can be demonstrated by preparing internally aligned hydrogel microfibers from several natural polymers (alginate, fibrin, gelatin (Nichol et al., 2010) and hyaluronic acid (Shu et al., 2004)) using different crosslinking schemes (FIG. 1c-f). Calcium alginate hydrogel fibers were initially prepared. One important advantage of the calcium alginate hydrogel system is its fast gelation rate. Potter et al. have determined the displacement of the crosslinking reaction front in 2 wt % alginate solution to be approximately 20 µm/second in a 50 mM $CaCl_2$) crosslinking solution, and 40 µm/second in 100 mM $CaCl_2$) (Potter et al., 1994). In the electrostretching system described above, a 40-µm alginate fiber can be effectively crosslinked in about 0.5-1.0 second by the $CaCl_2$) solution. This fast crosslinking scheme allows the incorporation of other water-soluble polymers to form polymer blend fibers. Additional enzyme-, UV- or chemical-mediated crosslinking reactions can be used together with calcium ions to further stabilize the hydrogel fibers. In some embodiments, thrombin-mediated crosslinking of fibrinogen can be used to form fibrin-alginate blend fibers, UV light can be used to crosslink methacrylated gelatin-alginate fibers, and a Michael-type addition reaction can be used to crosslink thiolated hyaluronic acid-alginate fibers (FIG. 1d-f). After crosslinking, alginate and PEG can be removed from the polymer blend hydrogel fibers by washing the fibers with sodium citrate. All of these crosslinking and washing steps can be carried out in aqueous buffers under ambient conditions and therefore are cell-compatible.

Additional components, such as cells and bioactive agents, can be included by mixing them with the polymer solution or through an additional syringe pump. End point mixing nozzle or co-axial stretching nozzle also can be used. In some embodiments, fibrinogen is mixed with alginate and the mixture is co-crosslinked with $CaCl_2$) and thrombin. In other embodiments, gelatin and hyaluronic acid strings are formed by mixing methacrylated gelatin or acrylated hyaluronic acid with alginate and co-crosslinking with $CaCl_2$), photo initiator Irgacure 2959 and UV light. In these embodiments, alginate is used as a template material and can be dissolved in calcium sequester solution, such as sodium citrate, EDTA or even PBS solution for fast or slow alginate removal.

Electrostretched hydrogel microfiber bundles are mechanically stronger and easier to handle than the typical hydrogels of the same composition and size. As a demonstration, an electrostretched calcium alginate hydrogel fiber bundle was used to lift a 10-g metal weight (FIG. 1i), and also two individual alginate gel strings were tied into a micro-knot using forceps (FIG. 1j). On the contrary, bulk alginate hydrogels or alginate fibers prepared with the same concentration of alginate, but without employing the presently disclosed stretching process cannot withstand such manipulations. Due to the improved mechanical property and ease of handling, such hydrogel materials can be further fabricated into other forms like films, tubes and more (FIGS. 1l-m).

To probe the structural origin for enhanced mechanical properties, birefringence imaging of the electrostretched hydrogel fibers was conducted. The extinction of light at the cross-point of fibers (FIG. 1k) indicated strong polymer chain alignment within the hydrogel microfiber bundles.

Example 3

Figures 2A, 2B, 2C, 2D, 2E, 2F, 2G, 2H, 2I:
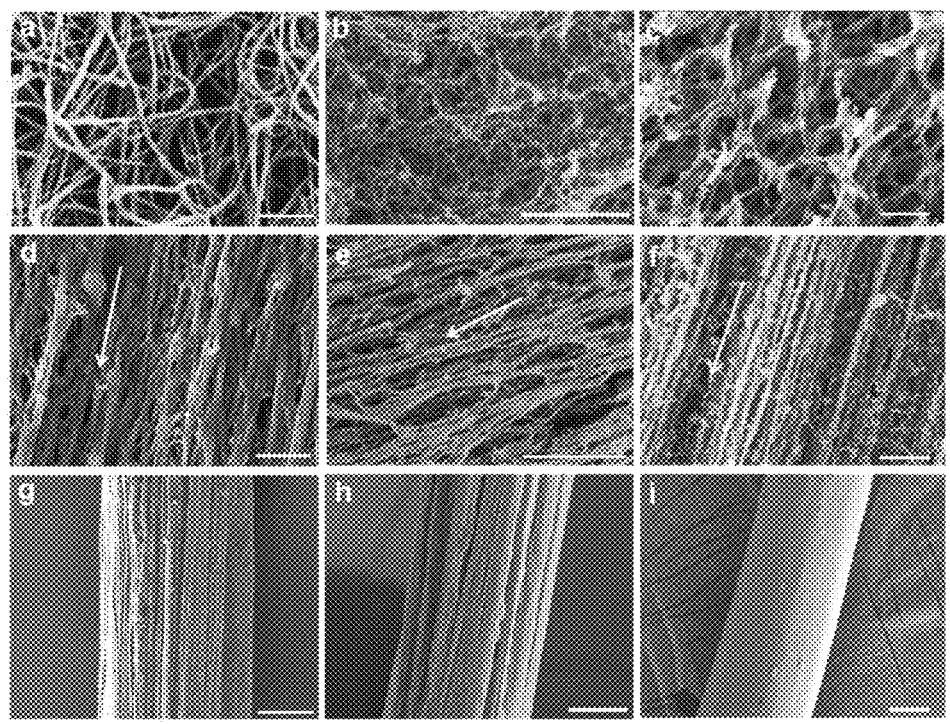

Scanning Electron Microscope Images and Small Angle X-Ray Scattering (SAXS) Patterns The alignment structure was further confirmed on critical point-dried hydrogel microfiber bundles utilizing scanning electron microscope (SEM; FIGS. 2a-2i). As shown in FIG. 2a-c, fibrin, methacrylated gelatin, and thiolated HA hydrogels prepared using simple mixing and crosslinking steps formed random nanofiber mesh networks. In contrast, the electrostretched hydrogel microfibers exhibited preferential alignment along the fiber axis (FIG. 2d-f). Such highly porous and aligned surface texture also is very different from recently developed fibrin microthreads, which are dense and smooth on the surface (Cornwell and Pins, 2007; Grasman et al., 2012). Grouping of individual fibers into bundles followed by further stretching (usually 30-100% of the initial length) and dehydration resulted in dense microfibers with aligned grooves and surface textures (FIG. 2g-h). These dry fibers can be rehydrated to about 50-100% of their original diameter depending on their drying processes.

Figures 3A, 3B, 3C, 3D, 3E, 3F, 3G:
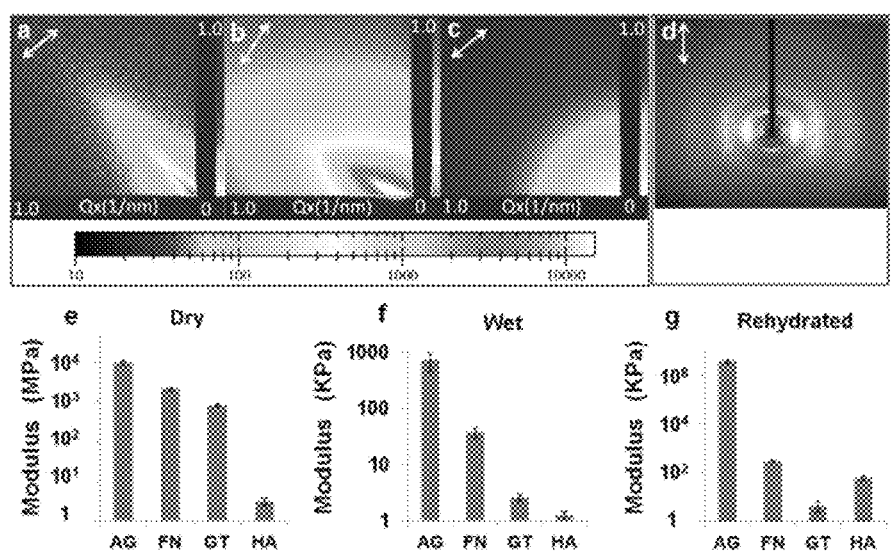
Figures 4A, 4B, 4C, 4D, 4E, 4F:
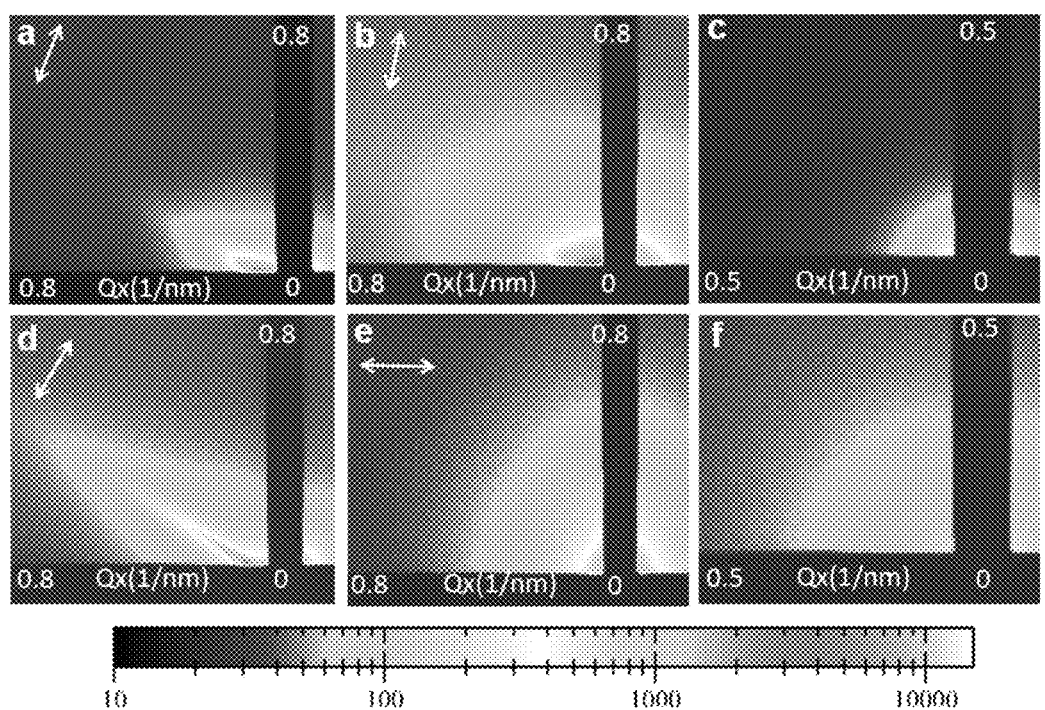

To confirm molecular alignment within the hydrogel fibers, both in dry and hydrated forms, their small angle X-ray scattering (SAXS) patterns were analyzed (FIG. 3a-b), which showed strong anisotropic scattering profiles, indicating preferential orientation along the fiber axis. As a comparison, both dry and hydrated non-stretched alginate samples gave an isotropic scattering pattern (FIG. 3c). The wide-angle X-ray scattering (WAXS) analysis of dry calcium alginate microfibers also showed a reflection profile that was indicative of an oriented polymer crystalline phase (FIG. 3d). The reflection pattern also confirmed that the polymer chains are oriented preferentially along the microfiber axis indicated by the arrow. Results with fibrin and gelatin strings are similar to that of calcium alginate (FIG. 4).

The preferential alignment of polymer chains within the microfibers greatly improved mechanical properties of the hydrogel fibers. FIG. 3e-g shows the Young's moduli of dry, wet, and hydrated hydrogel fiber bundles. While dry fibers have limited capacity to elongate (approximately 3-5% strain at break), wet hydrogel fibers were stretched to more than 100% strain before breaking. The average Young's moduli of dry calcium alginate, fibrin, gelatin and HA fibers were 10.0 GPa, 2.2 GPa, 0.8 GPa, and 3.0 MPa, respectively. For wet fibers prior to the drying step, the Young's moduli were several orders of magnitude lower (717 kPa, 37.3 kPa, 2.6 kPa, and 1.3 kPa, respectively). On the other hand, the moduli of rehydrated fibers fell in between the two sets, with 108 MPa, 289 kPa, 4.4 kPa, and 58.5 kPa, respectively. According to the theory proposed by MacKintosh et al., the modulus of an entangled network scales with concentration (MacKintosh et al., 1995). Therefore, the modulus and stiffness of the hydrogel fibers can be further adjusted by varying the concentration of starting materials, such as alginate and fibrinogen, and crosslinking density. As substrate modulus plays an important role in regulating cellular behaviors like proliferation, migration and differentiation, the ability to tune hydrogel fiber modulus and stiffness over such a wide range makes the presently disclosed hydrogel fiber matrix versatile for a wide range of applications (Engler et al., 2006; Discher et al., 2005). These analyses confirm that hydrogel fibers prepared by electrostretching exhibit polymer chain alignment along the microfiber axis. In contrast, hydrogel samples prepared by simple extrusion have an isotropic structure.

The relatively low electrical potential applied to the polymer solution (a measured current of 4-6 μA), the aqueous solvent, and ambient crosslinking conditions make this process compatible with cell encapsulation. In some embodiments, alginate is not a favorable cell scaffold matrix due to the lack of cell adhesion moieties. Therefore, in some embodiments, fibrin, gelatin or hyaluronic acid are blended in to the hydrogel fibers, each employing a unique second crosslinking step to further stabilize the hydrogel fiber matrix. For example, a solution of fibrinogen, alginate, and PEG can be mixed with cells, and subjected to the electrostretching condition as described above.

Hydrogel fibers are rapidly crosslinked by the calcium solution in the collection bath, followed by crosslinking of fibrinogen into fibrin network with thrombin. Similarly, methylated gelatin and thiolated HA can be used instead of fibrinogen using the corresponding crosslinking methods discussed in FIG. 1 (detailed conditions are listed in Table 1; all fibers describe in Table 1 were spun at 3-5 kV electrical potential and collected on a rotating collection plate spun at 20-80 rpm). All these crosslinking methods are cell-compatible. After the second crosslinking step, alginate and PEG can be removed with sodium citrate, if a higher degree of porosity is desired.

TABLE 1

Spinning Parameters for different Hydrogel Microfibers

| Hydrogel Composition | Spinning Solution Concentration (wt %) | Crosslink Method | Crosslink Condition |
|---|---|---|---|
| Alginate | 0.75-3.0% Alginate<br>0.1-0.4% PEG | Ionic crosslinking | 25-100 mM $CaCl_2$ |
| Fibrin + Alginate | 0.67-2.0% Fibrin<br>0.25-2.5% Alginate<br>0.1-0.2% PEG | Enzymatic and ionic crosslinking | 5 U/mL thrombin<br>50 mM $CaCl_2$ |
| Gelatin + Alginate | 1.0-3.2% Gelatin<br>0.24-0.86% Alginate<br>0.40-1.0% Irgacure | Ionic & UV-crosslinking | 50 mM $CaCl_2$<br>0.50% Irgacure<br>10 min UV at 365 nm |
| Hyaluronic Acid + Alginate | 1.0-2.0% HA<br>1.5% Alginate<br>0.1-0.4% PEG | Ionic & Michael addition crosslinking | 1% PEGDA &<br>50 mM $CaCl_2$ |
| Fibrin | 0.67-2.0% Fibrin<br>0.1-0.2% PEG | Enzymatic crosslinking | 20 U/mL thrombin |
| Collagen + Alginate | 0.67-2.0% Collagen<br>0.25-2.5% Alginate<br>0.1-0.2% PEG | Ionic & UV-crosslinking | 50 mM CaCl2<br>0.50% Irgacure<br>10 min UV at 365 nm |

Example 4

Loading Drugs or Other Bioactive Agents in Hydrogel Microfibers

The hydrogel microfibers can be loaded with drugs or other active agents in situ or through post-loading. In situ loading can be achieved by including these active agents in the polymer solution. As an example, nanoparticles or growth factors can be directly added into alginate solution at various concentrations and processed using the typical process for making the hydrogel microfibers in Example 1. The crosslinked calcium alginate network thus encapsulates the nanoparticles and growth factors inside the microfiber.

Alternatively, microfibers can be loaded with drugs or other bioactive agents by soaking either the hydrated or dehydrated microfiber in a solution containing the drugs or active agents. In one example of post-loading, alginate/fibrin blend microfibers are soaked in a solution containing growth factors at various concentrations for 12 hours, and then dried in the air.

Drugs and bioactive agents include, but not limiting to, grow factors, small molecular weight compounds that can promote cell growth, enhance cell differentiation and maturation, or facilitate cell migration and tissue organization. In some specific examples, bioactive agents are selected from glial cell-derived neurotrophic factor, nerve growth factor, bone morphogenic factor, hepatic growth factor, vascular endothelial growth factor, and the like.

Example 5

Culture Mammalian Cells with Hydrogel Microfibers

Cell Encapsulation into Hydrogel Microfibers.

Mammalian cells, including but not limited to adipose tissue-derived. stem cells, Schwann cells, oligodendrocytes, etc. can be encapsulated into fibrin or fibrin-alginate hydrogel microfibers at a density of 2,000-10,000 cells/μL. To produce such cell-laden hydrogel microfibers, cells can be suspended in fibrinogen solution, which is then mixed at 1:2 volume ratio through a. syringe with a solution of 1.5 wt % sodium alginate and 0.2 wt % PEG solution, and charged at +4 kV potential, and electrostrectched according to the procedure described in Example 2. The collection bath will contain a stabilization solution of 50 mM $CaCl_2$, 5 units/mL thrombin and 5% glucose to maintain the physiological osmolarity. The crosslinking step can be conducted similarly as that described in Example 2. After crosslinking, cell-laden fibers can be collected, transferred into Petri dish with media, and cultured in 5% CO) incubator at 37° C.

Culture Cells on the Surface of Hydrogel Fibers.

Microfibers prepared by the method described here can be used as a micro-scaffold for cell culture. Mammalian cells can be seeded onto the surface of hydrogel microfibers and cultured using standard cell culture techniques.

Example 6

Discussion

The presently disclosed subject matter demonstrates that a high degree of axial alignment of polymer chains inside hydrogel microfibers can be induced by a combination of electrical and mechanical stretching effects. Polymer chain alignment induction during the electrospinning process has been previously reported (Catalani et al., 2007; Bellan and Craighead, 2008; Fennessey and Farris, 2004). For example, PEG polymer chain can be aligned when the PEG solution is subjected to a 14-kV electric potential (Kakade et al., 2007). This observed alignment arises because the PEG chain has flexible C—O ether bonds in the backbone, facilitating the PEG chain alignment along water molecule dipole orientation in response to the strong electrical field (Kakade et al., 2007). This method may not be applicable to other polymer-solvent systems, however, particularly for the presently disclosed biopolymers, which exhibit longer relaxation times and coiled chain conformations.

In the presently disclosed methods, these barriers are circumvented by reducing the electric potential and extending the jet stretching time. In some embodiments, the average air travel time of the alginate solution jet ranged from about 100 msec to about 500 msec before it is collected on a rotating collection plate in a collection bath containing the crosslinking solution, in contrast to a typical air travel time about 10 msec for the liquid jet in electrospinning before solvent evaporation step (Reneker, 2000). Again, without wishing to be bound to any one particular theory, it is thought that this extended jet stretching time likely allows alginate chains to align better with the electric field.

In further embodiments, this electric field-induced polymer chain alignment can be further enhanced by mechanical stretching (FIG. 5). According to theoretical models, a high degree of polymer chain alignment can be achieved during the uniaxial stretching of a polymer solution jet if the Weissenberg number, defined as the product of strain rate $\dot{\varepsilon}$ and the conformational relaxation time $\lambda$, is greater than 1 (Larson and Mead, 1993). Despite the high strain rates ($10^5$-$10^6$ s$^{-1}$) commonly observed in polymer solution jets during electrospinning, high degrees of alignment are usually difficult to achieve. This difficulty is likely due to the rapid solidification of electrospun fibers under typical spinning conditions, which does not give sufficient time for polymer chains to align (Inai et al., 2005; Zong et al., 2002). In some embodiments, under the presently disclosed electrostretching conditions, the alginate solution is collected without significant solvent evaporation, and the solution jet has an estimated strain rate $\dot{\varepsilon}$ of 10-70 s$^{-1}$. Although the strain rate is not very high, it is compensated by the long relaxation time due to the high molecular weight of alginate and PEG. Thus, the mechanical shear induced by the rotating collection plate can significantly contribute to the higher degree of alignment of the polymer chain. This analysis is supported by the observation that a faster rotating velocity leads to fibers with higher tensile modulus, indicating a higher degree of alignment enhanced by stronger mechanical stretching (FIG. 6).

The Young's modulus of wet fibers increased with the angular velocity of the rotating collection plate. These results suggest that a higher degree of mechanical stretching—under a higher angular velocity of the rotating collection plate—induces a higher degree of polymer chain alignment, manifested by a higher Young's modulus.

Without wishing to be bound to any one particular theory, it is thought that the efficacy of the presently disclosed method also relies on an effective crosslinking or fixation of the induced polymer chain alignment. The presently disclosed subject matter provides different crosslinking strategies that are applicable for a wide selection of biopolymers. These crosslinking methods also are complementary so that it is possible to prepare blended fibers having different compositions to afford multi-functionalities—a feature particularly suitable for regulating cell adhesion, tissue compatibility, permeability, and surface conjugation of ligands.

Further, the biodegradability of the presently disclosed fibers can be tailored by blending polymers with different degrees of sensitivity to hydrolysis and degradative enzymes. In some embodiments, the degradation can be triggered on demand. In some other embodiments, alginate fibers can be dissolved by treating the fibers with sodium citrate solution. In further embodiments, fibrin fibers can be degraded by plasmin and HA fibers can be degraded by hyaluronidase.

In some embodiments, the entire fiber spinning and crosslinking process is conducted in aqueous solutions under ambient conditions, making it amenable to cell encapsulation inside hydrogel fibers. In particular, the low electric potential (2-6 kV) in contrast to electrospinning and low mechanical shear ensure high cell viability in hydrogel fibers.

In some embodiments, the hydrogel fibers generated by the presently disclosed electrostretching method exhibit excellent mechanical properties while maintaining sufficient porosity and water content (>90%, usually 98%-99%). This characteristic is in contrast with hydrogel fibers prepared by simple extrusion, in which case polymer solutions are pressed through a small orifice and crosslinked during or after extrusion. Hydrogel fibers produced by the extrusion method do not exhibit a high degree of polymer chain alignment (FIG. 3c), and are therefore mechanically weaker and more challenging to handle than hydrogel fibers produced by electrostretching. Although this limitation in extruded fibers can be overcome by lowering the water content and increasing crosslinking density, these denser fibers are not suitable for cell encapsulation. The porosity of the electrostretched hydrogel fibers also can be easily tuned by varying the input polymer concentration, composition and crosslinking density.

Accordingly, the presently disclosed subject matter provides methods to generate hydrogel microfibers with a high degree of polymer chain alignment induced by a combination of electrical and mechanical stretching, and facilitated by the long polymer chain relaxation time, and effective crosslinking schemes. Using this concept, internally aligned hydrogel microfiber bundles of calcium alginate, fibrin, gelatin, hyaluronic acid, collagen and their blends have been produced. These microfibers exhibit enhanced mechanical properties as a result of the polymer chain alignment while maintaining high water content and porosity. The facile preparation conditions are conducive to cell encapsulation in generating "cellular strings." Due to their biodegradable nature and unique geometry and surface topography, they are ideal scaffold candidates for generating aligned tissue structures The development of these new hydrogel fibers represents an important step toward successful fabrication of hierarchically organized cellular structures in 3D.

Examples of Microvascular Structures

The invention can be further understood in view of the following non-limiting examples.

Cell Culture

Unless indicated otherwise, the following cells and culture conditions were used in the experiments. Human ECFCs (Lonza, Walkersville, MD) were used for experiments between passages 5 and 9. ECFCs were expanded in flasks coated with type I collagen (BD Biosciences, Franklin Lakes, NJ) in Endothelial Basal Medium-2 (EBM-2; Lonza) supplemented with EGM-2 Bulletkit (Lonza) and 10% fetal bovine serum (FBS; Hyclone, Logan, UT). ECFCs were fed every other day, passaged every 5 to 7 days with 0.05% trypsin/0.1% ethylenediaminetetraacetic acid (EDTA; Invitrogen, Carlsbad, CA). Human vSMCs (ATCC, Manassas, VA) were used between passages 4 and 9 and cultured in F-12K medium (ATCC) supplemented with 0.01 mg/ml insulin (Akron Biotech, Boca Raton, FL), 10% FBS (Hyclone), 0.05 mg/ml ascorbic acid, 0.01 mg/ml transferrin, 10 ng/ml sodium selenite, 0.03 mg/ml endothelial cell growth supplement, 10 mM HEPES, and 10 mM TES (all from Sigma-Aldrich, St. Louis, MO). Human placental pericytes (Promocell, Heidelberg, Germany) were cultured in Pericyte Growth Media (Promocell) and used between passages 7 and 10. Media was changed every other day and cells were passaged every 5 to 7 days with 0.05% trypsin.

Immunofluorescence Staining and Confocal Microscopy Imaging

Cell-microfiber constructs were fixed with 3.7% formaldehyde (Fisher Chemical, Fairlawn, NJ) for 15 min, permeabilized with 0.1% Triton X-100 solution (Sigma-Aldrich) in 3.7% formaldehyde for 10 min, washed three times with PBS, and incubated for 1 h at room temperature with the indicated primary antibodies (Table 1). After rinsing with PBS three times, samples were then incubated with the appropriate secondary antibodies or conjugated phalloidin (Table 1) at room temperature for 1 h. Samples were then rinsed with PBS three times, and counterstained with DAPI for 10 min. Z-stack and cross-sectional images were obtained and processed using confocal microscopy (LSM 510 Meta, Carl Zeiss Inc., Thornwood, NY). Epifluorescence images were obtained using an Olympus® BX60 microscope.

TABLE 1

Antibodies Used in the Studies

| Reagent Type | Name | Host | Vendor | Dilution |
|---|---|---|---|---|
| Microtubule disrupting agent | Nocodazol | NA | Sigma-Aldrich | 3.3 µM |
| Actin disrupting agent | Cytochalasin D | NA | Sigma-Aldrich | 1 ug/mL |
| Primary Antibody | CD31 | mouse | Dako | 1:100 |
| | vWF | mouse | Dako | 1:100 |
| | VEcad | mouse | Santa Cruz Biotechnology | 1:100 |
| | SM22 | rabbit | Abcam | 1:200 |
| | Collagen I | mouse | Abcam | 1:100 |
| | Collagen III | mouse | Santa Cruz Biotechnology | 1:100 |
| | Collagen IV | rabbit | Santa Cruz Biotechnology | 1:100 |
| | Elastin | mouse | Abcam | 1:100 |
| | Fibronectin | rabbit | Sigma-Aldrich | 1:100 |
| | Laminin | rabbit | Abcam | 1:100 |
| Conjugated Antibody | DAPI | NA | Roche Diagnostics | 1:1000 |
| | Alexa Fluor 488 Phalloidin | shroom | Invitrogen | 1:50 |
| Secondary antibody | Alexa Fluor 488 anti rabbit IgG | goat | Invitrogen | 1:500 |
| | Alexa Fluor 546 anti mouse IgG | donkey | Invitrogen | 1:500 |
| | Alexa Fluor 546 anti rabbit IgG | donkey | Invitrogen | 1:500 |
| | Alexa Fluor 647 anti rabbit IgG | donkey | Invitrogen | 1:500 |

Transmission Electron Microscopy

Samples were prepared for transmission electron microscopy (TEM) analysis as described previously (Hanjaya-Putra et al., Blood, 2011; 118: 804-815). Briefly, samples were fixed with 3.7% formaldehyde, 1.5% glutaraldehyde in 0.1 M sodium cacodylate, 5 mM $CaCl_2$, and 2.5% sucrose at room temperature for 1 h and washed 3 times in 0.1 M cacodylate/2.5% sucrose (pH 7.4) for 15 min each. The cells were post-fixed with Palade's $OsO_4$ on ice for 1 h, en bloc stained with Kellenberger uranyl acetate overnight, dehydrated through a graded series of ethanol, and then embedded in EPON™ epoxy resin. Sections of 80 nm were cut, mounted onto copper grids, post-stained in 2% uranyl acetate and Reynolds lead citrate, and viewed using a Phillips® EM 420 transmission electron microscope (FEI). Images were captured with an Olympus® Soft Imaging Systems Megaview III CCD digital camera.

Scanning Electron Microscopy

Hydrogel microfiber samples were first serially dehydrated in 50%, 60%, 70%, 80%, 90%, 95% and 100% ethanol for 15 min in each solution, critical point dried, and then sputter-coated with 8 nm thick Au/Pd (gold/palladium particles). Samples were imaged on a field-emission scanning electron microscopy (SEM) (JEOL 6700F, Tokyo, Japan).

Image and Statistical Analyses

The cell areas and perimeters were measured by fitting an ellipse to each cell using the LSM 510 software. Cytoskeletal alignment angle was calculated by measuring the angle between the long axis of each ellipse and the longitudinal axis of the microfiber, found by drawing a line at the edges of the microfiber in its image projection. ECM angle of orientation was measured using the LSM 510 software by drawing a line following the ECM deposition and finding the angle between the line and the longitudinal axis of the microfiber. Graphs were plotted with 5-95% confidence intervals. Unpaired two-tailed Welch-corrected t-tests were performed where appropriate (GraphPad Prism® 5.01, GraphPad Software, San Diego, CA). Significance levels were determined between samples examined and were set at *$p<0.05$, $p<0.01$, and *$p<0.001$.

Example 7 ECFC Attachment and Alignment on Fibrin Microfibers

A new approach to create aligned hydrogel microfibers using an electrostretching process of polymer materials is disclosed. Unique characteristics of the electrostretched hydrogel microfibers are the internal and topographical alignment of the fibrous structure, generated as a result of both electrical field and mechanical shear-induced polymer chain alignment as described above. Furthermore, the diameter of a microfiber is controlled and uniform as a result of the bundling and processing of the individual nanofibers that compose the hydrogel microfibers. Fibrin gels have been extensively used to study microvasculature assembly (Dickinson L E, et al., Soft Matter, 2010; 6: 5109-5119; Bayless, K J, and Davis, G E, Biochemical and Biophysical Research Communications, 2003; 312: 903-913; Davis G E, and Bayless K J, Microcirculation, 2003; 10: 27-44; Bayless K J, et al., RGD-Dependent American Journal of Pathology, 2000; 156: 1673-1683; Dickinson L E, et al., Lab Chip, 2012; 12: 4244-4248), vSMC responses (Ahmann K A, et al., Tissue Eng Part A, 2010; 16: 3261-3270; Long J L, and Tranquillo R T, Matrix Biol, 2003; 22: 339-350) and multicellular organization (Lesman A, et al., Biomaterials, 2011; 32: 7856-7869). Fibrin is used as the matrix material to prepare hydrogel microfibers as a template for the step-wise creation of microvasculature of the invention.

Preparation of 3D Fibrin Hydrogel Microfiber

Fibrin hydrogel microfibers were generated by the electrostretching method (FIG. 1A). An aqueous solution of 1.5 wt % alginate (Sigma-Aldrich) was in-line mixed with 2 wt % fibrinogen (Sigma-Aldrich) at feeding rates (flow rates) of 2 ml/h and 1 ml/h, respectively. Both solutions were dissolved in 0.2 wt % poly(ethylene oxide) (PEO) (Mw=4,000,000, Sigma-Aldrich) prior to spinning. The mixed solution was then charged with 4 kV electric potential and extruded through a 25-gauge needle. The fibrinogen-alginate solution jet was collected, at a distance of about 3-5 cm from the needle tip, in a grounded, rotating bath (20 cm diameter, 20-40 rotation/min) containing 50 mM $CaCl_2$ solution with 5 units/ml thrombin (Sigma-Aldrich) as a cross-linking solution (FIG. 7). After spinning, fibers were left in the collection solution for 15 min. To generate microfibers with different diameters, collection times were varied from 7-80 min, including 7, 10, 15, 17, 20, 22, 26, 27, 35, 40, 45, 50, 55, 60, 70, 75, and 80 min. The crosslinked fibrin-alginate fibers were then soaked in 0.2 M sodium citrate overnight to remove calcium ions and dissolve alginate. Fibers were soaked in water for 30 min to remove sodium citrate, stretched manually to about 150% of their initial length by placing the ends of the microfiber on supports such as pipettes and extending the supports to for example 150% of their original distance, and air-dried for 30 min. Fibers were wrapped around a custom-made plastic frame, then sterilized by soaking in 75% ethanol for 2 min followed by rinsing twice with sterile water. Microfiber diameter was measured from confocal Z-stack projections.

Cell Seeding and Culture on Fibrin Hydrogel Microfibers

ECFCs were seeded on microfibers of 15-cm length total at a density of $4\times10^5$ cells/ml in 5 ml of ECFC media supplemented with 50 ng/mL of VEGF (Pierce, Rockford, IL, USA). The seeding tube was continuously rotated on a tumbler (Labquake, Dubuque, Iowa) for 24 h at 37° C. to facilitate cell attachment. Frames with ECFC seeded microfibers were then transferred to 35 mm Petri dishes using tweezers, and cultured in the same media in a $CO_2$ incubator at 37° C. Media was refreshed every other day thereafter.

Results

Using the electrostretching method, fibrin hydrogel microfibers exhibited longitudinally-aligned nanotopography (FIG. 7a). This is an important feature as sub-micron (<1 μm, but greater than 100 nm) scale topographic features have been shown to increase EC adhesion, migration and orientation (Ranjan A, and Webster T, *Nanotechnology*, 2009; 20: 305102; Liliensiek S, et al., *Biomaterials*, 2010; 31: 5418-5426; Bettinger C J, et al., *Adv Mater*, 2008; 20: 99-103; Lu J, et al., *Acta Biomater*, 2008; 4: 192-201).

The seeding of ECFCs was facilitated by continuous rotation (FIG. 7a). After 24 hrs, ECFCs attached to the microfibers throughout the surface (FIG. 7e). Within 5 days in culture, ECFCs were found to be elongated and aligned longitudinally with the microfibers as indicated by F-actin staining (FIG. 7b-d). ECFCs covered the microfiber surface continuously, and exhibited typical membrane expression of endothelial markers VEcad and CD31 (FIG. 7b, 7d), and cytoplasmic expression of von Willebrand factor (vWF) (FIG. 7c), demonstrating that fibrin microfibers support the adhesion and culture of ECFCs.

Example 8 ECM Deposition from ECFCs on Fibrin Microfibers

While the importance of ECM deposition in vascular development has been recognized, few studies have looked at ECM production by the endothelium. ECFCs deposit collagen IV, fibronectin and laminin in an organized web-like structure when cultured on Petri dishes (Kusuma S, et al., *FASEB J*, 2012; 26: 4925-4936). To establish a reliable in vitro model of microvasculature, we characterized the ECM protein deposition by the endothelium on hydrogel microfibers. ECFCs were seeded on fibrin hydrogel microfibers as described in Example 7.

Figure 8A:
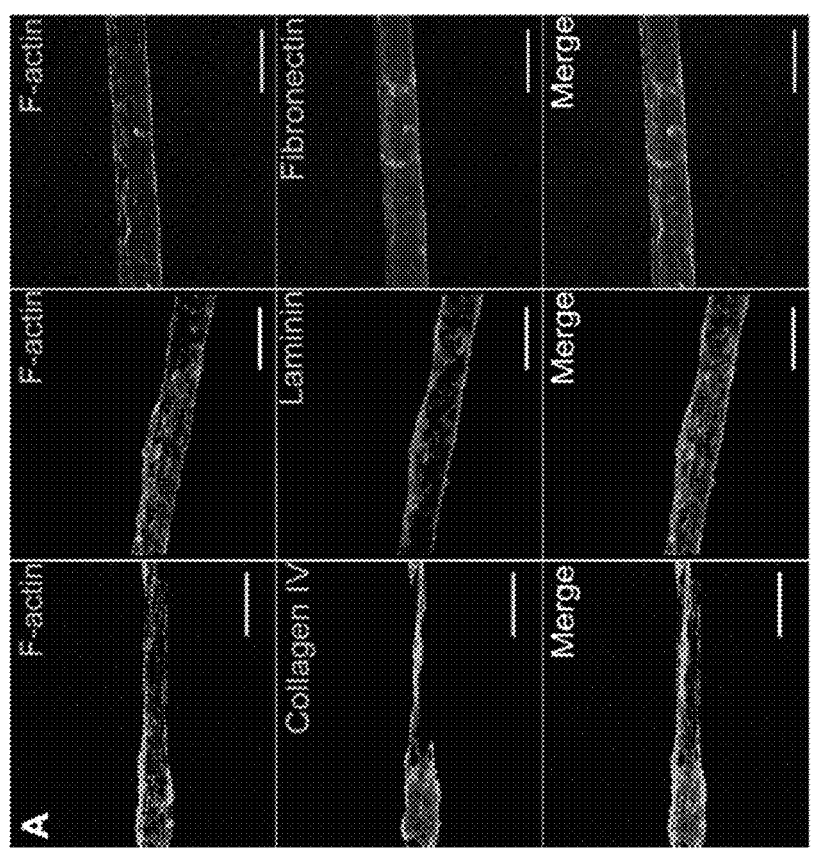
Figure 8B:
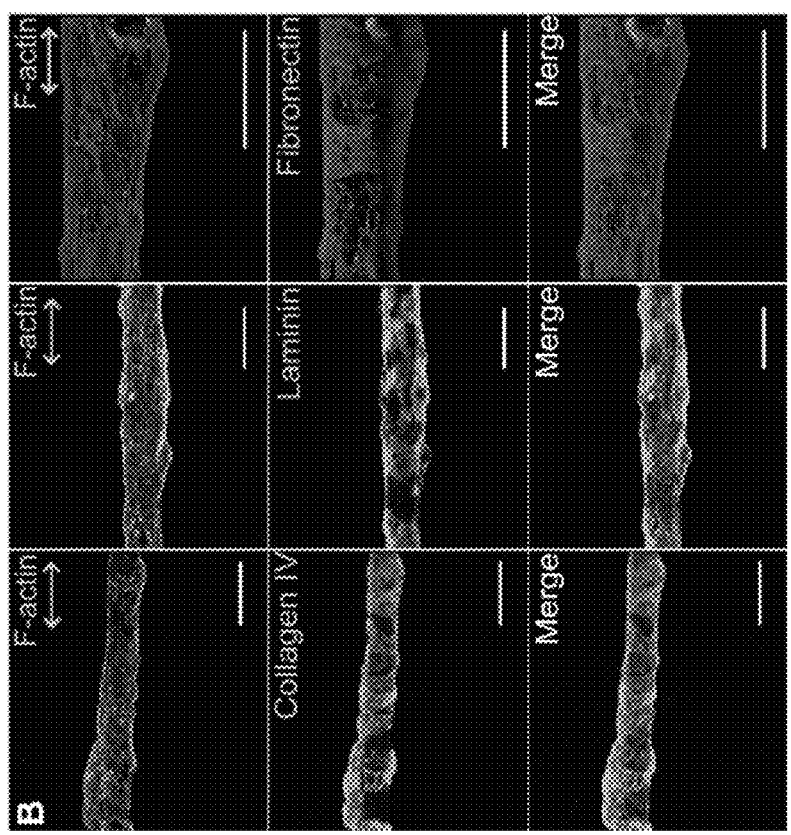
Figure 8C:
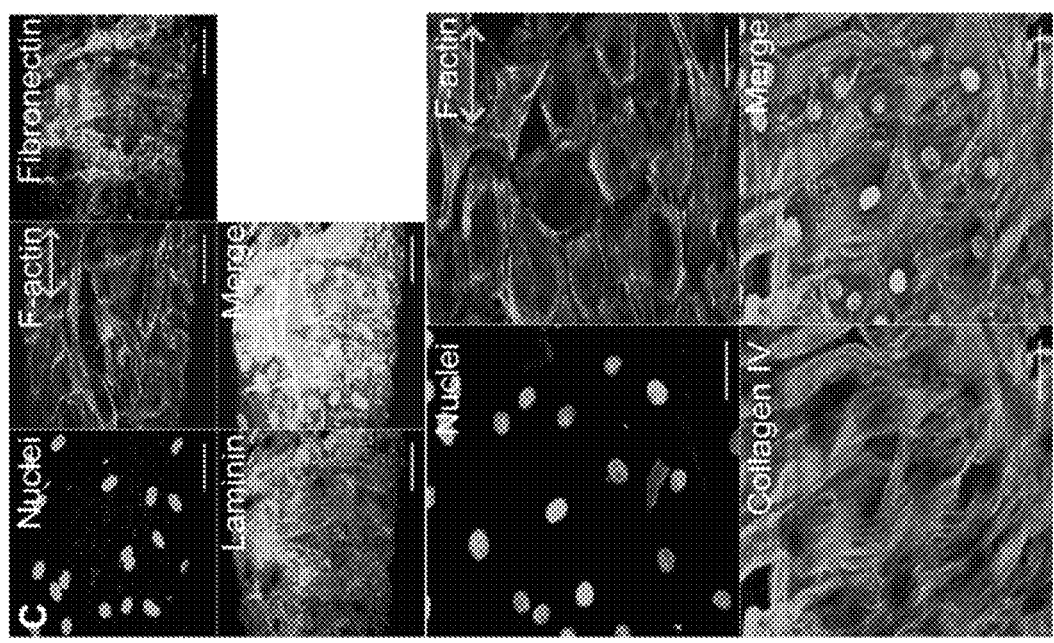
Figure 8E:
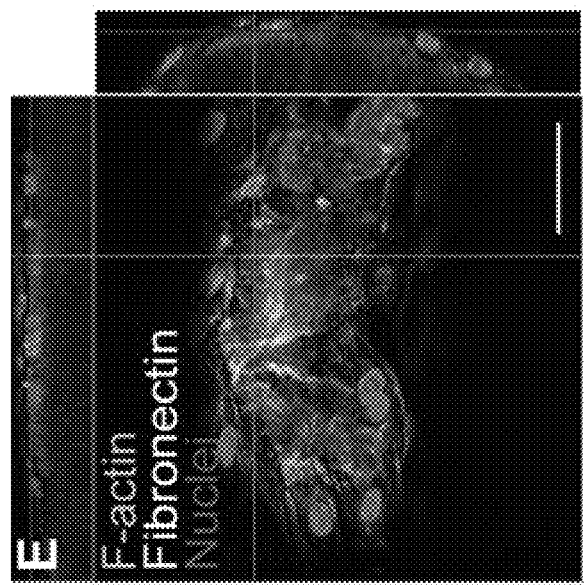
Figure 8D:
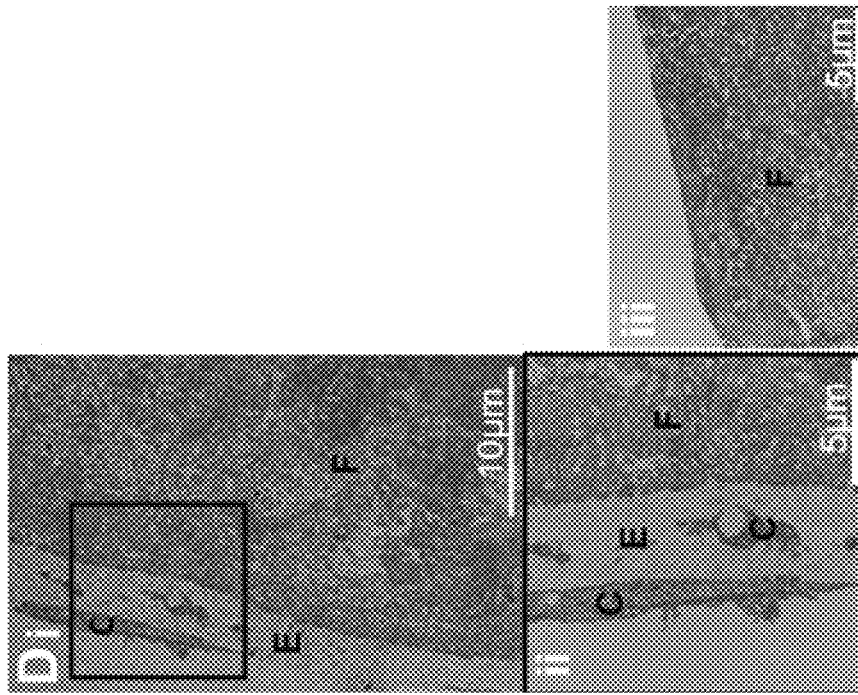
Figure 8F:
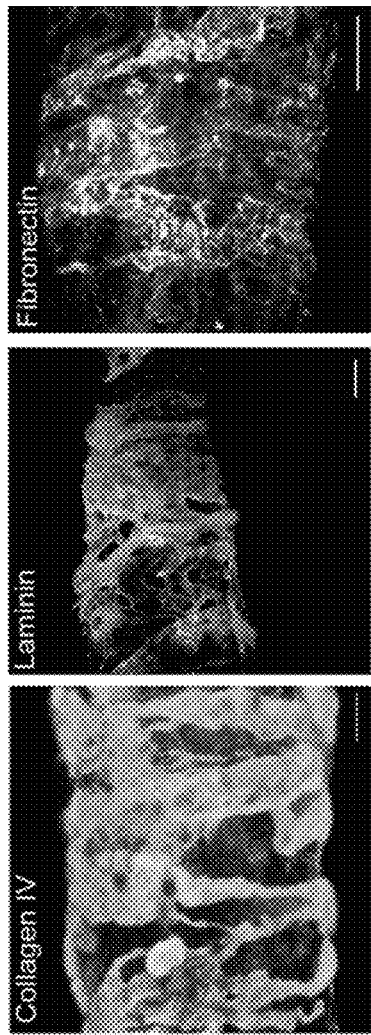
Figure 8G:
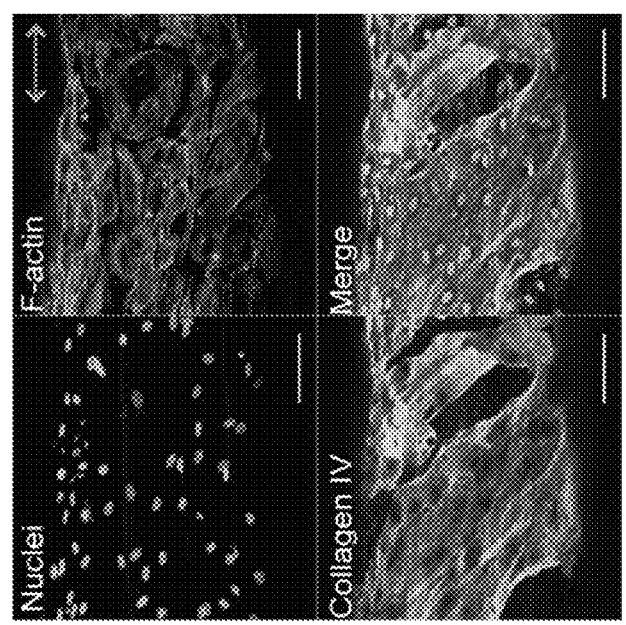

ECFC seeded on fibrin microfibers deposited laminin, collagen IV, and fibronectin after one day in culture (FIG. 8a). On Day 5, ECFCs completely covered the fibrin microfiber, and abundant ECM deposition was observed (FIG. 8b). In contrast to what was observed previously on Petri-dishes (Kusuma S, et al., *FASEB J*, 2012; 26: 4925-4936), the ECM proteins deposited by ECFCs on hydrogel microfibers were organized. ECM proteins laminin, collagen IV, and fibronectin wrapped around the microfibers, perpendicular to the EC orientation, along the microfiber's circumference, as observed in FIGS. 8c, 8f, and 8g. This is in contrast to the web-like structure observed on Petri-dishes. Specifically, on fibrin microfibers, the individual collagen IV nano-fibrils also seem to follow this macroscopic circumferential alignment at the nano-scale, with fibrils being deposited next to each other in an aligned manner to create a ribbon of circumferentially aligned collagen (FIG. 8c, 8g). Further analysis revealed this was also true for microfibers of sizes up to about 370 μm, and that the largest microfibers tested (about 445 μm) did not have a distinguishable collagen nano-fibril orientation (FIG. 8d-f). On Petri-dishes, ECM nano-fibrils were deposited without any apparent alignment, in a web-like structure formation (Kusuma S, et al., *FASEB J*, 2012; 26: 4925-4936). Moreover, these ECM structures appeared to be distributed either below or among the ECFCs (FIG. 8d-e), resembling basal lamina organization found in native microvessels. It should be noted that similarly to what we observed on Petri-dishes (Kusuma S, et al., *FASEB J*, 2012; 26: 4925-4936), ECFCs did not express or deposit Collagen I (data not shown).

Example 9 ECM Deposition from ECFCs on Fibrin Sheets and PES Fibers

It was previously demonstrated that line-grating topography influences EC adhesion, alignment, and elongation (Ranjan A, and Webster T, *Nanotechnology*, 2009; 20: 305102; Liliensiek S, et al., *Biomaterials*, 2010; 31: 5418-5426; Bettinger C J, et al., *Adv Mater*, 2008; 20: 99-103; Lu J, et al., *Acta Biomater*, 2008; 4: 192-201). To probe if the aligned nanotopography on fibrin microfibers is responsible for ECFC alignment and coordinated deposition of laminin, collagen IV, and fibronectin, we first examined their deposition on flat (2D) fibrin sheets with similar aligned nanotopography (FIG. 9e) as the fibrin hydrogel microfibers by varying the dimensionality and cylindrical shape of the scaffold.

Preparation of 2D Fibrin Nanofiber Sheets

Fibrin-alginate hydrogel nanofibers were prepared according to the same electrostretching method as described in Example 1 above until the collection step in a rotating bath. The collected fibrin-alginate hydrogel nanofibers were then wrapped around a modified plastic frame to form a sheet of hydrogel nanofibers while slightly stretching the nanofibers to ensure proper alignment. The fibrin nanofiber sheets were placed in a 0.2 M sodium citrate solution overnight to remove alginate, followed by a 30 min wash in water to remove excess sodium citrate. Fibrin nanofiber sheets were then sterilized with 75% ethanol and rinsed twice with sterile water. The resulting nanofiber sheets are distinct from microfibers as these are not bundled, stretched, and air-dried to form a microfiber, but instead are collected from the rotating bath in a 2D nanofiber sheet formation.

Cell Seeding and Culture on 2D Fibrin Sheets

Cells were seeded by placing $5\times10^5$ ECFCs in a concentrated solution of cells (about $2\times10^6$ cells/ml) directly on top of the fibrin nanofiber sheet. After 5 min the cell solution that had filtered through the sheets was collected and reseeded on top of the fibrin nanofiber sheets. This process was repeated 3 times, after which the same culture media as used for 3D fibers was added to the samples before they were placed in a humidified incubator at 37° C. in a 5% $CO_2$ atmosphere. Media was refreshed every other day up to 5 days of culture.

Preparation of 3D Polyethersulfone Fibers

Solid polymer fibers were prepared as a control according to a modified electrospinning protocol. In brief, polyethersulfone (PES) (Goodfellow Cambridge Limited, UK, Mw 55,000) was dissolved in 30 wt % DMSO and electrospun under an electric potential of 5 kV. The feed rate of PES solution was 12 ml/h to initiate a polymer jet, which was collected in a grounded, rotating ethanol bath (20-40 rotations/min) to extract the solvent. The collection distance was set to 5 cm. After 10 min in ethanol, PES strings were removed from the bath and air-dried.

After electrospinning, PES fibers were wrapped around a seeding frame similarly to the fibrin hydrogel microfibers. Samples were then plasma-treated for 5 min before soaking for 5 min in a 10 units/ml thrombin in 15 mM $CaCl_2$ solution. Thrombin-coated PES fibers were then immersed in a 0.2% fibrinogen solution diluted in 0.9% NaCl for fibrinogen polymerization into fibrin. Excess fibrin coating on the frame and outside of the fibers was removed before sterilization with 75% ethanol for 1-2 min. Samples were rinsed twice with sterile water, after which cell seeding was performed similarly to the fibrin microfibers as described in Example 1.

Results

Figure 9A:
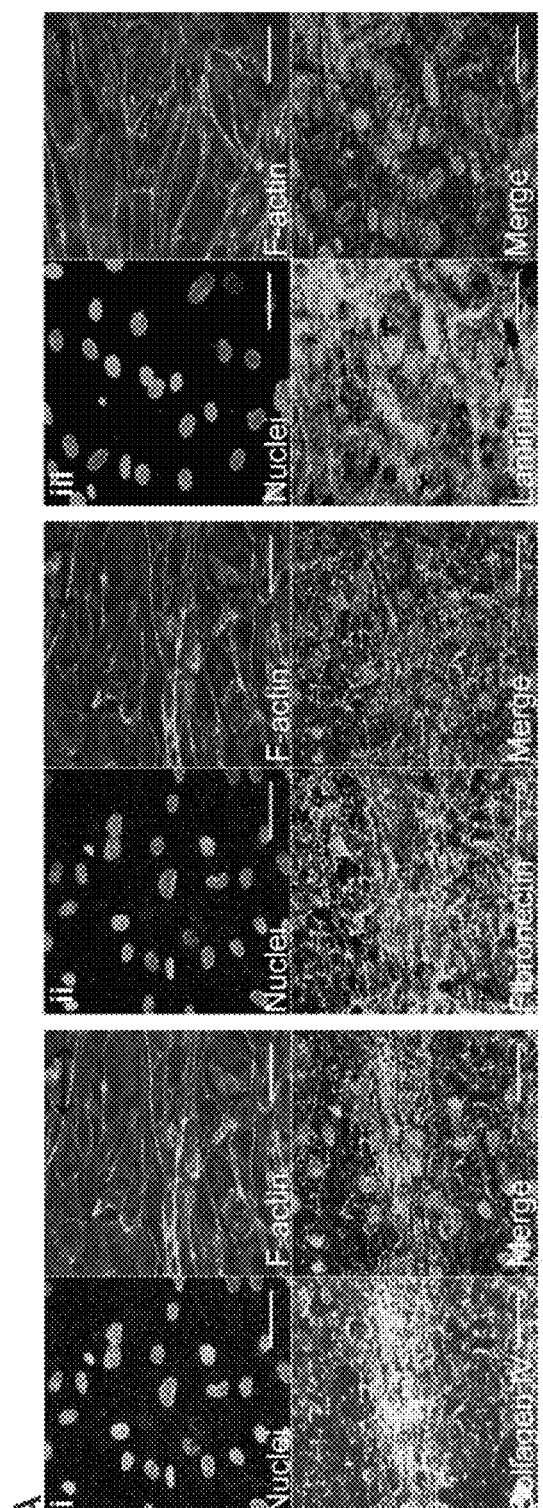

ECFCs seeded on fibrin nanofiber sheets were effectively aligned with the nanotopography. However, the collagen IV, fibronectin and laminin produced by ECFCs exhibited a random organization, as opposed to the perpendicular orientation with respect to cell alignment observed in the 3D microfibers (FIG. 9a). This result indicates that the microfiber geometry may be crucial to the specific organization of ECM molecules secreted by ECFCs.

Figure 9B:
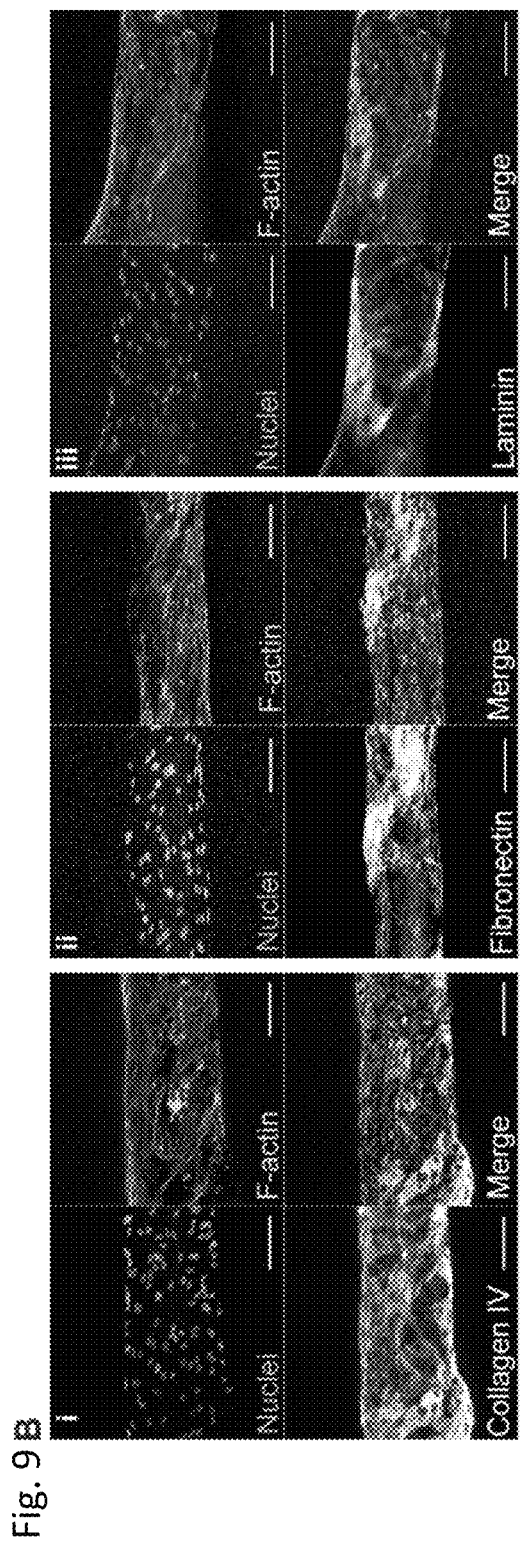

Similarly as observed in FIG. 8, ECFCs completely covered the PES microfibers and deposited ECM molecules after 5 days of culture (FIG. 9b). While ECFCs grown on the PES microfibers did not necessarily have a random orientation on the PES fibers, and in fact often exhibited a partial diagonal orientation (FIG. 9c), the ECFC-deposited ECM proteins were found to wrap around the PES microfiber in a similar manner to ECFC-deposited ECM on fibrin microfibers, as evidenced by measuring the angles between ECM ribbons and the fiber's longitudinal axis (FIG. 9d). Note that the average angle in both cases is close to 90 degrees, demonstrating perpendicular alignment, and that the distribution (represented by the height of the boxes and also shown as standard deviation in FIG. 9e) is small, signifying most ECM ribbons had an orientation close to 90 degrees.

Electrospun PES microfibers coated with fibrin used to generate microfibers maintain the dimensionality and geometry of the fibrin microfibers but with a random nanotopography (FIG. 9f). Before coating the PES fibers with fibrin, the surface of PES fibers is smooth (FIG. 9g (ii)), however, an uncoated PES fiber is not bioadhesive, and ECFC attachment after seeding is not detected (data not shown). Furthermore, PES fiber does not present the same bioactive substrate to the ECFCs as the fibrin fibers. Therefore, the PES fibers were coated with fibrin, resulting in the random, non-aligned nano-topography of coating presented in FIG. 9g (i). Such PES microfibers have a similar diameter (240±45 μm; data not shown) as fibrin microfibers and thus enables investigation of whether the uniaxial alignment topography contributes to the unique cellular activity and ECM organization.

Example 10 ECM Organization: Dependence on ECFC Alignment and Microtubule Organization Actin and microtubule disruption studies were used to determine whether ECFC actin filament alignment and microtubule organization through actin and tubulin configuration directs ECM organization. Cytochalasin D is an actin destabilizing agent, and nocodazole is a microtubule polymerization disturbing agent.

Cell Seeding and Culture

ECFCs were seeded on fibrin microfibers as described in Example 1 above.

Actin and Microtubule Disruption Studies

Cytochalasin D or nocodazole were dissolved in DMSO (Table 1). ECFCs were cultured on Petri dishes (control) or fibrin microfibers in ECFC media with 50 ng/mL of VEGF (Pierce, Rockford, IL, USA) supplemented with either 1 g/mL cytochalasin D or 3.3 M nocodazole, from either day 0 or day 1 after seeding. F-actin or α-tubulin organization and ECM deposition was analyzed after 1, 2, or 3 days of treatment. Final concentration of DMSO in cell culture medium was kept at 0.1% (v/v). Controls were treated with DMSO alone at the same concentration.

Results

Figure 10C:
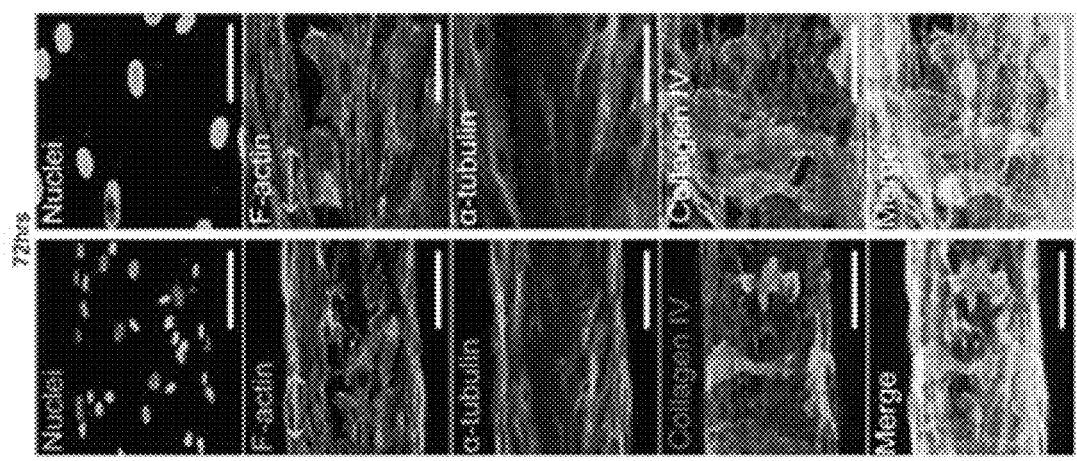
Figure 10B:
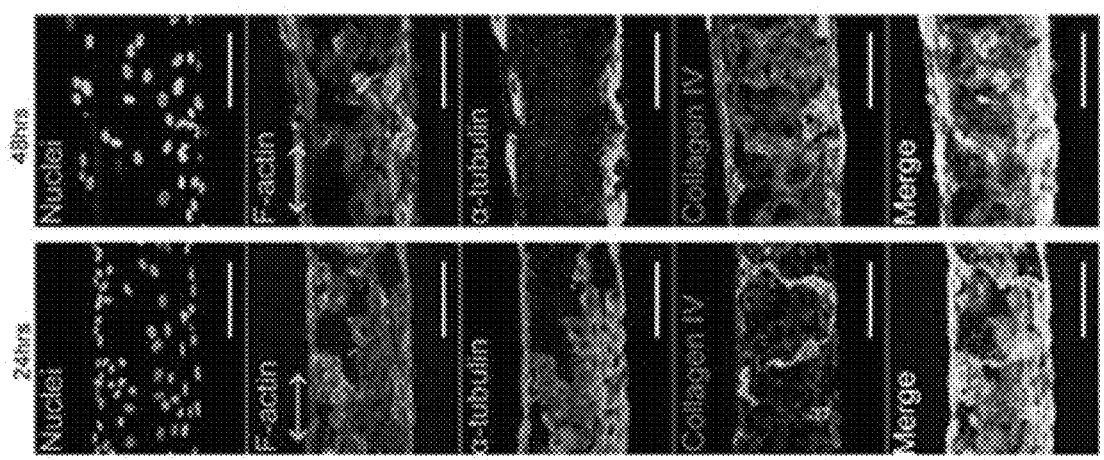
Figures 10D, 10E:
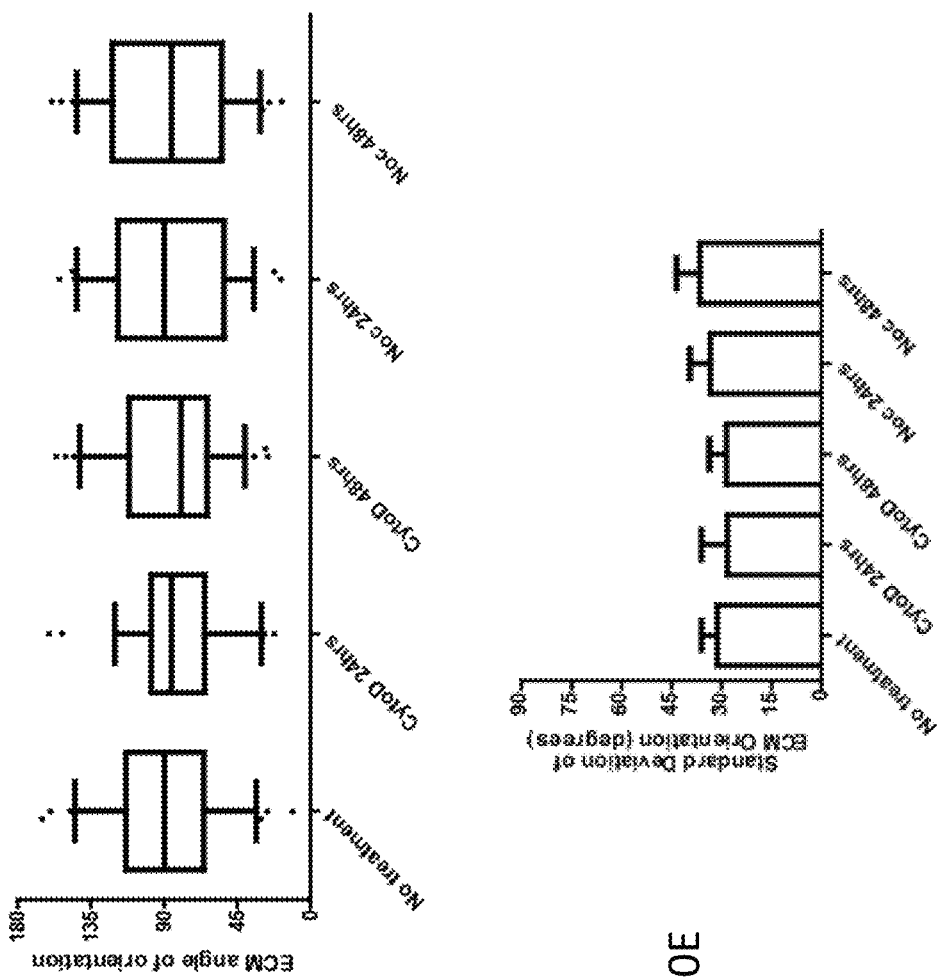
Figure 10F:
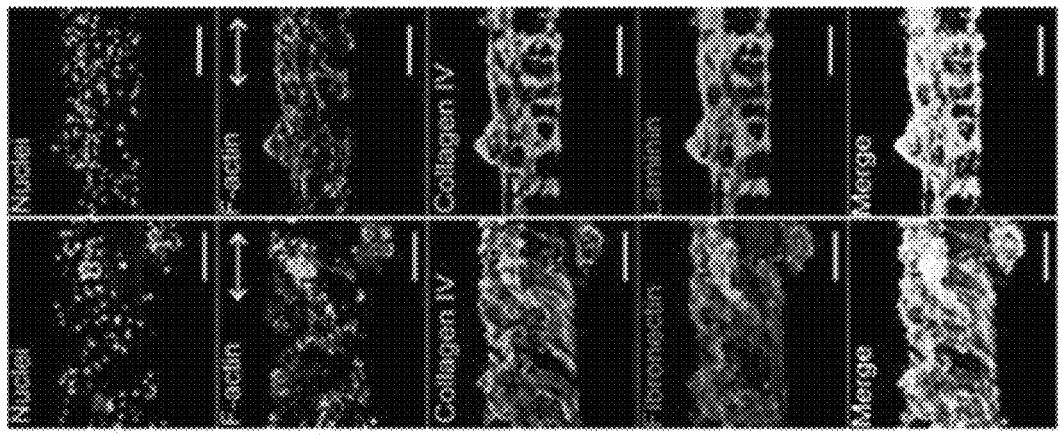
Figure 10G:
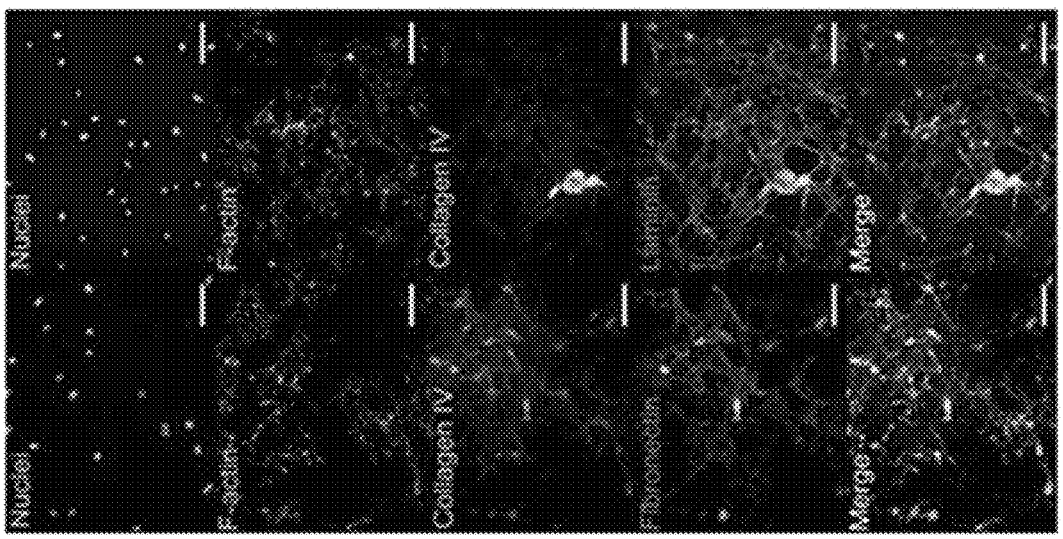
Figure 10H:
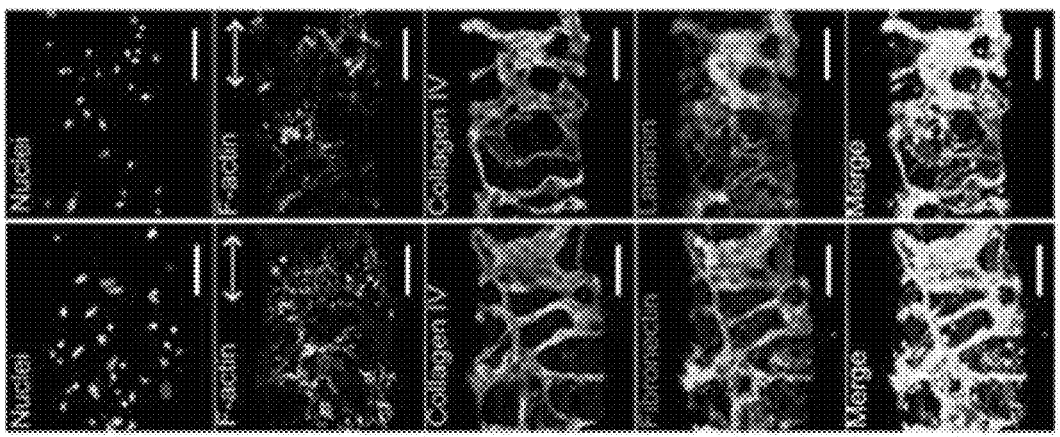

For Cytochalasin D added to the culture media at 24 h after ECFC seeding on microfibers, forty-eight hours after treatment the unique wrapping arrangement of the deposited ECM molecules around the fibrin microfibers still present after 24 and 48 hrs of treatment (FIG. 10a and FIG. 10f). No difference was found in the average angle of ECM orientation or in the variance of all angles measured (FIG. 10d-e). It should be noted that ECM deposition was observed also in control treatments of ECFCs in Petri dishes (FIG. 10g) and that similar organization of wrapping ECM was observed when cytochalasin D was applied through the entire 3 days of culture (FIG. 10h).

Figure 10I:
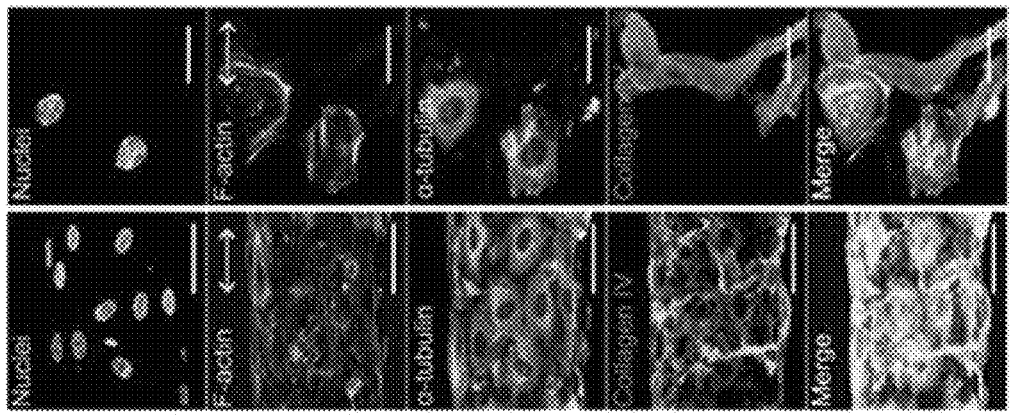
Figure 10J:
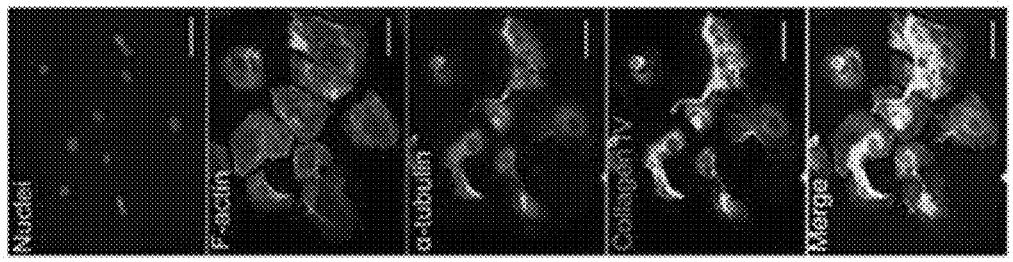
Figure 10K:
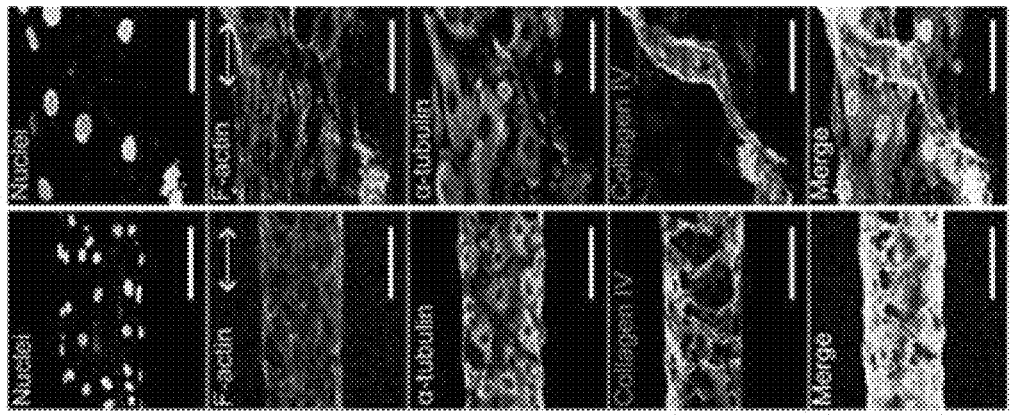

Likewise, when nocodazole, a microtubule polymerization disturbing agent, was added to the culture media at 24 h after ECFC seeding on microfibers, a similar ECM wrapping pattern was observed (FIG. 10b; FIG. 10i) even though microtubule formation was disrupted compared to samples with no drug treatment (FIG. 10c). Similarly, no difference was found in the average angle of ECM orientation or in the variance of all angles measured (FIG. 10d-e). In addition, ECM deposition was also observed in the 2D control group with the same treatment (FIG. 10j)), and similar organization of wrapping ECM was observed when Nocodazole D was applied through the entire 3 days of culture (FIG. 10k).

Overall, while treatment of ECFCs seeded on the nanopatterned microfibers with either cytochalasin D or nocodazole effectively altered actin and microtubule organization, respectively, it did not alter the wrapping organization of the deposited ECM molecules as compared to control cultures (FIG. 10). Also, even after only 3 days of culture when the endothelium layer was not always confluent and therefore the cell density was lower, ECM organization was still found to be circumferential (FIG. 10c-e, FIG. 10l-m).

Example 11 ECM Organization: Dependence on Microfiber Curvature

As indicated, the ECM organization is independent of the cytoskeleton organization of the ECFCs, but is influenced by the geometry of the microtubular structure. Here the diameter of the tubular structure to modulate the ECM organization was evaluated.

Preparation of Fibrin Hydrogel Microfiber

Hydrogel microfibers were prepared as in Example 1 above. Microfibers of different sizes were prepared by varying the collection time of the electrostretching process, thus changing the number of nanofibers in each microfiber bundle. Fibrin microfibers with an average diameter of 107.1±11.7 μm, 136.1±12.1 μm, 372.0±27.3 μm, and 443.4±30.6 μm were prepared. These microfibers were processed similarly and thus exhibited similar nanotopographical alignment, inducing alignment of ECFCs with the longitudinal axis of the microfibers on all sizes (data not shown).

Results

Figure 11A:
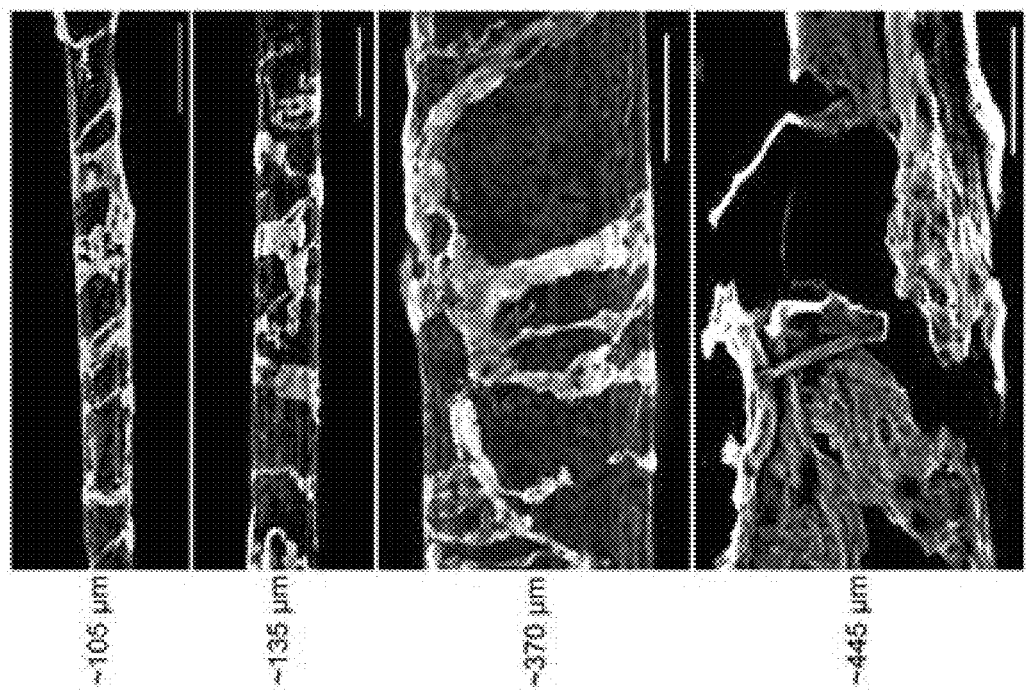
Figure 11C:
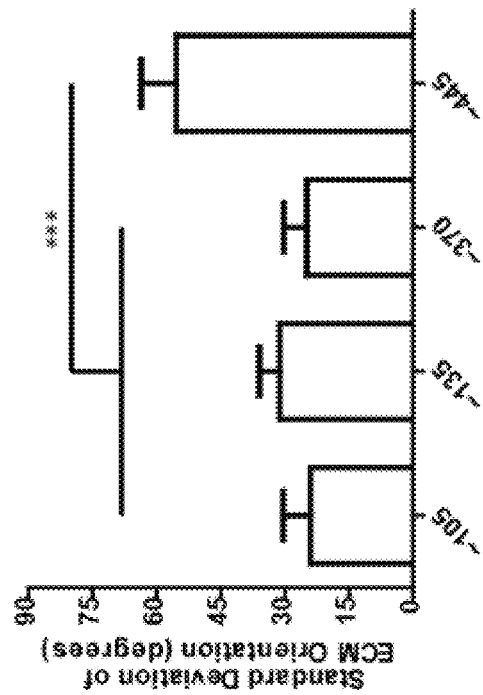
Figure 11B:
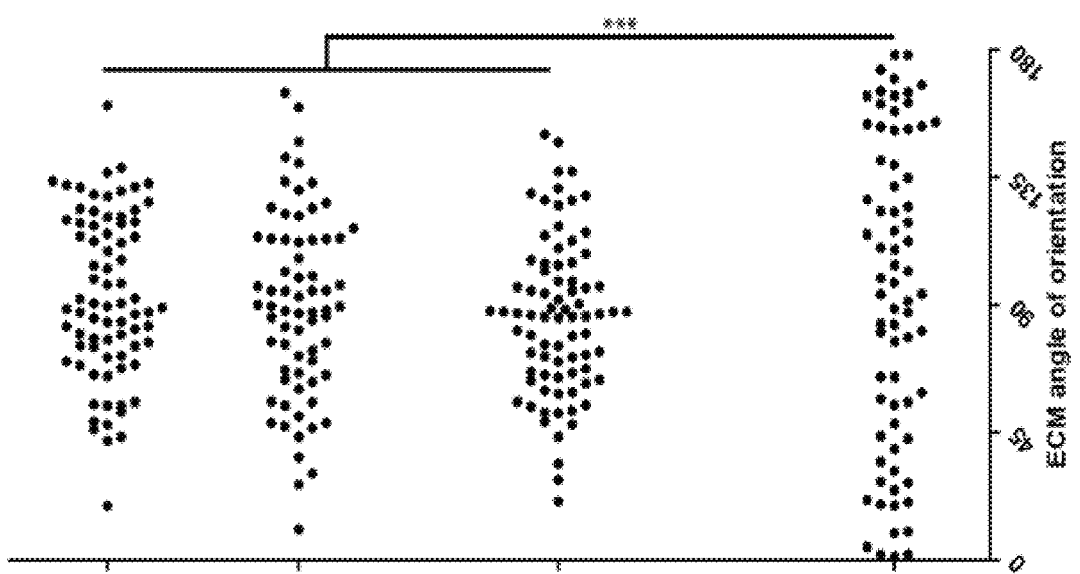

While seeded-ECFCs were confluent after 5 days in culture on all microfibers, decreasing organization of the ECM molecules was apparent as the fiber diameter increased (FIG. 11a). Measuring the angles between ECM ribbons and the microfiber's longitudinal axis revealed that microfibers with diameters smaller than about 400 μm had average angles close to 90° with a small distribution, signifying perpendicular orientation. On the largest diameter tested (avg. 452.1±26.7 μm), we observed a non-circumferential ECM organization as evidenced by a significant increase in the distribution of the angles between ECM ribbons and the fiber's longitudinal axis (FIG. 11b). Since the angle values measured range from 0° to 180°, a perfectly random distribution of angles would average to the mean of 90° as well. However, a sample with ECM wrapping would have most of these values close to 90°, having a small variance compared to a sample presenting random ECM orientation. Indeed, the largest microfibers resulted in ECM angles with a markedly higher standard deviation compared to the smaller microfibers (FIG. 11c).

Figures 11D, 11E, 11F:
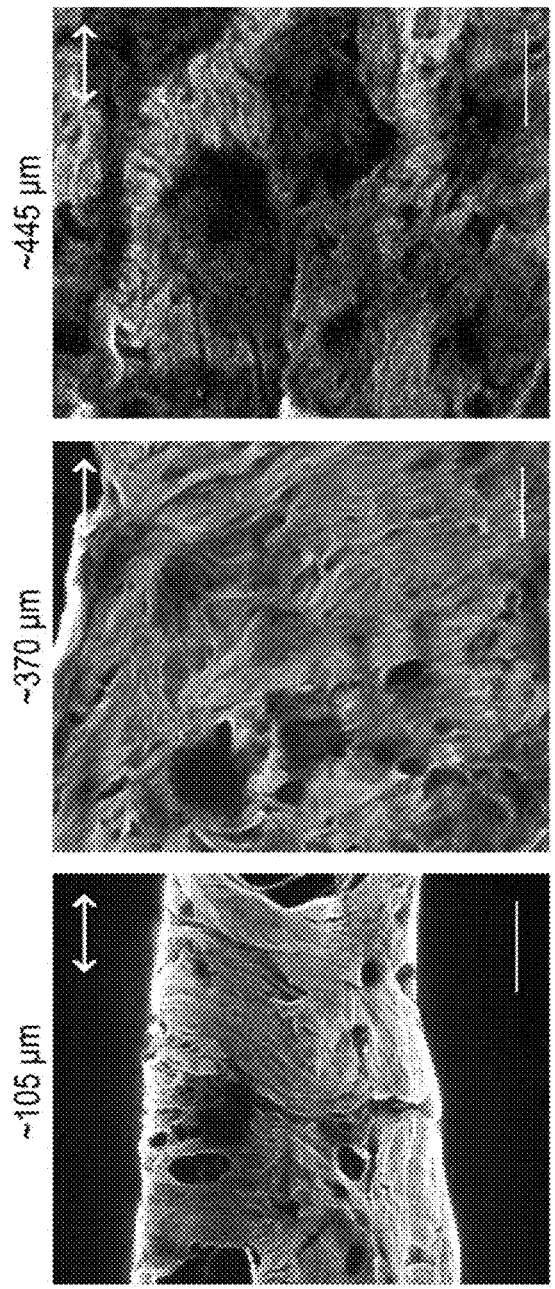

Also, when collagen IV has a wrapping organization, the individual collagen nano-fibrils also follow this macroscopic circumferential alignment at the nano-scale (FIG. 8c, 8g). This was also true for microfibers of about 105 μm to about 370 μm, and the largest microfibers tested (about 445 μm) did not have a distinguishable collagen nano-fibril orientation (FIG. 11d-f).

Example 12 vSMCs and Pericyte Attachment and New ECM Deposition on ECFC-Seeded Microfibers An advantage of the new fibrin microfiber system is the opportunity to co-culture mural cells, for example, vSMCs and pericytes, to study their interactions with the endothelial layer as well as the deposition of ECM component that compose the tunica media (Jain R K, Nat Med, 2003; 9: 685-693; Carmeliet P, Nature, 2000; 407: 249-257). Here, ECFC-seeded fibrin microfibers are co-cultured with vSMCs and/or pericytes to evaluate the effect on organization and ECM deposition.

Cell Seeding and Culture

ECFC-seeded fibrin hydrogel microfibers were prepared as described in Example 1 above.

Human vSMCs (ATCC, Manassas, VA) were used between passages 4 and 9 and cultured in F-12K medium (ATCC) supplemented with 0.01 mg/ml insulin (Akron Biotech, Boca Raton, FL), 10% FBS (Hyclone), 0.05 mg/ml ascorbic acid, 0.01 mg/ml transferrin, 10 ng/ml sodium selenite, 0.03 mg/ml endothelial cell growth supplement, 10 mM HEPES buffer, and 10 mM TES buffer (all from Sigma-Aldrich, St. Louis, MO).

vSMCs were seeded on 5-7 day ECFC-seeded fibrin microfibers at 1-4×10$^5$ cells/ml in 5 ml of 0.5% serum or regular ECFC media, tumbled for 24 hours, and then transferred to 35 mm Petri dishes to continue culture. Media was changed every other day thereafter.

Human pericytes (PromoCell, Heidelberg, Germany) were used between passages 5 and 9 and cultured in Pericyte Growth Media (PromoCell) according to manufacturer's instructions. Pericytes were seeded on 5 day ECFC-seeded fibrin microfibers at 4×10$^5$ cells/ml in 5 ml of ECFC media supplemented with 30 mM aminocaproic acid (to prevent fibrinolysis), tumbled for 24 hours, and then transferred to 35 mm Petri dishes to continue culture for 9 more days (10 days of co-culture total). Media was changed every other day.

Figures 12D, 12E:
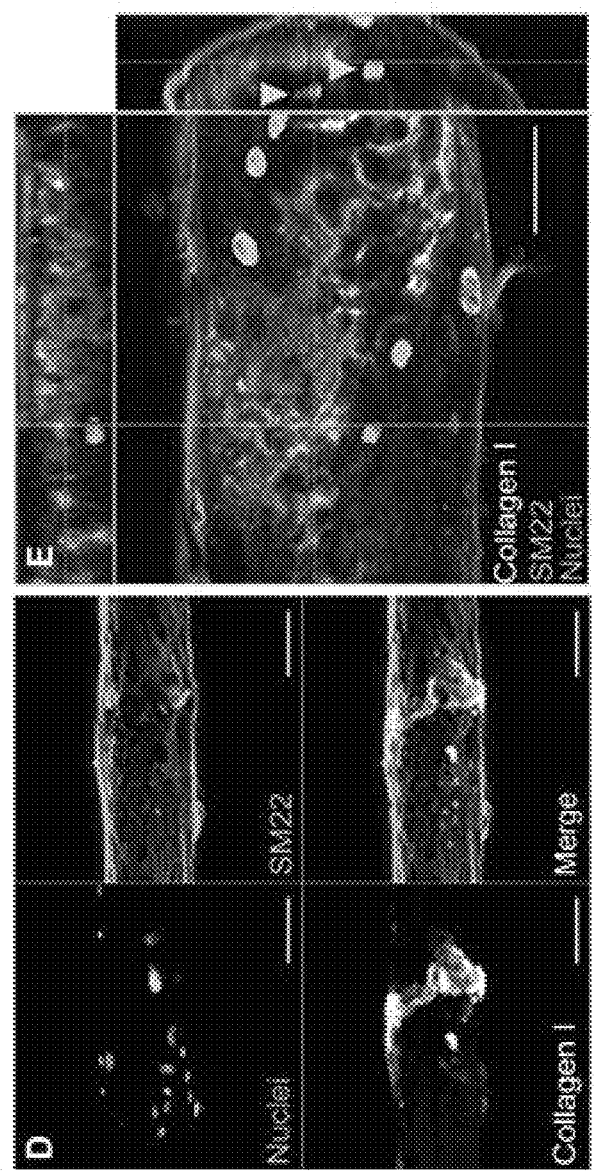
Figures 12F, 12G:
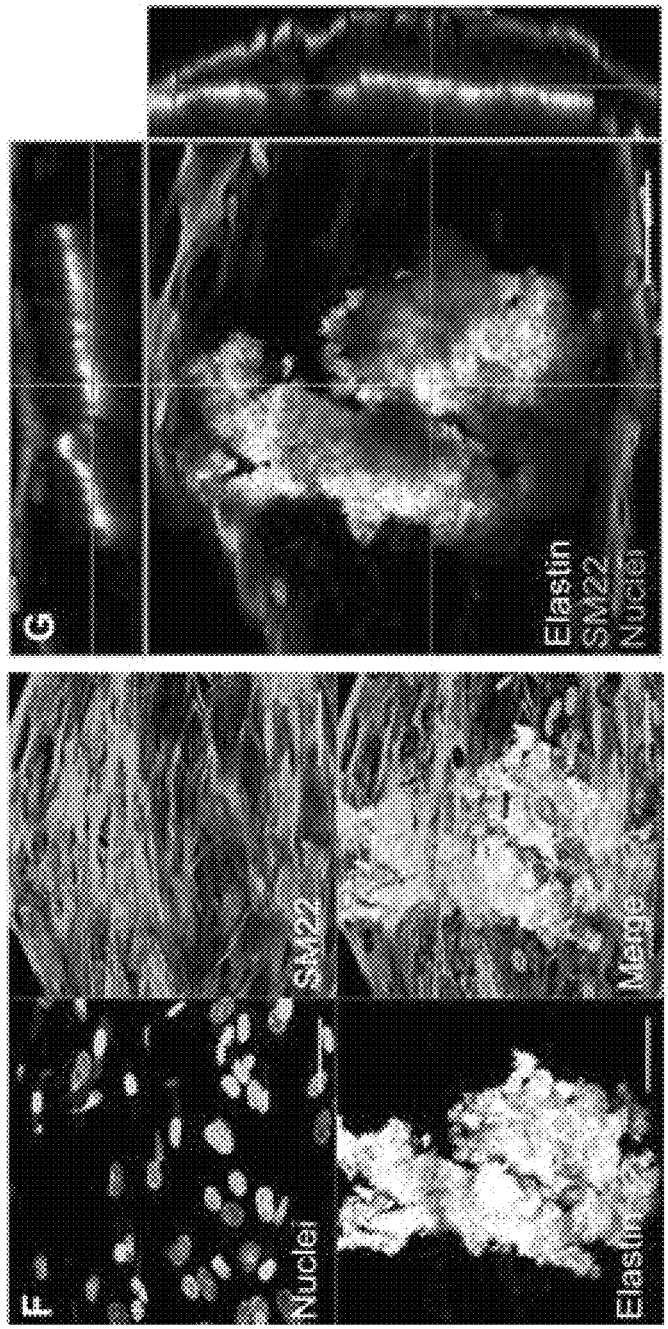

Results vSMCs seeded on ECFC-coated fibrin microfibers attached and grew on the ECFC layer, forming a bilayer cellular construct (FIG. 12a). Occasionally, vSMCs were found to have a random orientation on the structures (FIG. 12a), and in some instances they wrapped around the microfibers (FIG. 12b). However, more often they aligned with the longitudinal axis of the microfibers (FIG. 12c). vSMCs cultured for 3 and 5 days deposited collagen type I and elastin (FIG. 12d-g), located beneath the vSMC layer and above SM22 negative cells, the ECFCs (FIG. 12e, g).

Figures 13D, 13E:
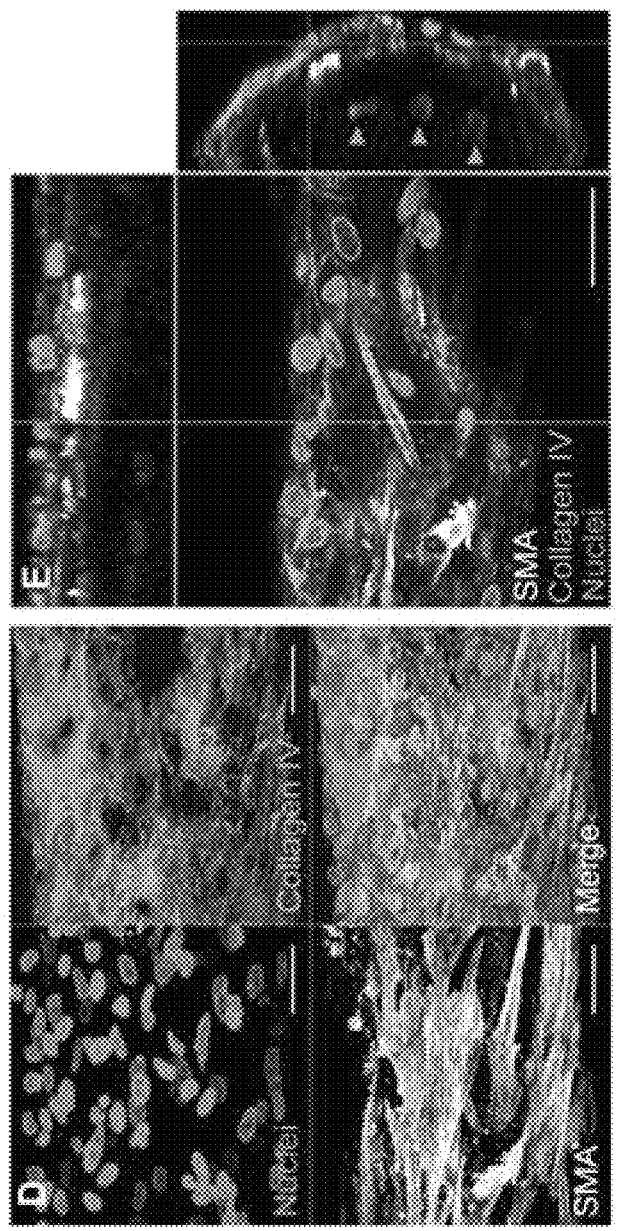

Pericytes cultured for 10 days on ECFC-seeded fibrin microfibers attached and grew on the microfiber scaffold, forming a multilayer cellular construct (FIG. 13). Pericytes either wrapped or aligned with the longitudinal axis of the microfibers (FIGS. 13a-c). Pericytes deposited collagen type IV, located beneath and in between the pericyte layer, and above the ECFCs (FIGS. 13d-e).

Example 13 3D Multicellular Microvascular Structure

Following the successful culture of different vascular cell types, namely ECFCs, pericytes, and vSMCs on fibrin microfibers, increased ECM protein production by the cells was investigated. Also, the fibrin core of the microfiber was degraded leaving both cellular and ECM formation intact, resulting in multicellular microvascular structures with a distinct circular lumen that recapitulate the multilayer organization found in native blood vessels.

Cell Culture

All cells were cultured in a humidified incubator at 37° C. and 5% $CO_2$. Human ECFCs (Lonza, Walkersville, MD) were cultured on collagen I (BD Biosciences, Franklin Lakes, NJ) coated flasks in Endothelial Basal Medium-2 (EBM-2; Lonza) supplemented with EGM-2 Bulletkit (Lonza) and 10% fetal bovine serum (FBS; Hyclone, Logan, UT) and used for experiments between passages 7 and 10. Media was changed every other day and cells were passaged every 5 to 7 days with 0.05% trypsin (Invitrogen, Carlsbad, CA).

Human vSMCs (ATCC, Manassas, VA) were used between passages 7 and 10 and cultured in F-12K medium (ATCC) supplemented with 0.01 mg/ml insulin (Akron Biotech, Boca Raton, FL), 10% FBS (Hyclone), 0.05 mg/ml ascorbic acid, 0.01 mg/ml transferrin, 10 ng/ml sodium selenite, 0.03 mg/ml endothelial cell growth supplement, 10 mM HEPES, and 10 mM TES (all from Sigma-Aldrich, St. Louis, MO). Media was changed every third day and cells were passaged every 5 to 7 days with 0.25% trypsin (Invitrogen).

Human placental pericytes (Promocell, Heidelberg, Germany) were cultured in Pericyte Growth Media (Promocell) and used between passages 7 and 10. Media was changed every other day and cells were passaged every 5 to 7 days with 0.05% trypsin.

Preparation of 3D Fibrin Hydrogel Microfiber

Fibrin hydrogel microfibers were generated by the electrostretching method described in Example 7. Briefly, 1.5 wt % alginate (Sigma-Aldrich) was mixed in-line with 2 wt % fibrinogen (Sigma-Aldrich) at flow rates of 2 ml/h and 1 ml/h, respectively. Both solutions were dissolved in 0.2 wt % polyethylene oxide) (PEO) (Mw=4,000,000, Sigma-Aldrich) prior to electrospinning. A 4 kV electric potential was applied to the solution before extrusion through a 25-gauge needle. The solution jet was collected in a grounded, rotating bath (30-45 rotation/min) containing 50 mM $CaCl_2$ solution with 10 units/ml thrombin (Sigma-Aldrich) for 35 min. Fibers were left in the collecting solution for 10 min and then soaked overnight in 0.25 M sodium citrate to dissolve the alginate. Fibers were then soaked in water for 60 min, bundled and stretched to 150% of their initial length, and air-dried for 60 min. Microfibers were wrapped around a custom-made plastic frame and sterilized by soaking in 75% ethanol for 2 min followed by rinsing twice with sterile water.

Cell Seeding and Culture on Fibrin Hydrogel Fibers

ECFCs, vSMCs, and pericytes were seeded on fibers as previously described in Examples 1 and 6. Briefly, cells were seeded on microfibers wrapped on a frame at a density of $4 \times 10^5$ cells/ml in 5 ml of ECFC media and tumbled overnight at 37° C. to facilitate cell attachment. For ECFCs, media was supplemented with 50 ng/mL of vascular endothelial growth factor (VEGF; Pierce, Rockford, IL, USA), whereas for pericytes media was supplemented with 30 mM aminocaproic acid (ACA; Sigma-Aldrich). At day 2 frames were transferred to 35 mm Petri dishes and cultured in the same media in a 5% $CO_2$ humidified incubator at 37° C. Media was changed every other day thereafter. For co-cultures, vSMCs or pericytes were seeded on 5 day ECFC-seeded fibrin fibers at $4 \times 10^5$ cells/ml in 5 ml of ECFC media or in ECFC media with 30 mM ACA, tumbled for 24 hours, and then transferred to 35 mm Petri dishes to continue culture. Media was changed every other day thereafter.

Preparation of 2D Fibrin Coated Surfaces

Cell culture 6-well plates and coverslips were coated with a solution of 0.2% and 0.1% fibrinogen in normal saline, respectively, and then crosslinked with 10 U/mL thrombin in 15 mM $CaCl_2$. The solutions were incubated for 15 min before being sterilized with 75% ethanol for 2 min and rinsed twice with water.

Cell Seeding and Culture on 2D Fibrin Surfaces

Cells were seeded at $1 \times 10^5$ on 6-well plates and at $5 \times 10^4$ on coverslips in the same culture media as their 3D counterpart. Samples were placed in a humidified incubator at 37° C. in a 5% $CO_2$ atmosphere and media was refreshed every other day up to 5 days of culture.

Plasmin Treatment

Fibrin microfibers with or without cells were treated with 15, 1, 0.25, and 0.1 CU/mL plasmin from human plasma (Athens Research and Technology, Athens, GA) in DMEM (Life Technologies, Grand Island, NY) for 1, 6, 12, and 24 hrs respectively in a humidified incubator at 37° C. in a 5% $CO_2$ atmosphere. Samples were imaged immediately after treatment.

Live/Dead Assay

ECFCs cultured in 2D and treated with plasmin were incubated with 2 μM calcein AM and 4 μM ethidium homodimer (Invitrogen) in PBS for 30 min at 37° C. and 5% $CO_2$. Samples were imaged immediately after and the number of live and dead cells was counted using ImageJ (NIH, Bethesda, MD).

Immunofluorescence Staining and Imaging

Samples were processed as previously described above.

Reverse Transcription Polymerase Chain Reaction

Two-step RT-PCR was performed on 2D and 3D constructs as previously described (Wanjare, M., S. Kusuma, and S. Gerecht, *Stem Cell Reports*, 2014; 2(5): 561-575). Briefly, total RNA was extracted using a TRIzol protocol (Gibco, Invitrogen) and quantified using an ultraviolet spectrophotometer. RNA was transcribed at 1 μg per sample using reverse transcriptase MMLV (Promega Co., Madison, WI) and oligo(dT) primers (Promega) according to manufacturer's instructions. TaqMan Universal PCR Master Mix and Gene Expression Assay (Applied Biosystems, Foster City, CA) were used to quantitate the expression of COL1A1, COL3A1, COL4A1, FN1, ELN, LAMC1, ACTB, GAPDH, and 18S genes (Life Technologies). The PCR step was performed for 40 cycles of 15 seconds at 95° C. and 1 min at 60° C. in an Applied Biosystems StepOne Real-TimePCR System (Applied Biosystems). Relative expressions of the genes were normalized to the amount of ACTB, GAPDH, or 18S in the same cDNA by using the comparative $\Delta\Delta C_T$ method provided by the manufacturer. Samples were run in triplicate.

Statistical Analyses

All experiments were performed in triplicate for at least 2 biological replicates. Paired t-tests were performed to compare significance between 2D and 3D gene expression (GraphPad Prism 5.01, GraphPad Software, San Diego, CA) and graphs were plotted with SEM. Significance levels were determined between samples examined and were set at $*p<0.05$, $p<0.01$, and $*p<0.001$.

Results

Deposition of ECM Proteins by ECFCs in 3D Vs 2D Substrates

We had originally shown the ability of ECFCs to deposit basal lamina proteins Col IV, Fn, and Lmn when cultured in two-dimensional (2D) petri dishes (Kusuma S, et al., *FASEB J*, 2012; 26: 4925-4936). We also demonstrated in Example 5 above the importance of micro-scale curvature in regulating the organized deposition of these ECM proteins by ECFCs utilizing fibrin microfibers of different sizes. Specifically, we showed that microfibers with diameters ranging from 100 to 400 μm guide circumferential ECM deposition by ECFCs. Here, the 3D fibrin microfibers (average diameter 188.2±13.9 μm) upregulate the amount of ECM proteins produced by ECFCs. As shown in FIG. 14, ECFCs deposit wrapping Col IV, Fn, and Lmn after 5 days in culture on 3D fibrin microfibers and 2D fibrin-coated substrates. However, higher amounts of all ECM proteins were observed in 3D vs 2D (FIG. 14A-B). Quantitative RT-PCR performed on these substrates also revealed a higher expression of the genes encoding these ECM proteins in 3D than in 2D (FIG. 14C). Together, these results show that the fibrin microfibers promote not only proper ECM organization, but also increase ECM deposition compared to 2D cultures.

Deposition of ECM Proteins by Pericytes in 3D Vs 2D Substrates

Regulation of the quantity of ECM proteins deposited by perivascular cells by substrate dimensionality was shown with pericytes seeded on fibrin microfibers following the same protocol used for ECFCs. Notably, pericytes were capable of degrading fibrin microfibers before 5 days, a finding in line with the demonstrated fibrinolytic effects of other mural cells (Grassl, E. D., et al., *J. Biomedical Materials Res.*, 2002. 60(4):607-612) but contradictory to studies that have found pericytes to express fibrinolysis inhibitors (Kim, J. A., et al., *Brain endothelial hemostasis regulation by pericytes*. J Cereb Blood Flow Metab, 2005. 26(2): 209-217). To allow study of ECM deposition after 5 days in culture the media was supplemented with 30 mM ACA, which has been previously used to inhibit plasmin activity 9 (Ahmann, K. A., et al., *Tissue Eng Part A*, 2010. 16(10): 3261-70; and Anonick, P. K., et al., *Arterioscler Thromb*, 1992. 12(6):708-716.

Figure 15A:
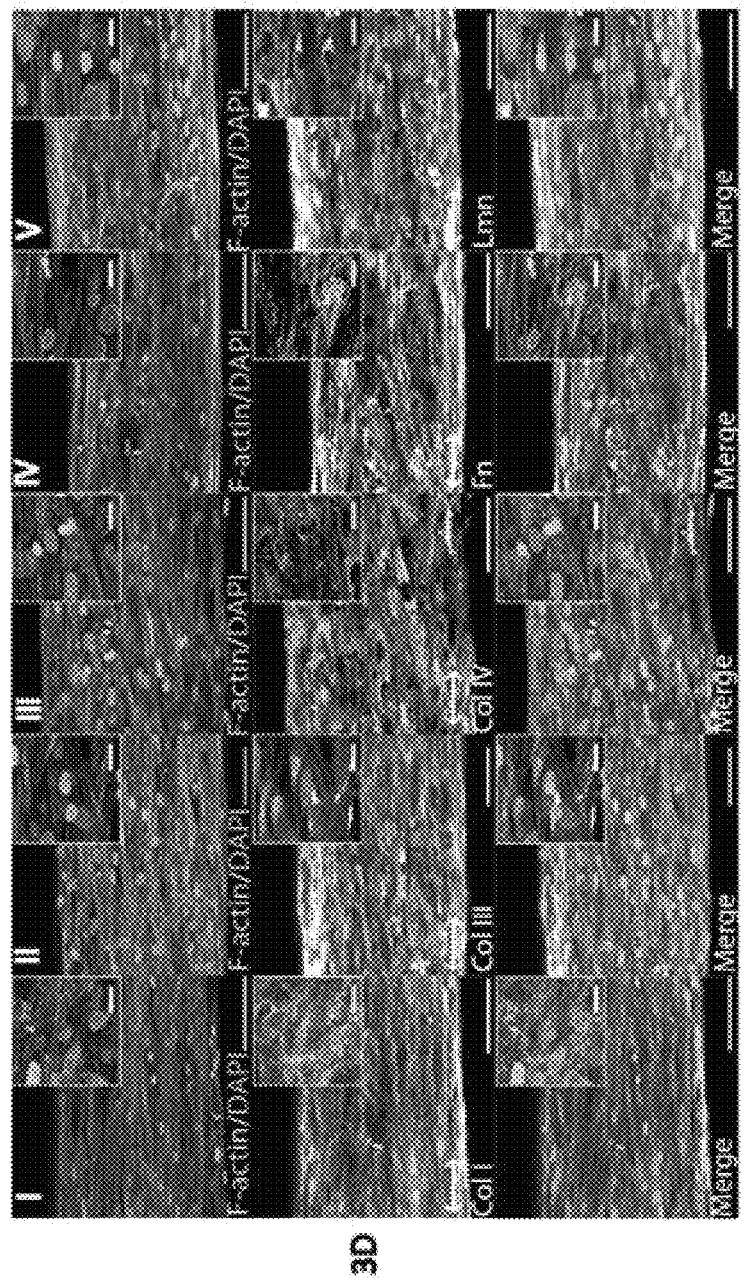
Figure 15C:
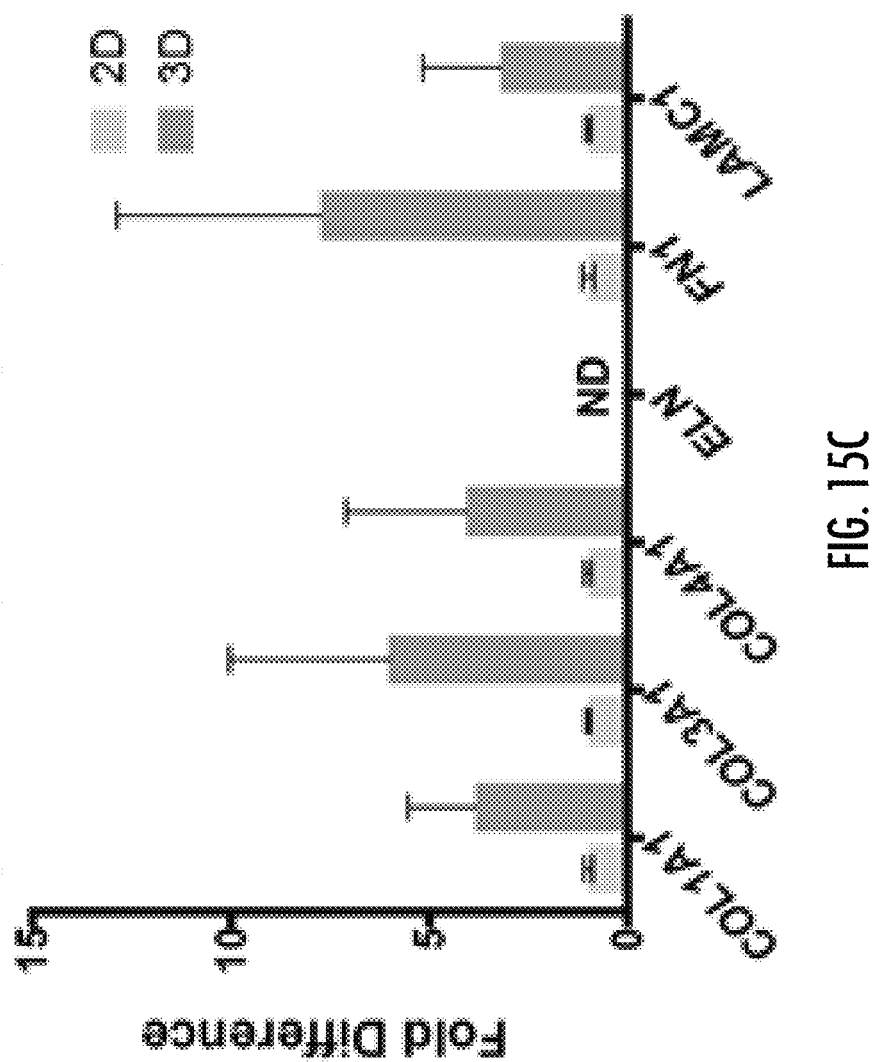
Figure 15D:
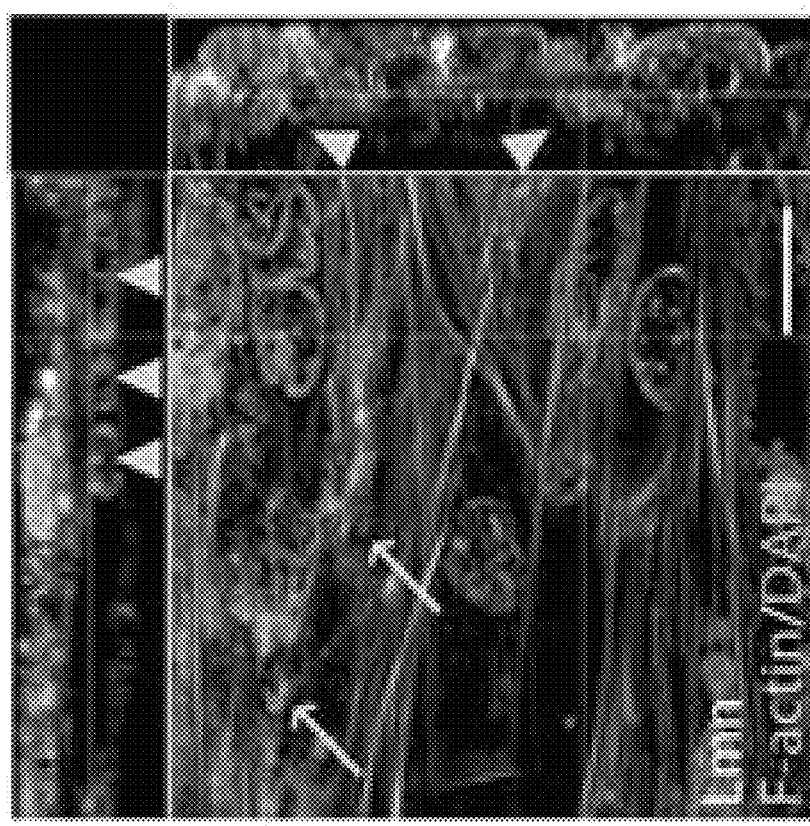

As shown in FIG. 15A, pericytes attach and grow on fibrin microfibers. Similarly to ECFCs, pericytes also produce Col IV, Fn, and Lmn both in 2D and 3D. Additionally, they deposit Col I and Col III (FIG. 15A-B). Eln deposition was not observed neither in 2D nor 3D cultures as confirmed by RT-PCR (FIG. 15C). However, the amount of ECM deposited by pericytes was not distinguishably different in 2D vs 3D based on confocal microscopy. Quantitative RT-PCR analysis revealed there is an increased expression of COL1A1, COL3A1, COL4A1, FN1, and ELN, but that this increase is variable and not statistically significant (FIG. 15C).

ECM deposition in 2D appears either randomly organized (FIG. 15B I and III), non-polymerized (FIG. 15B II and V), or following local pericyte orientation (FIG. 15B IV), whereas in 3D ECM deposition is organized parallel to the cell's orientation, which follows the longitudinal axis of the microfiber (FIG. 15A). Additionally, Lmn shows a polymerized extracellular deposition in 3D compared to 2D (FIG. 15A V, 15B V, and 15D). Lastly, pericytes can grow in a multilayer organization on the microfibers (FIG. 15D), as opposed to the monolayer formed by ECFCs.

Deposition of ECM Proteins by vSMCs in 3D Vs 2D Substrates

Figure 16A:
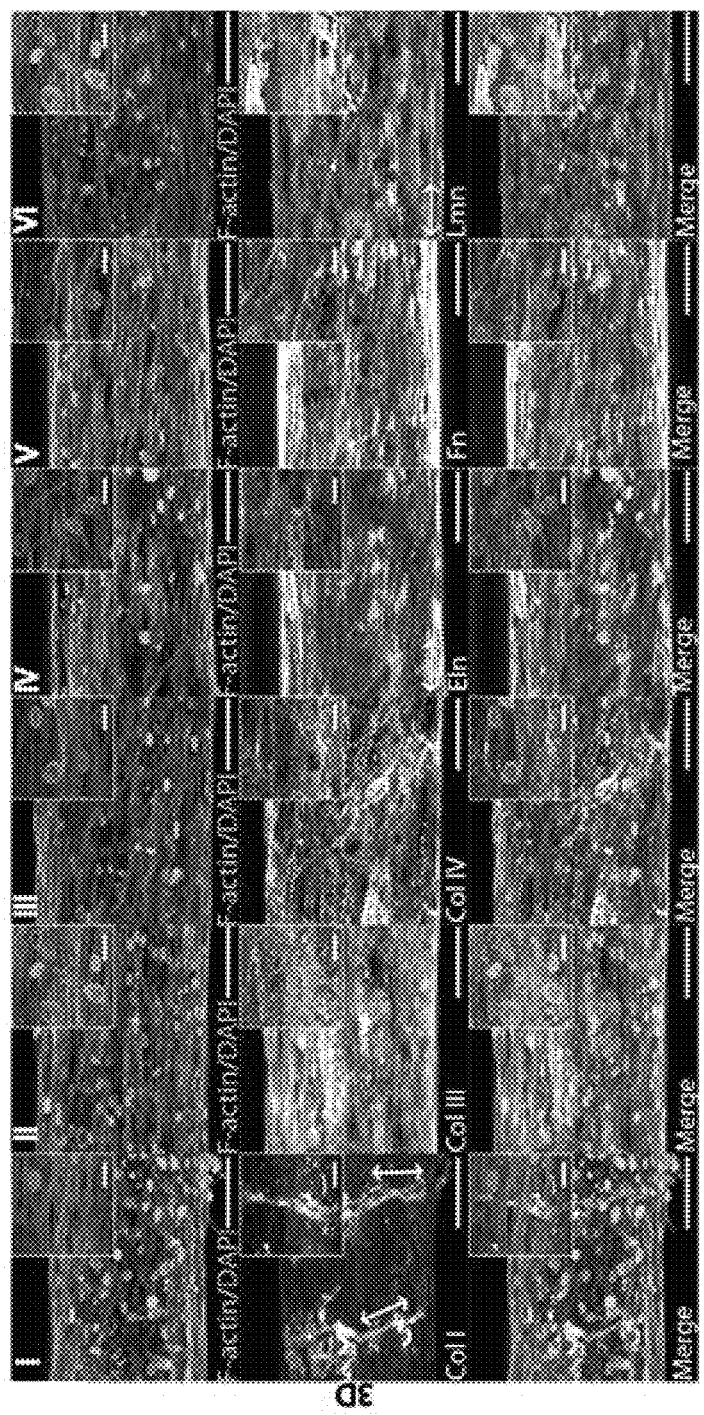

Previously in Example 6 we demonstrated that vSMCs can be introduce on ECFC-seeded fibrin microfibers and obtain full mural cell investment on the developing microvascular structures. Additionally, vSMC ECM proteins Eln and Col 1 were deposited between the ECFC and vSMC layer (Example 6). Here, the three-dimensionality of the fibrin microfibers induces a higher ECM deposition by vSMCs than 2D cultures. As seen in FIG. 16A, SMCs can attach and grow directly on the microfibers.

Figure 16B:
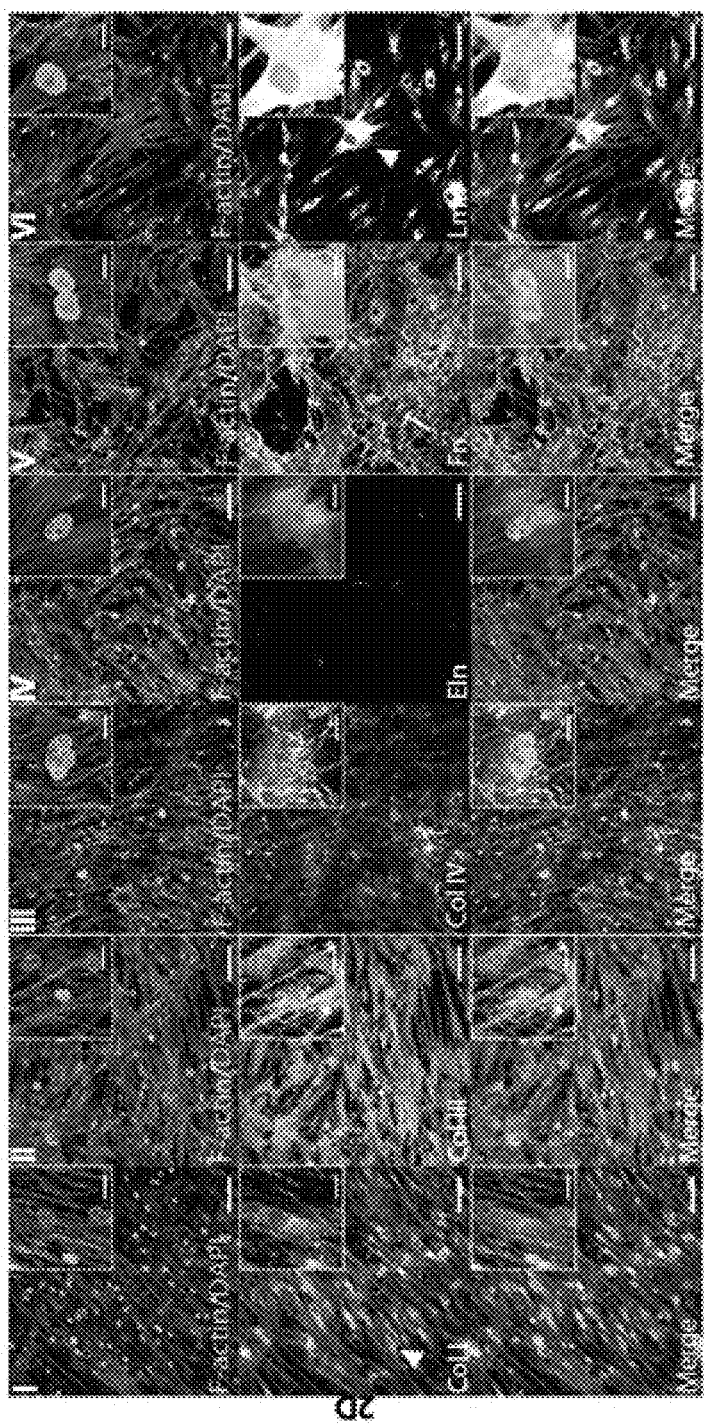
Figure 16C:
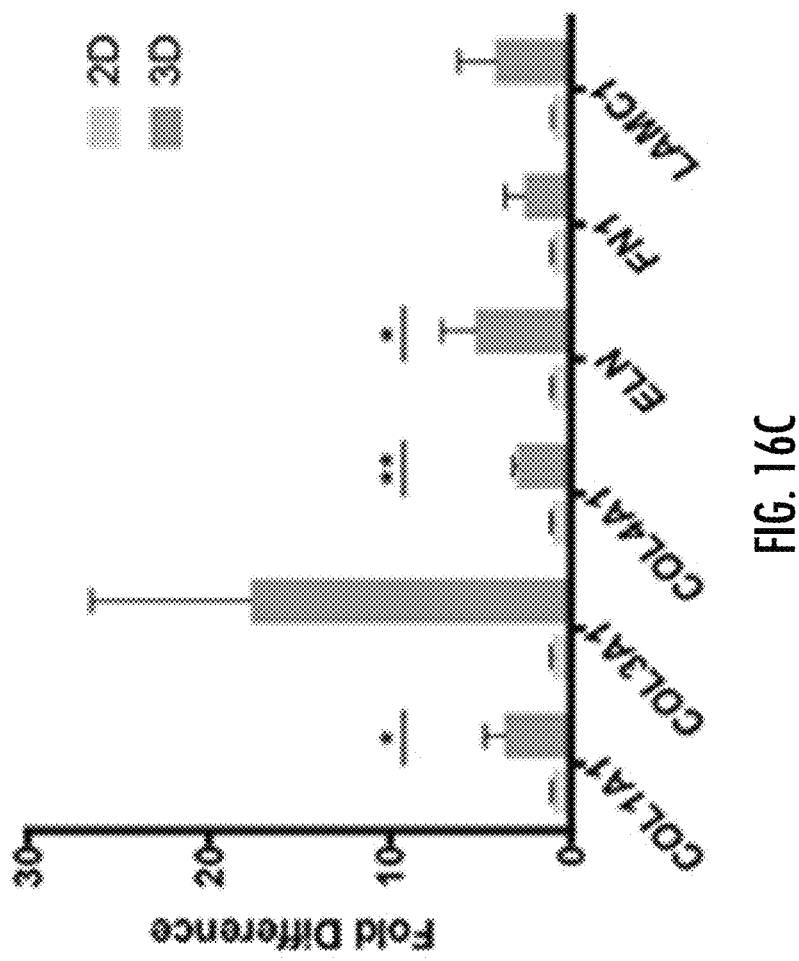

Furthermore, vSMCs deposit Col I, III, IV, Eln, Fn, and Lmn both in 2D and 3D cultures (FIG. 16A-C). Remarkably, Col I can present a wrapping orientation similar to the previously demonstrated deposition of Col IV by ECFCs when cultured in 3D, compared to a sparse mostly intracellular expression in 2D (FIG. 10AI and 10BI). Additionally, Eln, Fn, and Lmn can follow an aligned deposition with cellular orientation along the longitudinal axis of the microfiber in 3D (FIG. 16A IV-VI). In contrast, Fn and Lmn presented a random or intracellular expression in 2D, respectively (FIG. 16B V-VI).

Figure 16D:
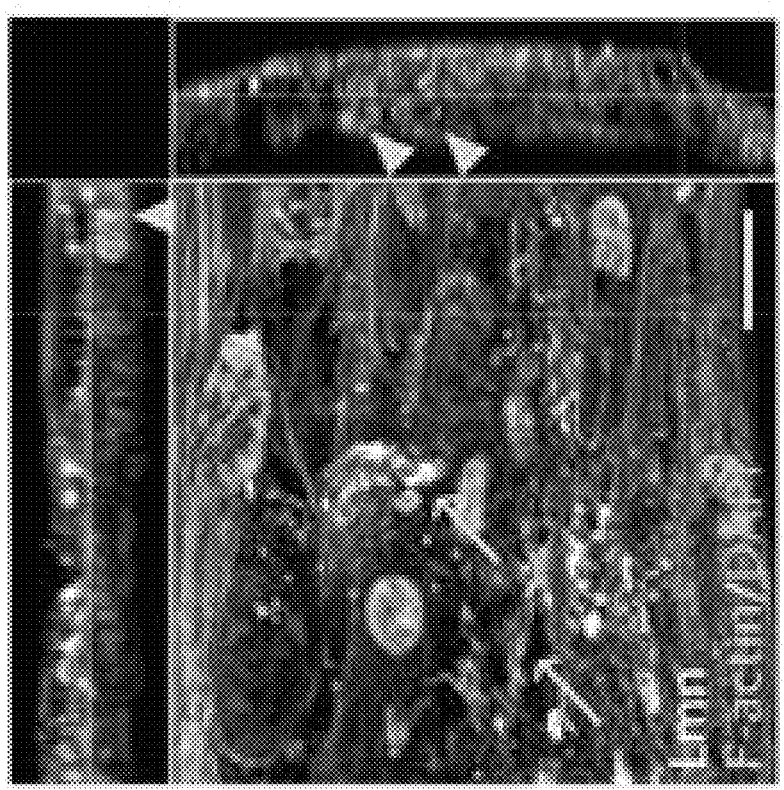

Regarding ECM quantity, Col IV and Eln were upregulated in 3D cultures, with Eln deposition being almost null in 2D but uniformly deposited in 3D (FIG. 16A IV and 16B IV). Indeed, all proteins were found to be expressed in higher quantities in 3D than in 2D via RT-PCR, though COL1A1, COL4A1, and ELN were the only genes significantly upregulated with average fold differences of 3.7, 3.0, and 4.9 compared to 2D, respectively (FIG. 16C). Similarly to pericytes, vSMCs in 3D grow in a multilayer organization and deposit polymerized Lmn extracellularly (FIG. 16D).

Fibrin Microfiber Degradation

The fibrin microfiber core was degraded after endothelial cell (EC) layer formation while maintaining both cellular viability and intact ECM organization. Fibrin microfibers without cells were treated with different concentrations of plasmin. Plasmin effectively degraded the microfibers in a concentration dependent manner; microfibers treated with a range of concentrations for 24 hrs revealed that 15, 1, 0.25, and 0.1 CU/mL plasmin degraded the microfibers in about 1, 6, 12, and 24 hrs, respectfully (FIG. 17A). Fetal bovine serum present in regular culture media was found to interfere with the degradation process (data not shown), and therefore all plasmin treatments were performed in serum-free media.

Degradation treatment maintained ECFC viability after treating confluent layers of ECFCs with the same conditions found for 1, 6, 12, and 24 hr degradation times. While both 1 hr and 6 hr treatments resulted in poor cell viability (data not shown), the 12 hr and 24 hr treatments resulted in 80.6±4.3% and 65.2±1.8% live cells, respectively (FIG. 17B), compared to 90.7±7.4% when cells were cultured in regular media (not shown).

We then tested the 12 and 24 hr degradation treatments on ECFC-seeded fibrin microfibers that had been in culture for 5 days. As shown in FIG. 17C, the previously demonstrated circumferential organization of ECM proteins Col IV, Fn, and Lmn was maintained after microfiber degradation in both 12 hr and 24 hr treatment conditions (FIG. 17C I and II respectively). Insert in FIG. 17C II shows a cross-sectional view, demonstrating the resulting lumen.

Luminal Multicellular Microvascular Structure

Figure 18A:
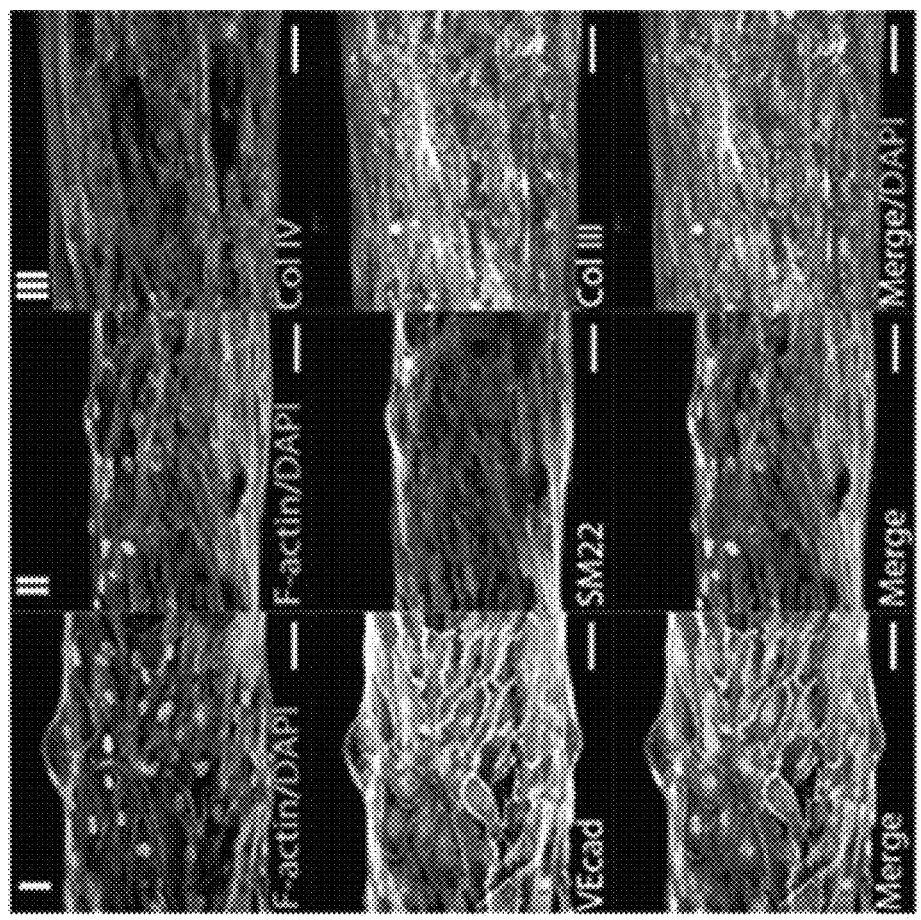
Figure 18B:
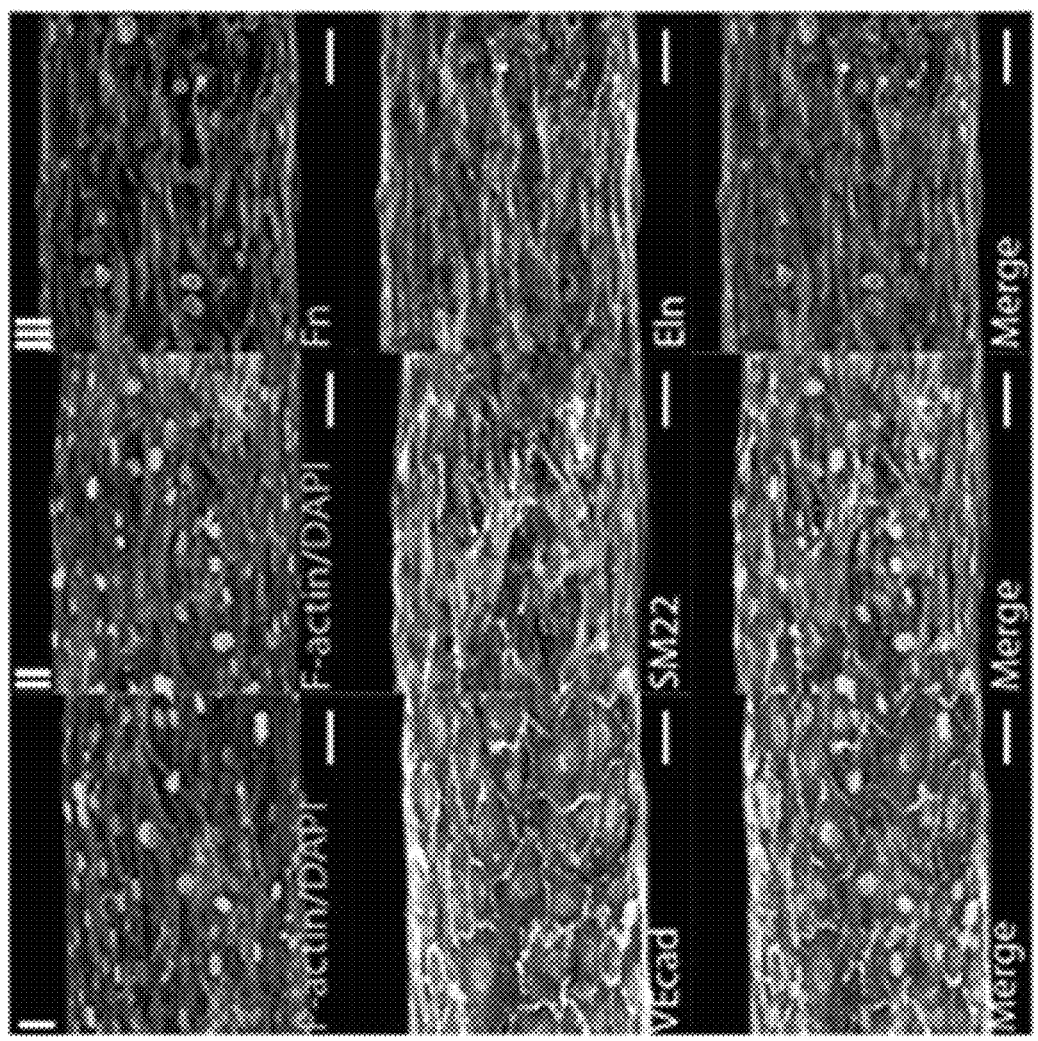
Figure 18C:
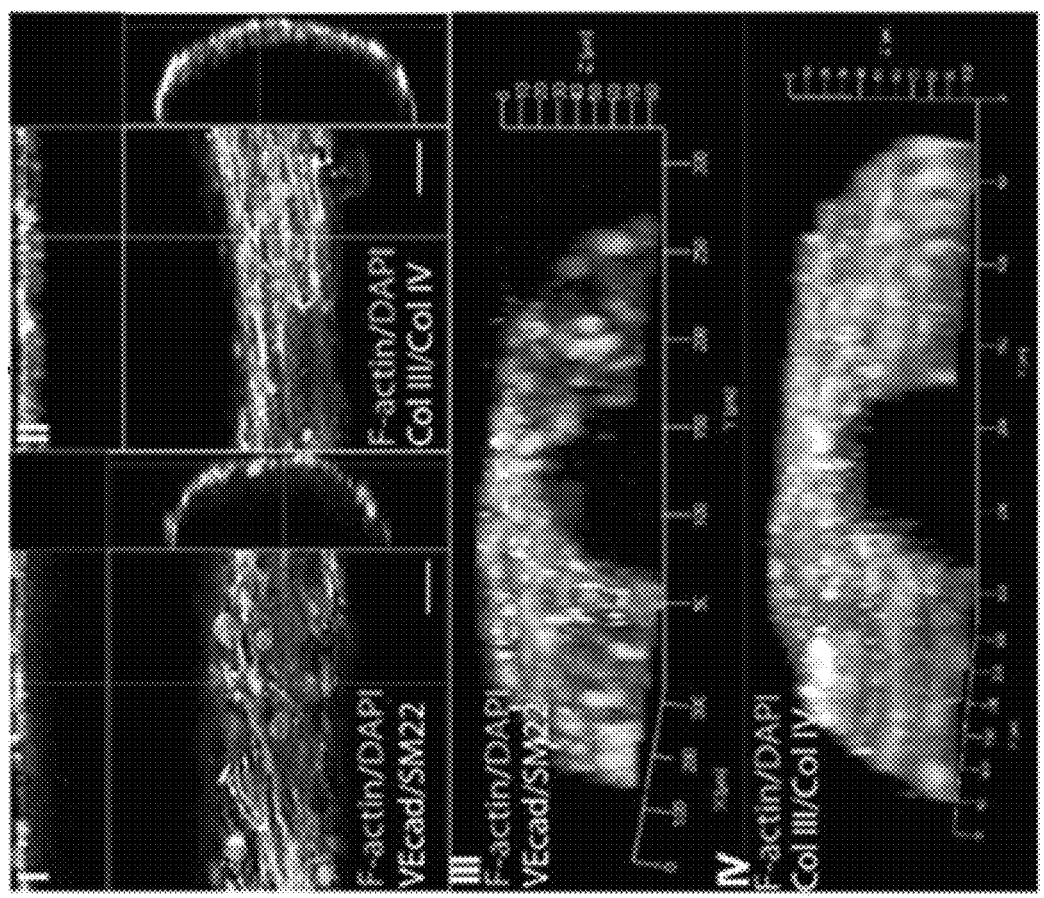

Multicellular microvascular structures were prepared by culturing ECFCs on fibrin microfibers for 5 days, introducing pericytes and/or vSMCs on top of the endothelial monolayer, and continuing culture for 5 more days. As shown in FIG. 18A-B, the resulting structures contain both an endothelial monolayer expressing the tight junction protein vascular endothelial cadherin (VEcad) and a fully invested perivascular multicellular layer expressing vSMC and pericyte marker SM22. Moreover, abundant ECM protein deposition was observed, including ECM proteins deposited by both ECFCs and mural cells as shown above (Col IV and Fn; FIGS. 18A III and 18B III), mural cells only (Col III; FIG. 18A III), and vSMCs only (Eln, FIG. 18B III). The resulting structures had a cell-ECM wall thickness of 19.9±3.1 μm and 13.6±0.6 μm for pericyte and vSMC co-cultures, respectively.

Figure 18D:
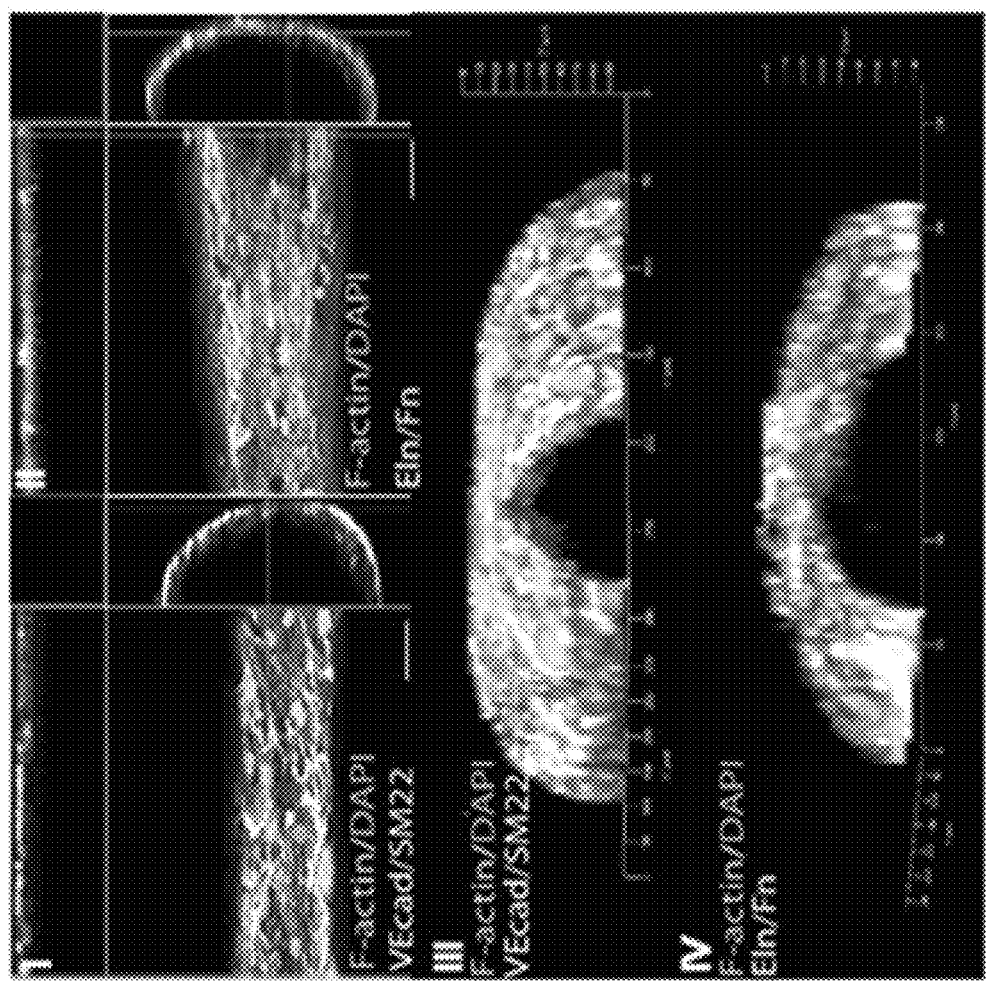

Constructs were treated with 0.25 CU/mL plasmin for 12 hrs and structures analyzed for lumen formation. As shown in the orthogonal views and 3D reconstructions of confocal microscopy images in FIG. 18C-D, both pericyte and vSMC co-cultures resulted in a distinct circular lumen comprised by ECs and perivascular cells, as evidenced by VEcad and SM22 expression. Furthermore, the structures maintained the ECM protein composition, as shown for Col III and IV (FIG. 18C) and Fn and Eln (FIG. 18D). Orthogonal projections are shown for top Z-stack slices in FIG. 18C and FIG. 18D. The 3D reconstructions show an angle view of half of the resulting cylindrical microvascular structure.

Due to confocal microscopy limitations when imaging large multicellular structures only one halve of the structure is visible (the side closest to the objective), resulting in a semi-circular cross-section. Samples were therefore flipped over and imaged on both sides to confirm structure uniformity, and images presented are representative images for both sides of the structures.

In describing the present invention and its various embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Aubin, H., Nichol, J. W., Hutson C. B., Bae, H., Sieminski, A., Cropek, D. M., Akhyari P., and Khademhosseini A. Directed 3D cell alignment and elongation in microengineered hydrogels. Biomaterials 31, 6941-6951 (2010);

Bellan, L. M. and Craighead, H. G. Molecular orientation in individual electrospun nanofibers measured via polarized Raman spectroscopy. Polymer 49, 3125-3129 (2008);

Bettinger, C. J., Langer, R. and Borenstein, J. T. Engineering Substrate Topography at the Micro- and Nanoscale to Control Cell Function. Angew. Chem. Int. Ed. 48, 5406-5415 (2009);

Burdick, J. A. and Anseth, K. S. Photoencapsulation of osteoblasts in injectable RGD-modified PEG hydrogels for bone tissue engineering. Biomaterials 23, 4315-4323 (2002);

Catalani, L. H., Collins, G. and Jaffe, M. Evidence for molecular orientation and residual charge in the electrospinning of poly(butylene terephthalate) nanofibers. Macromolecules 40, 1693-1697 (2007);

Chew, S. Y., Mi, R., Hoke, A. and Leong, K. W. The effect of the alignment of electrospun fibrous scaffolds on Schwann cell maturation. Biomaterials 29, 653-661 (2008);

Coburn, J., Gibson, M., and Bandalini, P. A. Biomimetics of the extracellular matrix: an integrated three-dimensional fiber-hydrogel composite for cartilage tissue engineering. Smart Struct Syst 7, 213-222 (2011);

Cornwell, K. G. and Pins, G. D. Discrete crosslinked fibrin microthread scaffolds for tissue regeneration. Journal of Biomedical Materials Research Part A 82A, 104-112 (2007);

Dalsin, J. L., Hu, B. H., Lee, B. P. and Messersmith, P. B. Mussel adhesive protein mimetic polymers for the preparation of nonfouling surfaces. Journal of the American Chemical Society 125, 4253-4258 (2003);

Discher, D. E., Janmey, P. and Wang, Y. L. Tissue cells feel and respond to the stiffness of their substrate. Science 310, 1139-1143 (2005);

Engler, A. J., Sen, S., Sweeney, H. L. and Discher, D. E. Matrix elasticity directs stem cell lineage specification. Cell 126, 677-689 (2006);

Fennessey, S. F. and Farris, R. J. Fabrication of aligned and molecularly oriented electrospun polyacrylonitrile nanofibers and the mechanical behavior of their twisted yarns. Polymer 45, 4217-4225 (2004);

Grasman, J. M., Page, R. L., Dominko, T. and Pins, G. D. Crosslinking strategies facilitate tunable structural properties of fibrin microthreads. Acta Biomaterialia 8, 4020-4030 (2012);

Inai, R., Kotaki, M. and Ramakrishna, S. Structure and properties of electrospun PLLA single nanofibres. Nanotechnology 16, 208-213 (2005);

Ingram, D. A., Mead, L. E., Tanaka, H., Meade, V., Fenoglio, A., Mortell, K., Pollok, K., Ferkowicz, M. J., Gilley, D., and Yoder, M. C. Identification of a novel hierarchy of endothelial progenitor cells using human peripheral and umbilical cord blood. Blood 104, 2752-2760 (2004);

Ji, Y., Ghosh, K., Li, B., Sokolov, J. C., Clark, R. A. F., and Rafailovich, M. H. Dual-syringe reactive electrospinning of cross-linked hyaluronic acid hydrogel nanofibers for tissue engineering applications. Macromol Biosci 6, 811-817 (2006);

Ji, Y., Ghosh, K., Shu, X. Z., Li, B., Sokolov, J. C., Prestwich, G. D., Clark, R. A. F., and Rafailovich, M. H. Electrospun three-dimensional hyaluronic acid nanofibrous scaffolds. Biomaterials 27, 3782-3792 (2006);

Kakade, M. V., Givens, S., Gardner, K., Lee, K. H., Chase, D. B., and Rabolt, J. F. Electric field induced orientation of polymer chains in macroscopically aligned electrospun polymer nanofibers. Journal of the American Chemical Society 129, 2777-2782 (2007);

Kang, E., Jeong, G. S., Choi, Y. Y., Lee, K. H., Khademhosseini, A., and Lee, S.-H. Digitally tunable physicochemical coding of material composition and topography in continuous microfibres. Nature Materials 10, 877-883 (2011);

Larson, R. G. and Mead, D. W. The Ericksen Number and Deborah Number Cascades in Sheared Polymeric Nematics. Liq. Cryst. 15, 151-169 (1993);

Lim, S. H. and Mao, H. Q. Electrospun scaffolds for stem cell engineering. Advanced Drug Delivery Reviews 61, 1084-1096 (2009);

Lutolf, M. P., Lauer-Fields, J. L., Schmoekel, H. G., Metters, A. T., Weber, F. E., Fields, G. B., and Hubbell, J. A., Synthetic matrix metalloproteinase-sensitive hydrogels for the conduction of tissue regeneration: Engineering cell-invasion characteristics. Proc. Natl. Acad. Sci. U.S.A. 100, 5413-5418 (2003);

MacKintosh, F. C., Kas, J. and Janmey, P. A. Elasticity of Semiflexible Biopolymer Networks. Phys Rev Lett 75, 4425-4428 (1995);

Martino, M. M., Mochizuki, M., Rothenfluh, D. A., Rempel, S. A., Hubbell, J. A., and Barker, T. H. Controlling integrin specificity and stem cell differentiation in 2D and 3D environments through regulation of fibronectin domain stability. Biomaterials 30, 1089-1097 (2009);

Nichol, J. W., Koshy, S. T., Bae, H., Hwang, C. M., Yamaniar, S., Khademhosseini, A. Cell-laden microengineered gelatin methacrylate hydrogels. Biomaterials 31, 5536-5544 (2010);

Potter, K., Balcom, B. J., Carpenter, T. A. and Hall, L. D. The Gelation of Sodium Alginate with Calcium-Ions Studied by Magnetic-Resonance-Imaging (MRI). Carbohyd Res 257, 117-126 (1994);

Reneker, D. H., Yarin, A. L., Fong, H. and Koombhongse, S. Bending instability of electrically charged liquid jets of polymer solutions in electrospinning. J. Appl. Phys. 87, 4531-4547 (2000);

Seliktar, D. Designing Cell-Compatible Hydrogels for Biomedical Applications. Science 336, 1124-1128 (2012);

Shu, X. Z., Liu, Y. C., Palumbo, F. S., Lu, Y. and Prestwich, G. D. In situ crosslinkable hyaluronan hydrogels for tissue engineering. Biomaterials 25, 1339-1348 (2004);

Silva, G. A., Czeisler, C., Niece, K. L., Beniash, E., Harrington, D. A., Kessler, J. A. and Stupp, S. I., Selective differentiation of neural progenitor cells by high-epitope density nanofibers. Science 303, 1352-1355 (2004);

Williams, C. G., Kim, T. K., Taboas, A., Malik, A., Manson, P. and Elisseeff, J. In vitro chondrogenesis of bone marrow-derived mesenchymal stem cells in a photopolymerizing hydrogel. Tissue Engineering 9, 679-688 (2003);

Yang, F., Murugan, R., Wang, S. and Ramakrishna, S. Electrospinning of nano/micro scale poly(L-lactic acid) aligned fibers and their potential in neural tissue engineering. Biomaterials 26, 2603-2610 (2005);

Zhang, S. M., Greenfield, M. A., Mata, A., Palmer, L. C., Bitton, R., Mantei, J. R., Aparicio, C., Olvera de la Cruz, M., and Stupp, S. I. A self-assembly pathway to aligned monodomain gels. Nature Materials 9, 594-601 (2010); and Zong, X. H., Kim, K., Fang, D., Ran, S., Hsiao, B. S., and Chu, B. Structure and process relationship of electrospun bioabsorbable nanofiber membranes. Polymer 43, 4403-4412 (2002).

International PCT patent application publication number WO2007/066715 for "Uniaxially Oriented Hydrogel."

Kaneko, T., et al., Mechanically drawn hydrogels uniaxially orient hydroxyapatite crystals and cell extension, Chem. Mater. 5596-5601 (2004).

Matsumoto, T., et al., Three-dimensional cell and tissue patterning in a strain fibrin gel system, PLoS ONE 2(11): e1211 (2007).

Vader, D., et al., Strain-induced alignment in collagen gels, PLoS ONE 4(6): e5902 (2009).

Guo, C. and Kaufman, L. J., Flow and magnetic field induced collagen alignment, Biomaterials 28: 1105-1114 (2007).

Freyssinet, J.-M, Torbet, J., Hudry-Clergeon, G., and Maret., G., Fibrinogen and fibrin structure and fibrin formation measured by using magnetic orientation, Proc. Nad Acad. Sci. USA 80 (1983).

U.S. Pat. No. 6,057,137 for Tissue-Equivalent Rods Containing Aligned Collagen Fibrils and Schwann Cells to Tranquillo et al., issued May 2, 2000.

U.S. Patent Application Publication No. US2011/0311949 for Aligned Collagen and Method Therefor to Akkus et al., published Dec. 9, 2010.

Tonsomboon, K., and Oyen, M. L., Composite electrospun gelatin fiber-alginate gel scaffolds for mechanically robust tissue engineered cornea, J. Mechanical Behavior of Biomedical Materials, http://dx.doi.org/10.1016/j.jmbbm.2013.03.001.

U.S. Patent Application Publication No. US2008/0299657 for Aligned Nanofibers and Related Methods of Use to Stupp et al., published Dec. 4, 2008.

Yang, Y., et al., Monitoring the effect of magnetically aligned collagen scaffolds on tendon tissue engineering by PSOCT, Proc. SPIE 7179, Optics in Tissue Engineering and Regenerative Medicine III, 717903 (Feb. 12, 2009).

Freyssinet, J.-M., et al., Fibrinogen and fibrin structure and fibrin formation measured by using magnetic orientation, Proc. Natl. Acad. Sci. USA, vol. 80: 1616-1620 (1983).

Wall, B. D., et al., Aligned macroscopic domains of optoelectronic nanostructures prepared via shear-flow assembly of peptide hydrogels, Adv. Mater., 23, 5009-5014 (2011).

Zhang, S., et al., A self-assembly pathway to aligned monodomain gels, Nature Materials, vol. 9:594-601 (2010).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A biodegradable microfiber having a longitudinally aligned nanotopography comprising biodegradable, electro-mechanically stretched, hydrogel, polymers, wherein alignment of the polymers is stabilized during gelation of the hydrogel.

2. The microfiber of claim 1, wherein the biodegradable, electro-mechanically stretched, hydrogel polymers are in the form of nanofibers, wherein the nanofibers are parallel to each other.

3. The microfiber of claim 2, wherein the nanofibers are substantially free of a ceramic.

4. The microfiber of claim 2, wherein the nanofibers form a conduit with a diameter in the range of 20 micrometers to 20 mm.

5. The microfiber of claim 2, comprising a solid bundle of the nanofibers with a diameter of 0.1 to 100 nm.

6. The microfiber of claim 1, wherein the hydrogel polymers have a water content of greater than about 90%.

7. The microfiber of claim 1 having a diameter from about 100 μm to about 500 μm based on the outer circumference of the microfiber.

8. The microfiber of claim 1, wherein the polymers are selected from the group consisting of alginate, fibrin (fibrinogen), gelatin, hyaluronic acid, and a combination thereof.

9. The microfiber of claim 8, wherein the polymers are fibrin polymers.

10. The microfiber of claim 1, further comprising endothelial progenitor cells seeded on the polymer microfiber.

11. The microfiber of claim 10, wherein the endothelial progenitor cells are endothelial colony forming cells.

12. The microfiber of claim 11, wherein the endothelial colony forming cells are aligned longitudinally to the microfiber.

13. The microfiber of claim 12, wherein the endothelial colony forming cells deposit extracellular matrix proteins, and wherein the extracellular matrix proteins are circumferentially organized, wrapping around the microfiber.

14. The microfiber of claim 13, wherein the extracellular matrix proteins include laminin, collagen IV, and fibronectin.

15. The microfiber of claim 14, wherein collagen IV, laminin, and fibronectin are deposited in higher quantities on the microfiber than on 2D cultures.

16. The microfiber of claim 1, further comprising perivascular cells seeded on the polymer microfiber.

17. The microfiber of claim 16, wherein the perivascular cells are pericytes.

18. The microfiber of claim 17, wherein the pericytes deposit extracellular matrix proteins, and wherein the extracellular matrix proteins are longitudinally organized along the microfiber.

19. The microfiber of claim 18, wherein the extracellular matrix proteins include collagen types I, III, IV, laminin, and fibronectin.

20. The microfiber of claim 19, wherein collagen types I, III, IV, laminin, and fibronectin are deposited in higher quantities on the microfiber than on 2D cultures.

21. The microfiber of claim 16, wherein the perivascular cells are vascular smooth muscle cells.

22. The microfiber of claim 21, wherein the vascular smooth muscle cells deposit extracellular matrix proteins, and wherein the extracellular matrix proteins are longitudinally, randomly, or circumferentially organized along the microfiber.

23. The microfiber of claim 22, wherein the extracellular matrix proteins include collagen types I, III, IV, elastin, laminin, and fibronectin.

24. The microfiber of claim 23, wherein collagen types I, III, IV, elastin, laminin, and fibronectin are deposited in higher quantities on the microfiber than on 2D cultures.

25. The microfiber of claim 10, further comprising a second cell type seeded on the fibrin microfiber.

26. The microfiber of claim 25, wherein the second cell type is a mural cell.

27. The microfiber of claim 26, wherein the mural cell is vascular smooth muscle cell or a pericyte.

28. The microfiber of claim 27, wherein the vascular smooth muscle cell or the pericyte encircles, is randomly oriented, or is longitudinally oriented with respect to the fibrin microfiber.

29. The microfiber of claim 28, wherein the vascular smooth muscle cell deposits collagen type I and elastin, and the pericyte deposits collagen type IV.

30. The biodegradable microfiber of claim 13 wherein the extracellular matrix proteins are induced to circumferentially organize and wrap around the microfiber by the longitudinally aligned nanotopography of the microfiber wherein the microfiber is substantially free of a chemical that promotes cell alignment.

31. A biodegradable, electro-mechanically stretched, hydrogel polymer nanofiber, wherein the polymer is stabilized during gelation of the hydrogel.

32. The nanofiber of claim 31 comprising a longitudinally aligned nanotopography.

33. The nanofiber of claim 31 wherein the nanofiber is substantially free of a ceramic.

34. The nanofiber of claim 31, wherein the hydrogel polymer nanofiber has a water content of greater than about 95%.

* * * * *

UNITED STATES PATENT AND TRADEMARK OFFICE
CERTIFICATE OF CORRECTION

| | | |
|---|---|---|
| PATENT NO. | : 11,779,682 B2 | Page 1 of 1 |
| APPLICATION NO. | : 16/152556 | |
| DATED | : October 10, 2023 | |
| INVENTOR(S) | : Sharon Gerecht et al. | |

It is certified that error appears in the above-identified patent and that said Letters Patent is hereby corrected as shown below:

In the Claims

Column 55, Line 65:
Replace "hydrogel, polymers" with --hydrogel polymers--.

Signed and Sealed this
Sixth Day of February, 2024

Katherine Kelly Vidal
*Director of the United States Patent and Trademark Office*